(12) United States Patent
Koura et al.

(10) Patent No.: US 8,008,306 B2
(45) Date of Patent: Aug. 30, 2011

(54) QUINOLINE COMPOUNDS

(75) Inventors: Minoru Koura, Higashimurayama (JP); Ayumu Okuda, Higashimurayama (JP); Takayuki Matsuda, Higashimurayama (JP); Yuki Yamaguchi, Higashimurayama (JP); Hisashi Sumida, Higashimurayama (JP); Sayaka Kurobuchi, Higashimurayama (JP); Yuichiro Watanabe, Higashimurayama (JP); Takashi Enomoto, Higashimurayama (JP); Kimiyuki Shibuya, Higashimurayama (JP)

(73) Assignee: Kowa Company, Ltd., Nagoya-shi, Aichi (JP)

( * ) Notice: Subject to any disclaimer, the term of this patent is extended or adjusted under 35 U.S.C. 154(b) by 0 days.

(21) Appl. No.: 12/430,397

(22) Filed: Apr. 27, 2009

(65) Prior Publication Data

US 2010/0016327 A1    Jan. 21, 2010

Related U.S. Application Data

(60) Provisional application No. 61/049,090, filed on Apr. 30, 2008.

(51) Int. Cl.
*C07D 215/12* (2006.01)
*C07D 215/233* (2006.01)
*C07D 241/40* (2006.01)
*A61K 31/4709* (2006.01)
*A61K 31/498* (2006.01)

(52) U.S. Cl. .............. 514/255.05; 514/311; 514/312; 514/314; 544/353; 546/153; 546/173; 546/152

(58) Field of Classification Search .............. None
See application file for complete search history.

(56) References Cited

U.S. PATENT DOCUMENTS

2005/0215577 A1    9/2005    Dehmlow

FOREIGN PATENT DOCUMENTS

| EP | 527433 A1 | * | 2/1993 |
| JP | 2002-539155 A | | 11/2002 |
| JP | 2004-509161 A | | 3/2004 |
| WO | 00/54759 A2 | | 9/2000 |
| WO | 02/24632 A2 | | 3/2002 |
| WO | 03/082192 A2 | | 10/2003 |
| WO | 2004/024161 A1 | | 3/2004 |
| WO | 2004/058717 A1 | | 7/2004 |
| WO | 2004/072046 A2 | | 8/2004 |
| WO | 2005/023188 A2 | | 3/2005 |
| WO | 2005/058834 A3 | | 6/2005 |

OTHER PUBLICATIONS

Byrn et al. Solid-State Chemistry of Drugs, 2d, Chapter 11 Hydrates and Solvates, 233-247 (1999).*
Morissette et al. Adv. Drug Delivery Rev. 2004, 56, 275-300.*
A.M. Rouhi, Chem. & Eng. News, Feb. 24, 2003, 81(8), 32-35.*
Schafer et al. Drug Discovery Today, 13:913 (2008).*
Horig et al. Journal of Translational Medicine, 2:44 (2004).*
G. Cao et al., "Antidiabetic Action of a Liver X Receptor Agonist Mediated by Inhibition of Hepatic Gluconeogenesis", The Journal of Biological Chemistry, Jan. 10, 2003, pp. 1131-1136, vol. 278, No. 10.
M. N. Bradley et al., "LXR: A nuclear receptor target for cardiovascular disease?", Drug Discovery Today: Therapeutic Strategies, 2005, pp. 97-103, vol. 2, No. 2.
N. Zelcer et al., "Liver X receptors as integrators of metabolic and inflammatory signaling", The Journal of Clinical Investigation, Mar. 2006, pp. 607-614, vol. 116, No. 3.
N. Terasaka et al., "T-0901317, a synthetic liver X receptor ligand, inhibits development of atherosclerosis in LDL receptor-deficient mice", Federation of European Biochemical Societies, 2003, pp. 6-11, Letters 536.
R. K. Tangirala et al., "Identification of macrophage liver X receptors as inhibitors of atherosclerosis", PNAS, Sep. 3, 2002, pp. 11896-11901, vol. 99, No. 18.
J. R. Schultz et al., "Role of LXRs in control of lipogenesis", Genes & Development, 2002, pp. 2831-2838.
P. H. E. Groot et al., "Synthetic LXR agonists increase LDL in CETP species", Journal of Lipid Research, 2005, pp. 2182-2191, vol. 46.
D. J. Peet et al, "Cholesterol and Bile Acid Metabolism Are Impaired in Mice Lacking the Nuclear Oxysterol Receptor LXRα", Cell, May 29, 1998, pp. 693-704, vol. 93.
S. B. Joseph et al., "Reciprocal regulation of inflammation and lipid metabolism by liver X receptors", Nature Medicine, Feb. 2003, pp. 213-219, vol. 9, No. 2. E. G. Lund et al., "Liver X Receptor Agonists as Potential Therapeutic Agents for Dyslipidemia and Atherosclerosis", Arterioscler Thromb Vasc Biol, Jul. 2003, pp. 1169-1177.
D. Auboeuf et al., "Tissue Distribution and Quantification of the Expression of mRNAs of Peroxisome Proliferator-Activated Receptors and Liver X Receptor-in Humans", Diabetes, Aug. 1997, pp. 1319-1327, vol. 46.
S. Alberti et al., "Hepatic cholesterol metabolism and resistance to dietary cholesterol in LXRβ-deficient mice", The Journal of Clinical Investigation, Mar. 2001, pp. 565-573, vol. 107, No. 5.
B. Hu et al., "Further modification on phenyl acetic acid based quinolines as liver X receptor modulators", Bioorganic & Medicinal Chemistry, 2007, pp. 3321-3333, vol. 15.

(Continued)

*Primary Examiner* — Yong Chu
*Assistant Examiner* — Michael Barker
(74) *Attorney, Agent, or Firm* — Westerman, Hattori, Daniels & Adrian, LLP

(57) ABSTRACT

To provide a novel LXRβ agonist that is useful as a preventative and/or therapeutic agent for atherosclerosis; arteriosclerosis such as those resulting from diabetes; dyslipidemia; hypercholesterolemia; lipid-related diseases; inflammatory diseases that are caused by inflammatory cytokines; skin diseases such as allergic skin diseases; diabetes; or Alzheimer's disease.

A quinoline compound represented by the following general formula (1) or salt thereof, or their solvate.

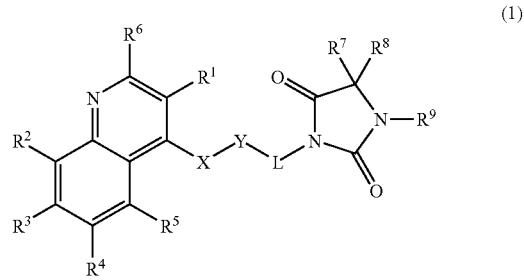

(1)

11 Claims, 7 Drawing Sheets

OTHER PUBLICATIONS

B. Hu et al., "Carboxylic acid based quinolines as liver X receptor modulators that have LXRβ receptor binding selectivity", Bioorganic & Medicinal Chemistry Letters, 2007, pp. 54-59, vol. 18.

X. Fu et al., "27-Hydroxycholesterol is an Endogenous Ligand for Liver X Receptor in Cholesterol-loaded Cells", The Journal of Biological Chemistry, 2001, pp. 38378-38387, vol. 276, No. 42.

R. Geyeregger et al., "Liver X receptors in cardiovascular and metabolic disease", Cellular and Molecular Life Sciences, 2006, pp. 524-539, vol. 63.

B. A. Janowski et al, "An oxysterol signalling pathway mediated by the nuclear receptor LXRα", Nature, Oct. 24, 1996, pp. 728-731, vol. 383.

B. Hu et al., "Discovery of Phenyl Acetic Acid Substituted Quinolines as Novel Liver X Receptor Agonists for the Treatment of Atherosclerosis", Journal of Medicinal Chemistry, Sep. 9, 2006, pp. 6151-6154, vol. 49.

T. T. Lu et al., Orphan Nuclear Receptors as eLiXiRs and FiXeRs of Sterol Metabolism, The Journal of Biological Chemistry, 2001, pp. 37735-37738, vol. 276, No. 41.

D. S. Lala, "The liver X receptors", Current Opinion in Investigational Drugs, 2005, pp. 934-943, vol. 6, No. 9.

J. M. Lehmann et al., "Activation of the Nuclear Receptor LXR by Oxysterols Defines a New Hormone Response Pathway", The Journal of Biological Chemistry, 1997, pp. 3137-3140, vol. 272, No. 6.

B. A. Laffitte et al., "Activation of liver X receptor improves glucose tolerance through coordinate regulation of glucose metabolism in liver and adipose tissue", PNAS, Apr. 29, 2003, pp. 5419-5424, vol. 100, No. 9.

* cited by examiner

| Example | Structure | Activity |
|---|---|---|
| T0901317 | (structure: bis-trifluoromethyl carbinol phenyl sulfonamide with N-CH2CF3) | (dose-response curve showing LXRα and LXRβ activation, Luciferase activity vs T0901317 10μM, 0%–350%, concentration 0.01–10.0 μM) |
| Example 1 | (structure: benzodioxole-substituted hydantoin linked via alkyl-O chain to 3-benzyl-8-trifluoromethylquinoline) | (dose-response curve showing LXRα and LXRβ activation, Luciferase activity vs T0901317 10μM, 0%–350%, concentration 0.01–1.00 μM) |

Fig. 1

| Example | Structure | Activity |
|---|---|---|
| T0901317 | (structure of T0901317) | (dose-response curve for LXRα and LXRβ, 0.1–10 µM) |
| Example 25 | (structure of Example 25) | (dose-response curve for LXRα and LXRβ, 0.01–10 µM) |

QUINOLINE COMPOUNDS

TECHNICAL FIELD

The present invention relates to a quinoline compound which is a novel LXRβ agonist useful as a preventative and/or therapeutic agent for atherosclerosis; arteriosclerosis such as those resulting from diabetes; dyslipidemia; hypercholesterolemia; lipid-related diseases; inflammatory diseases that are caused by inflammatory cytokines; skin diseases such as allergic skin diseases; diabetes; or Alzheimer's disease.

BACKGROUND ART

Liver X receptor (LXR) is a nuclear receptor that was cloned as an orphan receptor whose ligand and function were both unknown. Subsequent study reported that some oxysterols including (R)-22-hydroxycholesterol act as a ligand for LXR (non-patent documents 1 to 3). LXR, together with retinoid X receptor (RXR) which is another nuclear receptor, forms a heterodimer, to ligand-dependently control the transcription of a target gene.

As mammal LXR sub-types, two types of LXR genes (α and β) are known to exist. LXRα and LXRβ recognize the same sequence on a DNA and activate the transcription of a neighboring target gene. However, the expression-distributions of the two genes differ greatly. LXRα is specifically expressed on cholesterol metabolism-related tissues such as the liver, small intestines, or adipose tissues, whereas LXRβ is expressed ubiquitously on almost all tissues that have been examined (non-patent documents 4 and 5).

Many of the group of genes identified as target genes of LXRs are genes (ApoE, CETP, and LPL) related to a reverse cholesterol transport (RCT), including ABC transporters (ABCA1, ABCG1, ABCG5, and ABCG8). Therefore, it is expected that the activation of LXRs elevates the expression of these genes and activates reverse cholesterol transport pathways, thereby increases cholesterol efflux from the periphery and then increases HDL cholesterols and also lowers cholesterol content at an arteriosclerosis-affected region (non-patent document 6).

Further, LXRs are reported to play an important role via NF-κB suppression, in the expression control of inflammatory mediators such as NO-synthase, cyclooxygenase-2 (COX-2), and interleukin-6 (IL-6) (non-patent document 7). It is well known that the inflammation is very important at an arteriosclerosis-affected region, and it is expected that LXR ligands or LXR agonists will prevent arteriosclerosis exacerbation due to the expression of macrophage-inflammatory mediators at the affected region (non-patent documents 6 and 8).

Further, LXRα- and LXRβ-deficient mice fed on high-cholesterol diet have been reported to show symptoms such as fatty liver and elevated LDL-cholesterol level as well as reduced HDL-cholesterol level in the blood as compared to the case of normal mice fed on high-cholesterol diet (non-patent documents 9 and 10). More specifically, it is strongly suggested that LXRs play an important role in cholesterol metabolism. Moreover, by analyzing the symptoms of arteriosclerosis mouse models having normal LXRα and LXRβ functions in the liver, small intestines and the like but lacking LXRα and LXRβ in macrophages, it has been revealed that LXRα and LXRβ activities in macrophages strongly affect the incidence of arteriosclerosis (non-patent document 11). Therefore, the activation of reverse cholesterol transport through the LXR activation especially in macrophages is considered to be important for the treatment of arteriosclerosis.

As for the applications, LXR regulators or LXR agonists disclosed in the prior art documents are reported to have been applied to diseases such as hypercholesterolemia and atherosclerosis (patent documents 1 and 2). Further, LDL-receptor-deficient mice loaded with high-fat food, and administered with LXR ligand, have been reported to show an elevated HDL cholesterol level, lowered VLDL and LDL cholesterol levels, and reduced area of arteriosclerosis-affected region (non-patent document 12).

Further, LXR ligands or LXR agonists are expected to control sugar metabolism in the liver and adipose tissues, and thus to improve diabetes (non-patent documents 6 and 8). Recently, it has been reported that an administration of LXR agonist improved insulin sensitivity and blood glucose level in diabetes animal models (non-patent documents 13 and 14). Moreover, it is indicated as a potential therapeutic drug for Alzheimer's disease, inflammatory diseases, or skin diseases (non-patent document 15).

LXR agonists, however, are reported to increase LDL cholesterol in animal species having cholesteryl ester transfer proteins (CETP) (non-patent document 16). Further, in animal experiments, it has been observed that LXR activation in the liver by the LXR agonist administration enhances fatty-acid and triglyceride syntheses through the transcriptional activation of enzymes that are important for fatty-acid synthesis, for example, fatty-acid synthase (FAS) or stearyl-CoA fatty-acid desaturase (SCD-1) (non-patent document 17). Meanwhile, nothing is disclosed in the prior art documents on LXR α/β selectivity in relation to the disclosed LXR regulators, LXR ligands, LXR agonists and the like.

Therefore, there have been demands for an ideal synthetic LXR-binding compound without a dyslipidemia-exacerbating effect which acts through an elevated fatty-acid and triglyceride syntheses, while maintaining the agonist activity for reverse cholesterol transport activation by ABC transporters and for increased cholesterol-efflux from macrophages. As one approach to solve the problem, a compound that selectively activates LXRβs is considered to have an ideal profile that is expected to suppress the activation of LXRα highly expressed on the liver, as compared to the LXR regulators disclosed in the prior art documents, and to suppress the concerned side-effects of fatty-acid and triglyceride synthesis elevations (non-patent documents 6, 8, 15, 18, and 19). However, because ligand-binding sites of LXRα and LXRβ are highly homologous, it is considered that the creation of a compound that acts differently on LXRα and LXRβ is not easy.

In fact, compounds having an LXR-agonist effect have been reported, such as a benzofuran-5-acetic acid derivative (patent document 3), 2-aminoquinazoline-4-one derivative (patent document 4), tetrahydroquinoline derivative (non-patent document 5), tetrahydrocarbazol derivative (patent document 6), isoquinoline derivative (patent document 7), and naphthalene derivative (patent document 8), GW3965 which is an aromatic aminoalcohol derivative (Example 16 described in patent document 9), and T0901317 which is a benzenesulfonamide derivative (Example 12 described in patent document 10), but no agonist with high LXRβ selectivity has been reported to date.

Meanwhile, an LXR agonist having a quinoline skeleton has been reported (patent document 11, non-patent documents 20 to 22). For example, WAY-254011 (compound 4 of non-patent document 22) which is a quinoline derivative has been reported to have LXRβ-selective binding affinity (α/β ratio is 1 to 5). Non-patent document 22 further reports on a compound showing an α/β ratio of up to 1 to 50 in terms of binding-affinity. However, as for an agonist effect which was measured by Gal 4 transactivation activity, the highest selectivity confirmed was an α/β ratio of merely up to about 1 to 2.7. This shows that the effect of the compound on LXR for expressing the target gene is weak despite the selective binding of the compound to LXRβ. Therefore, there are still strong demands for a compound having an effect of expressing a target gene in an LXRβ selective manner.

[Patent Document 1] Published Japanese translation of PCT international publication No. 2002-539155
[Patent Document 2] Published Japanese translation of PCT international publication No. 2004-509161
[Patent Document 3] WO2003/82192
[Patent Document 4] WO2004/24161
[Patent Document 5] WO2004/72046
[Patent Document 6] U.S Patent publication No. 2005/215577
[Patent Document 7] WO2004/58717
[Patent Document 8] WO2005/23188
[Patent Document 9] WO2002/24632
[Patent Document 10] WO2000/54759
[Patent Document 11] WO2005/58834
[Non-patent Document 1] Janowski et al., Nature, 383, pp. 728-731, 1996
[Non-patent Document 2] Lehmann et al., J. Biol. Chem., 272, pp. 3137-3140, 1997
[Non-patent Document 3] Fu et al., J. Biol. Chem., 276, pp. 38378-38387, 2001
[Non-patent Document 4] Auboeuf et al., Diabetes, 46, pp. 1319-1327, 1997
[Non-patent Document 5] Lu et al., J. Biol. Chem., 276, pp. 37735-37738, 2001
[Non-patent Document 6] Zelcer et al., J. Clin. Invest., 116, pp. 607-614, 2006
[Non-patent Document 7] Joseph et al., Nat. Med., 9, pp. 213-219, 2003
[Non-patent Document 8] Geyeregger et al., Cell. Mol. Life. Sci. 63, pp. 524-539, 2006
[Non-patent Document 9] Peet et al., Cell, 93, pp. 693-704, 1998
[Non-patent Document 10] Alberti et al., J. Clin. Invest., 107, pp. 565-573, 2001
[Non-patent Document 11] Tangirala et al., Proc. Natl. Acad. Sci. USA, 99, pp. 11896-11901, 2002
[Non-patent Document 12] Terasaka et al., FEBS Lett., 536, pp. 6-11, 2003
[Non-patent Document 13] Cao et al., J. Biol. Chem., 278, pp. 1131-1136, 2003
[Non-patent Document 14] Laffitte et al., Proc. Natl. Acad. Sci. USA, 100, pp. 5419-5424, 2003
[Non-patent Document 15] Lala et al., Curr. Opin. Investig. Drugs, 6, pp. 934-943, 2005
[Non-patent Document 16] Groot et al., J. Lipid Res., 46, pp. 2182-2191, 2005
[Non-patent Document 17] Schultz et al., Genes Dev., 14, pp. 2831-2838, 2000
[Non-patent Document 18] Lund et al., Arterioscler. Thromb. Vasc. Biol., 23, pp. 1169-1177, 2003
[Non-patent Document 19] Bradley et al., Drug Discov. Today Ther. Strateg. 2, pp. 97-103, 2005
[Non-patent Document 20] Hu et al., J. Med. Chem., 49, pp. 6151-6154, 2006
[Non-patent Document 21] Hu et al., Bioorg. Med. Chem., 15, pp. 3321-3333, 2007
[Non-patent Document 22] Hu et al., Bioorg. Med. Chem. Lett., 18, pp. 54-59, 2008

DISCLOSURE OF THE INVENTION

Problem to be Solved by the Invention

Thus, the object of the present invention is to prepare a novel compound that exhibits an agonist activity with high LXRβ selectivity.

Means to Solve the Problem

The present inventors made a keen study to achieve the above object and consequently, found that a compound having a quinoline skeleton in combination with an imidazolidine-2,4-dione skeleton represented by general formula (1) described hereinbelow has an agonist activity with high LXRβ selectivity, and thus completed the present invention.

More specifically, the present invention relates to
[1] a quinoline compound represented by the following general formula (1) or salt thereof, or their solvate:

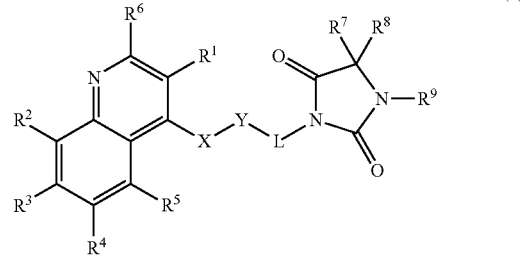

(1)

(wherein $R^1$ represents a hydrogen atom, halogen atom, $C_{1-8}$ alkyl group, $C_{3-8}$ cycloalkyl group, $C_{2-8}$ alkenyl group, $C_{3-8}$ cycloalkenyl group, $C_{3-8}$ cycloalkenyl-$C_{1-8}$ alkyl group, $C_{1-8}$ alkoxy group, $C_{6-10}$ aryl group, $C_{6-10}$ aryl $C_{1-8}$ alkyl group, $C_{6-10}$ aryl $C_{2-6}$ alkenyl group, $C_{1-8}$ acyl group, $C_{6-10}$ arylcarbonyl group, $C_{1-8}$ alkylthio group, $C_{1-8}$ alkylsulfinyl group, $C_{1-8}$ alkylsulfonyl group, $C_{6-10}$ arylsulfonyl group, nitro group, amino group, mono $C_{1-8}$ alkylamino group, di $C_{1-8}$ alkylamino group, $C_{3-8}$ cycloalkyl $C_{1-8}$ alkyl group, $C_{3-8}$ cycloalkyl $C_{2-8}$ alkenyl group, $C_{3-8}$ cycloalkyl $C_{2-8}$ alkynyl group, halo $C_{1-8}$ alkyl group, or cyano group, wherein the $C_{6-10}$ aryl may be substituted with 1 to 3 same or different substituents selected from the following group A; $R^2$ represents a hydrogen atom, $C_{1-8}$ alkyl group, halo $C_{1-8}$ alkyl group, or halogen atom; $R^3$, $R^4$, $R^5$, and $R^6$ each independently represents a hydrogen atom, halogen atom, or $C_{1-8}$ alkyl group; $R^7$ and $R^8$ each independently represents a hydrogen atom, $C_{1-8}$ alkyl group, $C_{3-8}$ cycloalkyl group, $C_{3-8}$ cycloalkyl $C_{1-8}$ alkyl group, $C_{6-10}$ aryl group, or 5- to 11-membered heterocyclic group, wherein the $C_{6-10}$ aryl and 5- to 11-membered heterocycle may be substituted with 1 to 3 same or different substituents selected from the following group A, or $R^7$ and $R^8$ may together form a 5- to 7-membered carbocycle; $R^9$ represents a hydrogen atom, $C_{1-8}$ alkyl group, halo $C_{1-6}$ alkyl group, $C_{3-8}$ cycloalkyl group, or $C_{3-8}$ cycloalkyl $C_{1-8}$ alkyl group; X represents a bond or a $C_{1-8}$ alkyl chain, $C_{6-10}$ aryl chain, or 5- to 11-membered heteroaryl chain; Y represents a —O—, —S—, or —N($R^{10}$)—; $R^{10}$ represents a hydrogen atom or $C_{1-8}$ alkyl group; and L represents a $C_{1-8}$ alkyl chain or $C_{2-8}$ alkenyl chain)

[Group A: halogen atom, $C_{1-8}$ alkyl group, halo $C_{1-8}$ alkyl group, $C_{2-8}$ alkenyl group, $C_{2-8}$ alkynyl group, $C_{3-8}$ cycloalkyl group, cyano group, nitro group, hydroxy group, amino group, mono $C_{1-8}$ alkylamino group, di $C_{1-8}$ alkylamino group, $C_{1-8}$ alkoxy group, halo $C_{1-8}$ alkoxy group, $C_{1-8}$ acyl group, carboxyl group, $C_{1-8}$ acyloxy group, $C_{1-8}$ alkoxycarbonyl group, carbamoyl group, $C_{6-10}$ aryl group, 5- to 11-membered heteroaryl group, $C_{6-10}$ aryl $C_{1-8}$ alkoxy group, $C_{1-8}$ alkylthio group, $C_{1-8}$ alkylsulfinyl group, $C_{1-8}$ alkylsulfonyl group, $C_{6-10}$ arylthio group, $C_{6-10}$ arylsulfinyl group, and $C_{6-10}$ arylsulfonyl group];

[2] the quinoline compound or salt thereof, or their solvate according to [1], wherein $R^1$ is a $C_{1-8}$ alkyl group or $C_{6-10}$ aryl $C_{1-8}$ alkyl group;

[3] the quinoline compound or salt thereof, or their solvate according to [1] or [2], wherein $R^2$ is a halo $C_{1-8}$ alkyl group;

[4] the quinoline compound or salt thereof, or their solvate according to any one of [1] to [3], wherein $R^7$ and $R^8$ are each independently a $C_{1-8}$ alkyl group, $C_{6-10}$ aryl group, or 5- to 11-membered heterocyclic group, wherein the $C_{6-10}$ aryl and 5- to 11-membered heterocycle may be substituted with 1 to 3 same or different substituents selected from the following group A,

[Group A: halogen atom, $C_{1-8}$ alkyl group, halo $C_{1-8}$ alkyl group, $C_{2-8}$ alkenyl group, $C_{2-8}$ alkynyl group, $C_{3-8}$ cycloalkyl group, cyano group, nitro group, hydroxy group, amino group, mono $C_{1-8}$ alkylamino group, di $C_{1-8}$ alkylamino group, $C_{1-8}$ alkoxy group, halo $C_{1-8}$ alkoxy group, $C_{1-8}$ acyl group, carboxyl group, $C_{1-8}$ acyloxy group, $C_{1-8}$ alkoxycarbonyl group, carbamoyl group, $C_{6-10}$ aryl group, 5- to 11-membered heteroaryl group, $C_{6-10}$ aryl $C_{1-8}$ alkoxy group, $C_{1-8}$ alkylthio group, $C_{1-8}$ alkylsulfinyl group, $C_{1-8}$ alkylsulfonyl group, $C_{6-10}$ arylthio group, $C_{6-10}$ arylsulfinyl group, and $C_{6-10}$ arylsulfonyl group];

[5] a medicine containing the quinoline compound or salt thereof, or their solvate according to any one of [1] to [4] as an active ingredient;

[6] the medicine according to [5], which is a preventative and/or therapeutic agent for atherosclerosis, arteriosclerosis resulting from diabetes, dyslipidemia, hypercholesterolemia, lipid-related diseases, inflammatory diseases that are caused by inflammatory cytokines, skin diseases, diabetes, or Alzheimer's disease;

[7] an LXR regulator containing the quinoline compound or salt thereof, or their solvate according to any one of [1] to [4] as an active ingredient;

[8] a pharmaceutical composition consisting of the quinoline compound or salt thereof, or their solvate according to any one of [1] to [4] and a pharmaceutically acceptable carrier;

[9] a method for preventing and/or treating atherosclerosis, arteriosclerosis resulting from diabetes, dyslipidemia, hypercholesterolemia, lipid-related diseases, inflammatory diseases that are caused by inflammatory cytokines, skin diseases, diabetes, or Alzheimer's disease, which method comprises administering the quinoline compound or salt thereof, or their solvate according to any one of [1] to [4]; and

[10] use of the quinoline compound or salt thereof, or their solvate according to any one of [1] to [4] for a production of a formulation for preventing and/or treating atherosclerosis, arteriosclerosis resulting from diabetes, dyslipidemia, hypercholesterolemia, lipid-related diseases, inflammatory diseases that are caused by inflammatory cytokines, skin diseases, diabetes, or Alzheimer's disease.

Effect of the Invention

The quinoline compound represented by general formula (1) of the present invention has an LXRβ agonist effect and is useful as a preventative and/or therapeutic agent or the like for atherosclerosis, arteriosclerosis such as those resulting from diabetes; dyslipidemia; hypercholesterolemia; lipid-related diseases; inflammatory diseases caused by inflammatory cytokines, such as rheumatoid arthritis, osteoarthritis, allergic diseases, asthma, sepsis, psoriasis, and osteoporosis; autoimmune diseases such as systemic erythematosus, ulcerative colitis, and Crohn's disease; cardiovascular diseases such as ischemic cardiac disease and heart failure; cerebrovascular diseases; kidney diseases; diabetes; diabetes complications such as retinopathy, nephropathy, nerve disease, and coronary arterial disease; skin diseases such as allergic skin disease; obesity; nephritis; hepatitis; cancer; or Alzheimer's disease, and more preferably, as a preventative and/or therapeutic agent or the like for atherosclerosis, arteriosclerosis such as those resulting from diabetes, dyslipidemia, hypercholesterolemia, lipid-related diseases, inflammatory diseases that are caused by inflammatory cytokines, skin diseases such as allergic skin diseases, diabetes, or Alzheimer's disease.

BRIEF EXPLANATION OF THE DRAWINGS

FIGS. 1 to 4 show the comparison in luciferase activity results between the embodiments of the present invention and the related art (T0901317).

DETAILED DESCRIPTION OF THE INVENTION

Figure 2:
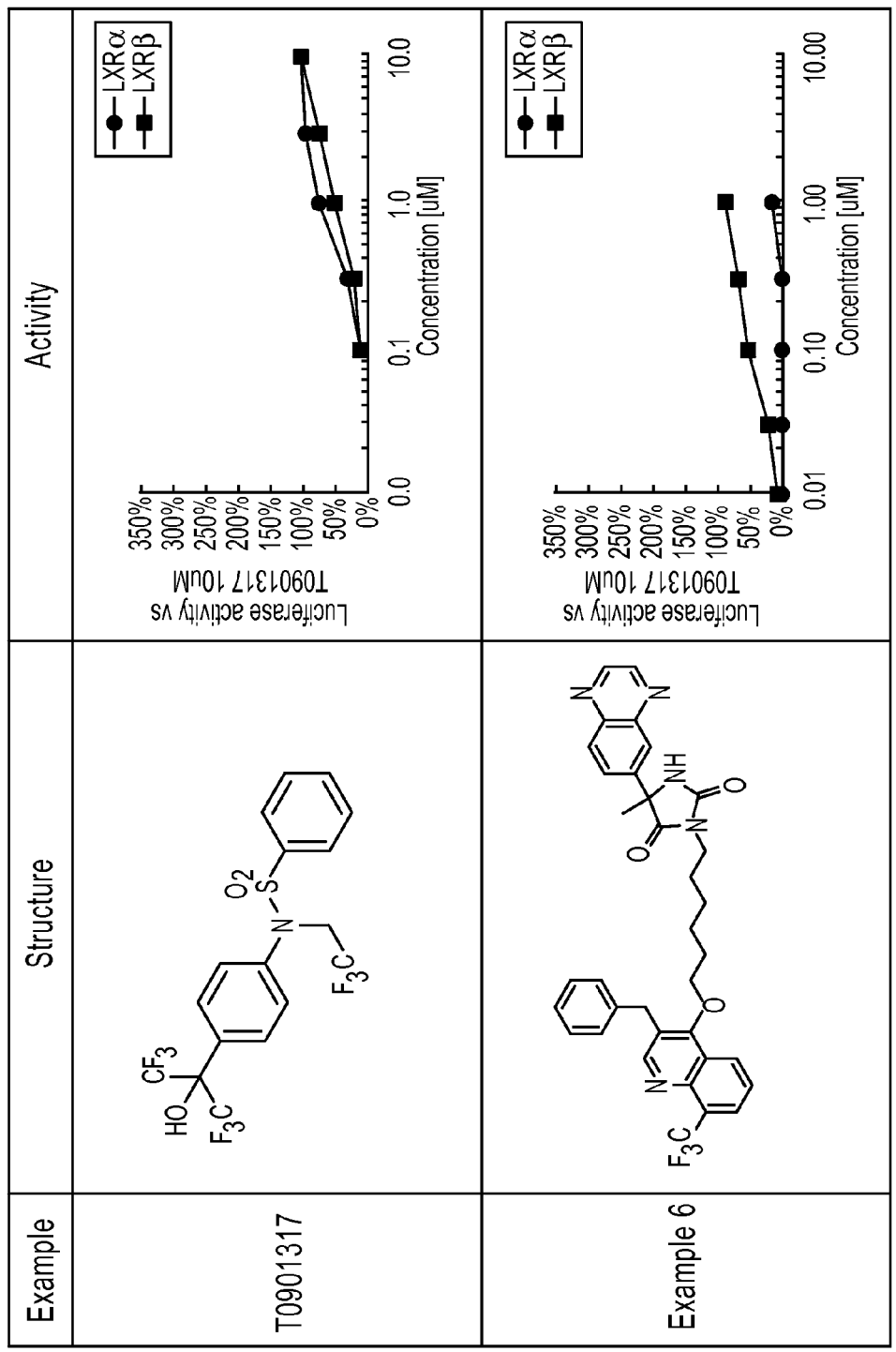

The terms in the present invention are defined as follows.

In the present invention, examples of a "halogen" atom in the halogen atom, halo $C_{1-8}$ alkyl group, or halo $C_{1-8}$ alkoxy group include a fluorine atom, chlorine atom, bromine atom, and iodine atom.

In the present invention, a "$C_{1-8}$ alkyl group" means a straight-chained or branched-chained alkyl group with 1 to 8 carbons, and the examples include a methyl group, ethyl group, n-propyl group, isopropyl group, n-butyl group, isobutyl group, t-butyl group, n-pentyl group, isopentyl group, neopentyl group, 2-methylbutyl group, 2,2-dimethylpropyl group, n-hexyl group, isohexyl group, n-heptyl group, and n-octyl group.

In the present invention, a "halo $C_{1-8}$ alkyl group" means a group wherein, preferably, 1 to 9 halogen atoms are bound to the $C_{1-8}$ alkyl group and the examples include trifluoromethyl group, 2-fluoroethyl group, 2-chloroethyl group, 2-bromoethyl group, 3-fluoropropyl group, 3-chloropropyl group, 4-fluorobutyl group, 4-chlorobutyl group, 2,2,2-trifluoroethyl group, 3,3,3-trifluoropropyl group, pentafluoroethyl group, and 2,2,2-trifluoro-1-trifluoromethylethyl group.

In the present invention, a "$C_{2-8}$ alkenyl group" means a straight-chained or branched-chained alkenyl group with 2 to 8 carbons, having a carbon-carbon double bond at any one or more sites on the alkyl chain. The examples include an ethenyl group, prop-1-en-1-yl group, prop-2-en-1-yl group, prop-1-en-2-yl group, but-1-en-1-yl group, but-2-en-1-yl group, but-3-en-1-yl group, but-1-en-2-yl group, but-3-en-2-yl group, pent-1-en-1-yl group, pent-4-en-1-yl group, pent-1-en-2-yl group, pent-4-en-2-yl group, 3-methyl-but-1-en-1-yl group, hex-1-en-1-yl group, hex-5-en-1-yl group, hept-1-en-1-yl group, hept-6-en-1-yl group, oct-1-en-1-yl group, and oct-7-en-1-yl group.

In the present invention, a "$C_{2-8}$ alkynyl group" means a straight-chained or branched-chained alkynyl group with 2 to 8 carbons, having a carbon-carbon triple bond at any one or more sites on the alkyl chain. The examples include an ethynyl group, prop-1-yn-1-yl group, prop-2-yn-1-yl group, but-1-yn-1-yl group, but-3-yn-1-yl group, 1-methylprop-2-yn-1-yl group, pent-1-yn-1-yl group, pent-4-yn-1-yl group, hex-1-yn-1-yl group, and hex-5-yn-1-yl group.

Specific examples of a "$C_{1-8}$ alkoxy group" in the present invention include a methoxy group, ethoxy group, n-propoxy group, isopropoxy group, n-butoxy group, isobutoxy group, sec-butoxy group, tert-butoxy group, n-pentoxy group, isopentoxy group, neopentoxy group, 1-methylbutoxy group, 1-ethylpropoxy group, n-hexyloxy group, isohexyloxy group, 3-methylpentoxy group, 2-methylpentoxy group, 1-methylpentoxy group, 3,3-dimethylbutoxy group, 2,2-dimethylbutoxy group, 1,1-dimethylbutoxy group, 1,2-dimethylbutoxy group, 1,3-dimethylbutoxy group, 2,3-dimethylbutoxy group, 1-ethylbutoxy group, and 2-ethylbutoxy group.

In the present invention, a "halo $C_{1-8}$ alkoxy group" means a group wherein the aforementioned halo $C_{1-8}$ alkyl group is bound to an oxygen atom, and the examples include a trifluoromethoxy group, 2-fluoroethoxy group, 2-chloroethoxy group, 2-bromoethoxy group, 3-fluoropropoxy group, 3-chloropropoxy group, 4-fluorobutoxy group, 4-chlorobutoxy group, 2,2,2-trifluoroethoxy group, 3,3,3-trifluoropropoxy group, pentafluoroethoxy group, and 2,2,2-trifluoro-1-(trifluoromethyl)ethoxy group.

In the present invention, a "$C_{6-10}$ aryl group" means a monocyclic or polycyclic aryl group with 6 to 10 carbons. Here, a polycyclic aryl group encompasses partially saturated groups in addition to fully unsaturated groups. The examples include a phenyl group, naphthyl group, azulenyl group, indenyl group, indanyl group, and tetralinyl group. A "$C_{6-10}$ aryl" in the following groups also has the same meaning: "$C_{6-10}$ aryl $C_{1-8}$ alkyl group", "$C_{6-10}$ aryl $C_{2-6}$ alkenyl group", "$C_{6-10}$ aryl $C_{1-8}$ alkoxy group", "$C_{6-10}$ arylcarbonyl group", "$C_{6-10}$ arylthio group", "$C_{6-10}$ arylsulfinyl group", and "$C_{6-10}$ arylsulfonyl group". In addition, the "$C_{6-10}$ aryl" in these groups may have a substituent selected from group A.

In the present invention, examples of a "$C_{1-8}$ acyl group" include a formyl group, acetyl group, propionyl group, butyryl group, isobutyryl group, valeryl group, isovaleryl group, and pivaloyl group.

In the present invention, examples of a "$C_{1-8}$ acyloxy group" include an acetoxy group, propionyloxy group, butyryloxy group, isobutyryloxy group, valeryloxy group, isovaleryloxy group, and pivaloyloxy group.

In the present invention, examples of a "$C_{6-10}$ arylcarbonyl group" include a benzoyl group and naphthoyl group.

In the present invention, a "$C_{6-10}$ aryl $C_{1-8}$ alkyl group" means a group wherein the $C_{6-10}$ aryl group mentioned hereinbelow and the abovementioned $C_{1-8}$ alkyl group are bound. The examples include a benzyl group, phenethyl group, 3-phenyl-n-propyl group, 4-phenyl-n-butyl group, 5-phenyl-n-pentyl group, 8-phenyl-n-octyl group, and naphthylmethyl group.

The examples of a "$C_{3-8}$ cycloalkyl group" in the present invention include a cyclopropyl group, cyclobutyl group, cyclopentyl group, cyclohexyl group, cycloheptyl group, and cyclooctyl group. Preferably, the "$C_{3-8}$ cycloalkyl group" is a "$C_{3-6}$ cycloalkyl group" with 3 to 6 carbons.

In the present invention, a "5- to 11-membered heterocyclic group" means a 5 to 7-membered aromatic heterocycle, saturated heterocycle, unsaturated heterocycle or a condensed heterocycle made by a condensation of the above heterocycles and a benzene ring, wherein the above heterocycles contain 1 to 4 heteroatoms selected from a nitrogen atom, oxygen atom and sulfur atom in addition to a carbon atom, as atoms constituting the ring. The examples include a 2-furyl group, 3-furyl group, 2-thienyl group, 3-thienyl group, pyrrol-1-yl group, pyrrol-2-yl group, pyrrol-3-yl group, pyridin-2-yl group, pyridin-3-yl group, pyridin-4-yl group, pyrazin-2-yl group, pyrazin-3-yl group, pyrimidin-2-yl group, pyrimidin-4-yl group, pyrimidin-5-yl group, pyrimidin-6-yl group, pyridazin-3-yl group, pyridazin-4-yl group, 1,3-benzodioxol-4-yl group, 1,3-benzodioxol-5-yl group, 1,4-benzodioxan-5-yl group, 1,4-benzodioxan-6-yl group, 3,4-dihydro-2H-1,5-benzodioxepin-6-yl group, 3,4-dihydro-2H-1,5-benzodioxepin-7-yl group, 2,3-dihydrobenzofuran-4-yl group, 2,3-dihydrobenzofuran-5-yl group, 2,3-dihydrobenzofuran-6-yl group, 2,3-dihydrobenzofuran-7-yl group, benzofuran-2-yl group, benzofuran-3-yl group, benzofuran-4-yl group, benzofuran-5-yl group, benzofuran-6-yl group, benzofuran-7-yl group, benzothiophen-2-yl group, benzothiophen-3-yl group, benzothiophen-4-yl group, benzothiophen-5-yl group, benzothiophen-6-yl group, benzothiophen-7-yl group, quinoxalin-2-yl group, quinoxalin-5-yl group, quinoxalin-6-yl group, indol-1-yl group, indol-2-yl group, indol-3-yl group, indol-4-yl group, indol-5-yl group, indol-6-yl group, indol-7-yl group, isoindol-1-yl group, isoindol-2-yl group, isoindol-4-yl group, isoindol-5-yl group, isoindol-6-yl group, isoindol-7-yl group, isobenzofuran-1-yl group, isobenzofuran-4-yl group, isobenzofuran-5-yl group, isobenzofuran-6-yl group, isobenzofuran-7-yl group, chromen-2-yl group, chromen-3-yl group, chromen-4-yl group, chromen-5-yl group, chromen-6-yl group, chromen-7-yl group, chromen-8-yl group, imidazol-1-yl group, imidazol-2-yl group, imidazol-4-yl group, imidazol-5-yl group, pyrazol-1-yl group, pyrazol-3-yl group, pyrazol-4-yl group, pyrazol-5-yl group, thiazol-2-yl group, thiazol-4-yl group, thiazol-5-yl group, oxazol-2-yl group, oxazol-4-yl group, oxazol-5-yl group, isoxazol-3-yl group, isoxazol-4-yl group, isoxazol-5-yl group, pyrrolidin-2-yl group, pyrrolidin-3-yl group, benzoimidazol-1-yl group, benzoimidazol-2-yl group, benzoimidazol-4-yl group, benzoimidazol-5-yl group, benzothiazol-2-yl group, benzothiazol-4-yl group, benzothiazol-5-yl group, benzoxazol-2-yl group, benzoxazol-4-yl group, benzoxazol-5-yl group, quinolin-2-yl group, quinolin-3-yl group, quinolin-4-yl group, quinolin-5-yl group, quinolin-6-yl group, quinolin-7-yl group, quinolin-8-yl group, isoquinolin-1-yl group, isoquinolin-3-yl group, isoquinolin-4-yl group, isoquinolin-5-yl group, isoquinolin-6-yl group, isoquinolin-7-yl group, isoquinolin-8-yl group, 1,3,4-thiadiazol-2-yl group, morpholino group, 1,2,3-triazol-1-yl group, 1,2,3-triazol-4-yl group, 1,2,3-triazol-5-yl group, 1,2,4-triazol-1-yl group, 1,2,4-triazol-3-yl group, 1,2,4-triazol-5-yl group, tetrazol-1-yl group, tetrazol-2-yl group, indolin-4-yl group, indolin-5-yl group, indolin-6-yl group, indolin-7-yl group, 1,2,3,4-tetrahydroquinolin-5-yl group, 1,2,3,4-tetrahydroquinolin-6-yl group, 1,2,3,4-tetrahydroquinolin-7-yl group, 1,2,3,4-tetrahydroquinolin-8-yl group, 1,2,3,4-tetrahydroisoquinolin-5-yl group, 1,2,3,4-tetrahydroisoquinolin-6-yl group, 1,2,3,4-tetrahydroisoquinolin-7-yl group, and 1,2,3,4-tetrahydroisoquinolin-8-yl group.

Specific examples of a "mono $C_{1-8}$ alkylamino group" of the present invention include a methylamino group, ethylamino group, n-propylamino group, isopropylamino group, n-butylamino group, sec-butylamino group, tert-butylamino group, n-pentylamino group, isopentylamino group, neopentylamino group, 1-methylbutylamino group, 1-ethylpropylamino group, n-hexylamino group, isohexylamino group, 3-methylpentylamino group, 2-methylpentylamino group, 1-methylpentylamino group, 3,3-dimethylbutylamino group, 2,2-dimethylbutylamino group, 1,1-dimethylbutylamino group, 1,2-dimethylbutylamino group, 1,3-dimethylbutylamino group, 2,3-dimethylbutylamino group, 1-ethylbutylamino group, and 2-ethylbutylamino group.

Specific examples of a "di $C_{1-8}$ alkylamino group" of the present invention include a dimethylamino group, methylethylamino group, diethylamino group, methyl-n-propylamino group, ethyl-n-propylamino group, di-n-propylamino group, methyl isopropylamino group, ethyl isopropylamino group, diisopropylamino group, methyl-n-butylamino group, ethyl-n-butylamino group, n-propyl-n-butylamino group, di-n-butylamino group, di-sec-butylamino group, di-tert-butylamino group, dipentylamino group, and dihexylamino group.

Specific examples of a "$C_{1-8}$ alkylthio group" of the present invention include a methylthio group, ethylthio group, n-propylthio group, isopropylthio group, n-butylthio group, isobutylthio group, sec-butylthio group, tert-butylthio group, n-pentylthio group, isopentylthio group, neopentylthio group, 1-methylbutylthio group, 1-ethylpropylthio group, n-hexylthio group, isohexylthio group, 3-methylpentylthio group, 2-methylpentylthio group, 1-methylpentylthio group, 3,3-dimethylbutylthio group, 2,2-dimethylbutylthio group, 1,1-dimethylbutylthio group, 1,2-dimethylbutylthio group, 1,3-dimethylbutylthio group, 2,3-dimethylbutylthio group, 1-ethylbutylthio group, and 2-ethylbutylthio group.

Specific examples of a "$C_{1-8}$ alkylsulfinyl group" of the present invention include a methylsulfinyl group, ethylsulfinyl group, n-propylsulfinyl group, isopropylsulfinyl group, n-butylsulfinyl group, isobutylsulfinyl group, sec-butylsulfinyl group, tert-butylsulfinyl group, n-pentylsulfinyl group, isopentylsulfinyl group, neopentylsulfinyl group, 1-methylbutylsulfinyl group, 1-ethylpropylsulfinyl group, n-hexylsulfinyl group, isohexylsulfinyl group, 3-methylpentylsulfinyl group, 2-methylpentylsulfinyl group, 1-methylpentylsulfinyl group, 3,3-dimethylbutylsulfinyl group, 2,2-dimethylbutylsulfinyl group, 1,1-dimethylbutylsulfinyl group, 1,2-dimethylbutylsulfinyl group, 1,3-dimethylbutylsulfinyl group, 2,3-dimethylbutylsulfinyl group, 1-ethylbutylsulfinyl group, and 2-ethylbutylsulfinyl group.

Specific examples of a "$C_{1-8}$ alkylsulfonyl group" of the present invention include a methylsulfonyl group, ethylsulfonyl group, n-propylsulfonyl group, isopropylsulfonyl group, n-butylsulfonyl group, isobutylsulfonyl group, sec-butylsulfonyl group, tert-butylsulfonyl group, n-pentylsulfonyl group, isopentylsulfonyl group, neopentylsulfonyl group, 1-methylbutylsulfonyl group, 1-ethylpropylsulfonyl group, n-hexylsulfonyl group, isohexylsulfonyl group, 3-methylpentylsulfonyl group, 2-methylpentylsulfonyl group, 1-methylpentylsulfonyl group, 3,3-dimethylbutylsulfonyl group, 2,2-dimethylbutylsulfonyl group, 1,1-dimethylbutylsulfonyl group, 1,2-dimethylbutylsulfonyl group, 1,3-dimethylbutylsulfonyl group, 2,3-dimethylbutylsulfonyl group, 1-ethylbutylsulfonyl group, and 2-ethylbutylsulfonyl group.

Specific examples of a "$C_{6-10}$ arylthio group" of the present invention include a phenylthio group, naphthylthio group, and azulenylthio group.

Specific examples of a "$C_{6-10}$ arylsulfinyl group" of the present invention include a benzenesulfinyl group, p-toluenesulfinyl group, p-chlorobenzenesulfinyl group, naphthalen-1-ylsulfinyl group, and naphthalen-2-ylsulfinyl group.

Specific examples of a "$C_{6-10}$ arylsulfonyl group" of the present invention include a benzenesulfonyl group, p-toluenesulfonyl group, p-chlorobenzenesulfonyl group, naphthalen-1-ylsulfonyl group, and naphthalen-2-ylsulfonyl group.

Specific examples of a "$C_{1-8}$ alkoxycarbonyl group" of the present invention include a methoxycarbonyl group, ethoxycarbonyl group, n-propoxycarbonyl group, isopropoxycarbonyl group, n-butoxycarbonyl group, isobutoxycarbonyl group, sec-butoxycarbonyl group, tert-butoxycarbonyl group, n-pentoxycarbonyl group, isopentoxycarbonyl group, neopentoxycarbonyl group, 1-methylbutoxycarbonyl group, 1-ethylpropoxycarbonyl group, n-hexyloxycarbonyl group, isohexyloxycarbonyl group, 3-methylpentoxycarbonyl group, 2-methylpentoxycarbonyl group, 1-methylpentoxycarbonyl group, 3,3-dimethylbutoxycarbonyl group, 2,2-dimethylbutoxycarbonyl group, 1,1-dimethylbutoxycarbonyl group, 1,2-dimethylbutoxycarbonyl group, 1,3-dimethylbutoxycarbonyl group, 2,3-dimethylbutoxycarbonyl group, 1-ethylbutoxycarbonyl group, and 2-ethylbutoxycarbonyl group.

In the present invention, a "$C_{3-8}$ cycloalkenyl group" means a group having a carbon-carbon double bond at any one or more sites on the carbocycle of the above "$C_{3-8}$ cycloalkyl group", and the examples include a cyclopropenyl group, cyclobutenyl group, 2-cyclopenten-1-yl group, 3-cyclopenten-1-yl group, 2-cyclohexen-1-yl group, 3-cyclohexen-1-yl group, 2-cyclohepten-1-yl group, 3-cyclohepten-1-yl group, 4-cyclohepten-1-yl group, 2-cycloocten-1-yl group, 3-cycloocten-1-yl group, 4-cycloocten-1-yl group, and cyclohexadienyl group.

In the present invention, a "5- to 7-membered carbocycle" means a hydrocarbon ring with 5 to 7 carbons, and the examples include a cyclopentyl group, cyclohexyl group, and cycloheptyl group.

In the present invention, a "$C_{3-8}$ cycloalkyl $C_{1-8}$ alkyl group" means a group wherein the above "$C_{3-8}$ cycloalkyl group" is bound to a $C_{1-8}$ alkyl group, and the examples include a cyclopropylmethyl group, cyclobutylmethyl group, cyclopentylmethyl group, and cyclohexylmethyl group.

In the present invention, a "$C_{3-8}$ cycloalkyl $C_{2-8}$ alkenyl group" means a group wherein the above "$C_{3-8}$ cycloalkyl group" is bound to a $C_{2-8}$ alkenyl group, and the examples include a 2-cyclopropylethen-1-yl group, 2-cyclobutylethen-1-yl group, 2-cyclopentylethen-1-yl group, and 2-cyclohexylethen-1-yl group.

In the present invention, a "$C_{3-8}$ cycloalkyl $C_{2-8}$ alkynyl group" means a group wherein the above "$C_{3-8}$ cycloalkyl group" is bound to a $C_{2-8}$ alkynyl group, and the examples include a 2-cyclopropylethynyl group, 2-cyclobutylethynyl group, 2-cyclopentylethynyl group, and 2-cyclohexylethynyl group.

In the present invention, a "$C_{6-10}$ aryl $C_{1-8}$ alkyl group" means a group wherein the above "$C_{6-10}$ aryl group" is bound to a $C_{1-8}$ alkyl group, and the examples include a benzyl group, phenethyl group, and naphthylmethyl group.

In the present invention, a "$C_{6-10}$ aryl $C_{2-8}$ alkenyl group" means a group wherein the above "$C_{6-10}$ aryl group" is bound to a $C_{2-8}$ alkenyl group, and the examples include a styryl group, cinnamyl group, 4-phenyl-3-buten-1-yl group, 5-phenyl-4-penten-1-yl group, and 6-phenyl-6-hexen-1-yl group.

In the present invention, a "$C_{6-10}$ aryl $C_{1-8}$ alkoxy group" means a group wherein the above "$C_{6-10}$ aryl $C_{1-8}$ alkyl group" is bound to an oxygen atom, and the examples include a benzyloxy group, phenethyloxy group, and naphthylmethyloxy group.

In the present invention, a "$C_{1-8}$ alkyl chain" means a divalent hydrocarbon chain with 1 to 8 carbons having a straight-chain or a branch, and the examples include a methylene chain, ethylene chain, trimethylene chain, methylethylene chain, tetramethylene chain, 1,2-dimethylethylene chain, pentamethylene chain, 1-methyltetramethylene chain, 2-methyltetramethylene chain, hexamethylene chain, heptamethylene chain, and octamethylene chain.

In the present invention, a "$C_{2-8}$ alkenyl chain" means, among the above "$C_{1-8}$ alkyl chains", a straight-chained or branched-chained divalent hydrocarbon chain with 2 to 8 carbons having a carbon-carbon double bond at any one or more sites on the above $C_{2-8}$ alkyl chain. The examples include a vinylene chain, propenylene chain, methylvinylene chain, butenylene chain (for example, 1-butenylene chain, 2-butenylene chain or the like), 1,2-dimethylvinylene chain, pentenylene chain, 1-methylbutenylene chain, 2-methylbutenylene chain, hexenylene chain, heptenylene chain, octenylene chain, and isoprene chain.

In the present invention a "$C_{6-10}$ aryl chain" means a divalent aromatic hydrocarbon-ring group, and the examples include an o-phenylene chain, m-phenylene chain, and p-phenylene chain.

In the present invention, a "5- to 11-membered heteroarylene chain" means a divalent group which is a 5- to 7-membered aromatic heterocycle, saturated heterocycle, unsaturated heterocycle or a condensed heterocycle made by a condensation of the above heterocycles and a benzene ring, wherein the above heterocycles contain 1 to 4 heteroatoms selected from a nitrogen atom, oxygen atom and sulfur atom in addition to a carbon atom, as atoms constituting the ring. The examples include a 2,3-furandiyl chain, 2,3-thiophenediyl chain, 2,3-pyrrolediyl chain, 2,3-pyridinediyl chain, 2,4-pyridinediyl chain, 2,3-pyrazinediyl chain, 2,4-pyrimidinediyl chain, 3,4-pyridazinediyl chain, 2,3-benzofurandiyl chain, 2,3-benzothiophenediyl chain, quinoxalin-2-yl chain, quinoxalin-5-yl chain, 2,3-quinoxalinediyl chain, 2,3-indolediyl chain, indol-7-yl chain, 1,3-isoindolediyl chain, 1,3-isobenzofurandiyl chain, 2,4-chromenediyl chain, 2,4-imidazolediyl chain, 3,4-pyrazolediyl chain, 2,4-thiazolediyl chain, 2,4-oxazole diyl chain, 3,4-isoxazolediyl chain, 2,4-benzoimidazolediyl chain, 2,4-benzothiazolediyl chain, 2,4-benzoxazolediyl chain, 2,4-quinolinediyl chain, and 1,4-isoquinolinediyl chain.

Other groups that are not defined herein follow common definitions.

Followings are examples of the preferred modes of the present invention.

In general formula (1), $R^1$ is preferably a $C_{1-8}$ alkyl group or $C_{6-10}$ aryl $C_{1-8}$ alkyl group.

In general formula (1), the $C_{1-8}$ alkyl group of $R^1$ is preferably a straight-chained $C_{1-8}$ alkyl group, more preferably a straight-chained $C_{1-6}$ alkyl group such as a methyl group, ethyl group, n-propyl group, or n-butyl group, and particularly preferably an n-propyl group.

In general formula (1), the $C_{6-10}$ aryl $C_{1-8}$ alkyl group of $R^1$ is preferably a benzyl group.

In general formula (1), $R^2$ is preferably a halo $C_{1-8}$ alkyl group, more preferably a 2,2,2-trifluoroethyl group or trifluoromethyl group, and particularly preferably a trifluoromethyl group.

In general formula (1), $R^3$, $R^4$, $R^5$, and $R^6$ are preferably a hydrogen atom.

In general formula (1), $R^7$ and $R^8$ are preferably a $C_{1-8}$ alkyl group, $C_{6-10}$ aryl group, or a 5- to 11-membered heterocyclic group.

In general formula (1), the $C_{1-8}$ alkyl group of $R^7$ and $R^8$ are preferably a straight-chained $C_{1-8}$ alkyl group, more preferably a straight-chained $C_{1-6}$ alkyl group such as a methyl group, ethyl group, n-propyl group, or n-butyl group, and particularly preferably a methyl group or ethyl group.

In general formula (1), the $C_{6-10}$ aryl group of $R^7$ and $R^8$ is preferably a phenyl group. The phenyl group may have a substituent, and the substituent is preferably a halogen atom such as a fluorine atom, a $C_{1-8}$ alkyl group such as an isopropyl group, and a $C_{1-8}$ alkoxy group such as an isopropoxy group.

In general formula (1), a 5- to 11-membered heterocyclic group of $R^7$ and $R^8$ is preferably a 5 to 7-membered aromatic heterocycle, unsaturated heterocycle or a condensed heterocycle made by a condensation of the above heterocycles and a benzene ring, wherein the above heterocycles contain 1 or 2 heteroatoms selected from a nitrogen atom and oxygen atom in addition to a carbon atom, as atoms constituting the ring. The examples include a pyridyl group, 1,3-benzodioxonyl group, 1,4-benzodioxanyl group, 2,3-dihydrobenzofuranyl group, or quinoxalinyl group. These 5- to 11-membered heterocyclic groups may have a substituent, and the substituent is preferably a $C_{1-8}$ alkoxy group such as a methoxy group, ethoxy group, n-propoxy group, and isopropoxy group.

In a preferred combination of $R^7$ and $R^8$ of general formula (1), either one of the $R^7$ and $R^8$ is a $C_{1-8}$ alkyl group and the other is a $C_{6-10}$ aryl group or 5- to 11-membered heterocyclic group.

In general formula (1), $R^9$ is preferably a hydrogen atom.

In general formula (1), X is preferably a bond, $C_{1-8}$ alkyl chain, or $C_{6-10}$ aryl chain. The $C_{1-8}$ alkyl chain is preferably an ethylene chain, and the $C_{6-10}$ aryl chain is preferably a phenylene chain, and particularly more preferably an m-phenylene chain or p-phenylene chain.

In general formula (1), Y is preferably a —O—.

In general formula (1), L is preferably a "$C_{1-8}$ alkyl chain", more preferably a "$C_{1-6}$ alkyl chain", and particularly preferably an ethylene chain, trimethylene chain, tetramethylene chain, pentamethylene chain, or hexamethylene chain.

The following example can be given as a more preferred embodiment of the present invention.

A combination wherein, in general formula (1), $R^1$ is a $C_{1-8}$ alkyl group or $C_{6-10}$ aryl $C_{1-8}$ alkyl group, $R^2$ is a halo $C_{1-8}$ alkyl group, either one of $R^7$ and $R^8$ is a $C_{1-8}$ alkyl group and the other is a $C_{6-10}$ aryl group or 5- to 11-membered heterocyclic group, Y is a —O—, and L is a $C_{1-8}$ alkyl chain.

Examples of an addition salt of a quinoline compound represented by general formula (1) include alkali metal salts such as sodium salt and potassium salt; alkaline earth metal salts such as calcium salt and magnesium salt; organic base salts such as ammonium salt and trialkylamine salt; mineral acid salts such as hydrochloride salt and sulfate; and organic acid salts such as acetate. There is no particular limitation as long as it is a pharmaceutically acceptable salt.

Examples of a solvate of a quinoline compound represented by general formula (1) include a hydrate.

When there is a geometric isomer or optical isomer of a compound of the present invention, such isomers are included in the scope of the present invention.

Compound (I) can be produced by various known methods without particular limitation, and for example, can be produced according to the following reaction process.

More specifically, by reacting a quinoline derivative shown by general formula (II) with a dihalide (III), a derivative shown by general formula (IV) is obtained. By reacting the obtained compound shown by general formula (IV) with an imide compound shown by general formula (V), a compound (I) can be produced. This reaction path shown by a chemical reaction formula is as follows:

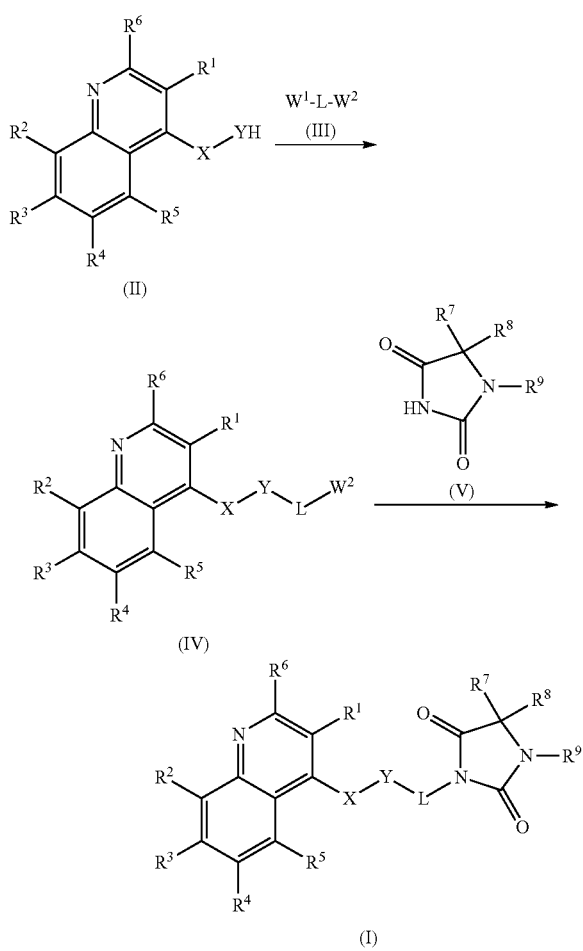

(wherein $R^1$ to $R^9$, X, Y, and L have the same meaning as above and $W^1$ and $W^2$ show a halogen atom).

If an imide compound shown by general formula (V) has a reactive substituent, a compound of interest can be obtained by an addition of a protective group by a commonly used method (Protective Groups in Organic Synthesis Third Edition: John Wiley & Sons, Inc; 1999) followed by a deprotection at an appropriate time.

By reacting a quinoline derivative shown by general formula (II) with excessive amounts of dihalide (III) in a solvent in the presence or absence of a base, a derivative of general formula (IV) which is a substance of interest can be obtained. The solvent is not particularly limited, and for example, the followings can be used independently or in combination: tetrahydrofuran, toluene, dioxane, N,N-dimethylformamide, N-methylpyrrolidone, dimethylsulfoxide, acetonitrile, propionitrile, acetone, methylethyl ketone, or water. Further, a dihalide (III) can be used as a solvent. The base is not particularly limited, and for example, the followings can be used: alkali metal hydrides such as lithium hydride, sodium hydride, and potassium hydride; alkali metal hydroxides such as lithium hydroxide, sodium hydroxide, and potassium hydroxide; alkali metal carbonates such as lithium carbonate, sodium carbonate, potassium carbonate, and cesium carbonate; alcohol metallic salts such as sodium methoxide, potassium methoxide, sodium ethoxide, sodium t-butoxide, and potassium t-butoxide; lithium diisopropylamide, sodium diisopropylamide, potassium diisopropylamide, lithium hexamethyldisilazide, sodium hexamethyldisilazide, potassium hexamethyldisilazide, n-butyllithium, s-butyllithium, or t-butyllithium. A derivative of general formula (IV) which is a substance of interest can be obtained by conducting a reaction under the reaction conditions of −80 to 150° C., preferably of 0 to 100° C., for 1 minute to 5 days, preferably for 1 hour to 3 days.

By reacting the halide derivative (IV) obtained from the above reaction with an imide compound (V) in a solvent in the presence or absence of a base, a substance of interest (I) can be produced. The solvent is not particularly limited, and for example, the followings can be used independently or in combination: tetrahydrofuran, toluene, dioxane, N,N-dimethylformamide, N-methylpyrrolidone, dimethylsulfoxide, acetonitrile, propionitrile, acetone, methylethyl ketone, or water. The base is not particularly limited, and for example, the followings can be used: alkali metal hydrides such as lithium hydride, sodium hydride, and potassium hydride; alkali metal hydroxides such as lithium hydroxide, sodium hydroxide, and potassium hydroxide; alkali metal carbonates such as lithium carbonate, sodium carbonate, potassium carbonate, and cesium carbonate; alcohol metallic salts such as sodium methoxide, potassium methoxide, sodium ethoxide, potassium ethoxide, sodium t-butoxide, and potassium t-butoxide; lithium diisopropylamide, sodium diisopropylamide, potassium diisopropylamide, lithium hexamethyldisilazide, sodium hexamethyldisilazide, potassium hexamethyldisilazide, n-butyllithium, s-butyllithium, or t-butyllithium. A substance of interest can be obtained by conducting a reaction under the reaction conditions of −80 to 150° C., preferably of 0 to 100° C., for 1 minute to 5 days, preferably for 1 hour to 3 days.

Further, a compound (I) can also be produced by reacting an imide compound shown by the above general formula (V) with a reagent shown by general formula (VI) to obtain an intermediate (VII), and then by further reacting with a quinoline derivative (II). This reaction path shown by a chemical reaction formula is as follows:

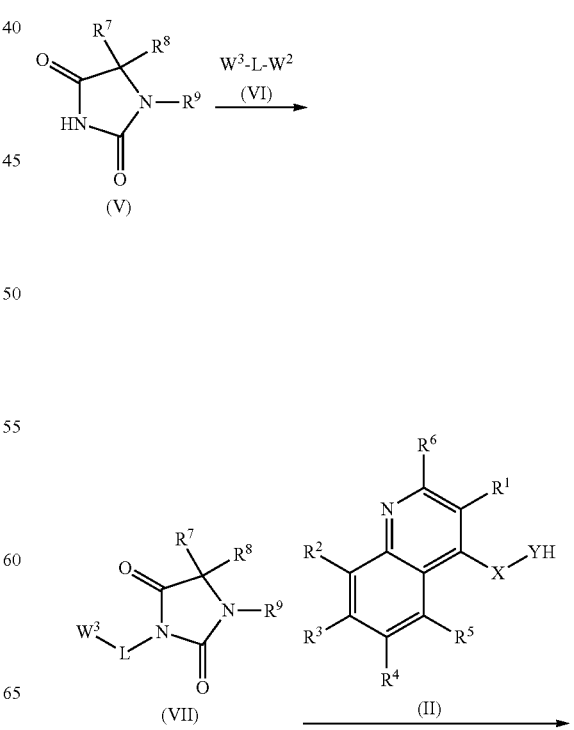

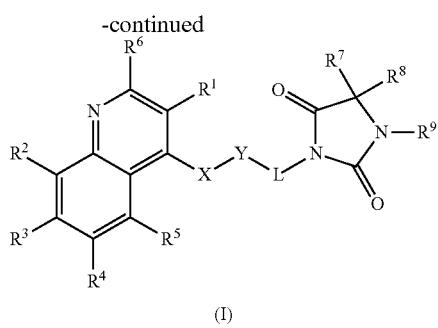

(I)

(wherein $R^1$ to $R^9$, X, and L have the same meaning as above, $W^2$ shows a halogen atom, and $W^3$ shows a halogen atom, aldehyde, or aldehyde equivalent).

The term an "aldehyde equivalent" refers to an aldehyde added with a protective group or to a substance that can be transformed into an aldehyde by a commonly used method (Comprehensive Organic Transformations Second Edition: John Wiley & Sons, Inc; 1999). A commonly used protective group (Protective Groups in Organic Synthesis Third Edition: John Wiley & Sons, Inc; 1999) can be used.

If a cyclic amide compound shown by general formula (V) has a reactive substituent, a compound of interest can be obtained by an addition of a protective group by a commonly used method (Protective Groups in Organic Synthesis Third Edition: John Wiley & Sons, Inc; 1999), followed by a deprotection at an appropriate time.

By reacting a cyclic amide compound shown by general formula (V) with a reagent shown by general formula (VI) in a solvent in the presence or absence of a base, a derivative of general formula (VII) which is a substance of interest can be obtained. The solvent is not particularly limited, and for example, the followings can be used independently or in combination: tetrahydrofuran, toluene, dioxane, N,N-dimethylformamide, N-methylpyrrolidone, dimethylsulfoxide, acetonitrile, propionitrile, acetone, methylethyl ketone, or water. The base is not particularly limited, and for example, the followings can be used: alkali metal hydrides such as lithium hydride, sodium hydride, and potassium hydride; alkali metal hydroxides such as lithium hydroxide, sodium hydroxide, and potassium hydroxide; alkali metal carbonates such as lithium carbonate, sodium carbonate, potassium carbonate, and cesium carbonate; alcohol metallic salts such as sodium methoxide, potassium methoxide, sodium ethoxide, potassium ethoxide, sodium t-butoxide, and potassium t-butoxide; lithium diisopropylamide, sodium diisopropylamide, potassium diisopropylamide, lithium hexamethyldisilazide, sodium hexamethyldisilazide, potassium hexamethyldisilazide, n-butyllithium, s-butyllithium, or t-butyllithium. A derivative of general formula (VII) which is the substance of interest can be obtained by conducting a reaction under the reaction conditions of −80 to 150° C., preferably of 0 to 100° C., for 1 minute to 5 days, preferably for 1 hour to 3 days.

When $W^3$ is a halogen atom, a compound (I) can be produced by the same alkylation reaction as mentioned above.

Further, when Y shows a —N($R^{10}$)—, a compound (I) can be produced using a reductive alkylation reaction with the use of a reagent shown by general formula (VII) in which $W^3$ is an aldehyde group. A reductive alkylation reaction can be conducted by a commonly used method (Comprehensive Organic Transformations Second Edition: John Wiley & Sons, Inc; 1999).

A known method (Chem. Revs. 30, pp 113-144 (1942), Chem. Revs. 35, pp-77-277 (1944)) can be referred to for a common method for producing a quinoline derivative.

A 4-substituted-quinoline derivative shown by general formula (II) can be produced by a known method (Chem. Revs. 43, pp 43-68 (1948), J. Am. Chem. Soc., 70, pp-2402-2404 (1948)).

A quinoline compound represented by general formula (1) of the present invention can be obtained by the above-mentioned methods, and further and optionally, can be purified using an ordinary purifying method such as recrystallization method and column chromatography. Moreover, the above compound can optionally be processed into an above-mentioned desired salt or solvate by a usual method.

So obtained quinoline compound represented by general formula (1) or salt thereof, or their solvate (hereinafter, sometimes collectively described as "compounds represented by general formula (1)") shows a superior LXRβ agonist effect as shown in test examples described hereinbelow, and is useful as an active ingredient of a preventative and/or therapeutic agent for diseases of animal including humans, resulting from abnormal cholesterol metabolism, for example, atherosclerosis; arteriosclerosis such as those resulting from diabetes; dyslipidemia; hypercholesterolemia; lipid-related diseases; inflammatory diseases that are caused by inflammatory cytokines; skin diseases such as allergic skin diseases; diabetes; or Alzheimer's disease.

The pharmaceutical composition of the present invention contains a quinoline compound represented by general formula (1) or salt thereof, or their solvate. The pharmaceutical composition may be used independently, but generally, is used by formulating with a pharmaceutically acceptable carrier, additive and the like. The administration form of the pharmaceutical composition is not particularly limited, and can be selected as desired according to the therapeutic purpose. For example, the administration form can be any of oral preparation, injection, suppository, ointment, inhalation, eyedrops, nasal preparation, adhesive patch and the like. The pharmaceutical composition suitable for these administration forms can be produced according to a known method of drug formulation.

When prepared into a solid oral formulation, a compound represented by general formula (1) can be added with an excipient and optionally, further with a binder, disintegrant, lubricant, coloring agent, flavoring agent, odor improving agent or the like, and then processed into a tablet, coated tablet, granules, powder, capsule or the like by a usual method. The additive may be those commonly used in this field. Examples of the excipient include lactose, sucrose, sodium chloride, glucose, starch, calcium carbonate, Kaolin, microcrystalline cellulose, and silicate. Examples of the binder include water, ethanol, propanol, simple syrup, dextrose solution, starch solution, gelatin solution, carboxymethylcellulose, hydroxypropylcellulose, hydroxypropyl starch, methylcellulose, ethylcellulose, shellack, calcium phosphate, and polyvinylpyrrolidone. Examples of the disintegrant include dry starch, sodium alginate, powdered agar, sodium hydrogen carbonate, calcium carbonate, sodium lauryl sulfate, monoglyceride stearate, and lactose. Examples of the lubricant include purified talc, stearate, borax, polyethyleneglycol and the like. Examples of the flavoring agent include sucrose, orange peel, citric acid, and tartaric acid.

When prepared into a liquid oral formulation, a compound represented by general formula (1) can be added with a flavoring agent, buffer, stabilizer, odor improving agent or the like, and then processed into an internal liquid formulation, syrup, elixir or the like. The flavoring agent may be those mentioned above, and examples of the buffer include sodium citrate, and examples of the stabilizer include tragacanth, gum Arabic, and gelatin.

When prepared into an injection, a compound represented by general formula (1) can be added with a pH adjuster, buffer, stabilizer, isotonic agent, local anesthetic or the like, and then processed into a subcutaneous, intramuscular, and intravenous injection by a usual method. Examples of the pH adjuster and buffer include sodium citrate, sodium acetate, and sodium phosphate. Examples of the stabilizer include sodium pyrosulfite, EDTA, thioglycolic acid, and thiolactic acid. Examples of the local anesthetic include procaine hydrochloride and lidocaine hydrochloride. Examples of the isotonic agent include sodium chloride and glucose.

When prepared into a suppository, a compound represented by general formula (1) can be added with a known carrier for suppository, for example, with polyethyleneglycol, lanolin, cacao butter, or fatty acid triglyceride, and optionally, further with a surfactant such as Tween®, and then processed into a suppository by a usual method.

When prepared into an ointment, a compound represented by general formula (1) can be optionally formulated with a commonly used base, stabilizer, moisturizer, preservative or the like, and then mixed and formulated by a usual method. Examples of the base include liquid paraffin, white petrolatum, white beeswax, octyldodecyl alcohol, and paraffin. Examples of the preservative include methyl p-hydroxybenzoate, ethyl p-hydroxybenzoate, and propyl p-hydroxybenzoate.

In addition to the above, a compound represented by general formula (1) can be processed into an inhalation, eyedrops, or nasal preparation by a usual method.

The dose of a compound represented by general formula (1) varies depending on the age, weight, symptom, administration form, the number of doses and the like, but generally, it is preferable to administer a quinoline compound represented by general formula (1) to an adult in an amount of 1 to 1000 mg per day as a single or several separate doses either orally or parenterally.

EXAMPLE

The present invention will be described further with reference to the following examples, while the scope of the present invention will not be limited to these examples.

Example 1

Preparation of 5-(benzo[d][1,3]dioxol-5-yl)-3-{6-[3-benzyl-8-(trifluoromethyl)quinolin-4-yloxy]hexyl}-5-methylimidazolidine-2,4-dione

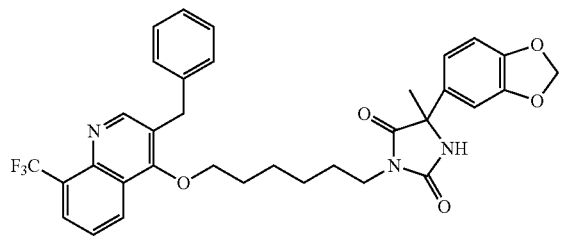

a) Preparation of ethyl 2-benzoyl-3-ethoxyacrylate

Ethyl benzoylacetate (17.0 g, 88.4 mmol) and ethyl orthoformate (106 mL, 637 mmol) were dissolved in acetic anhydride (60.2 mL, 637 mmol) and stirred at 140° C. overnight. The reaction solution was returned to room temperature, then added with water and extracted with ethyl acetate. The organic layer was washed with saturated saline, dried using anhydrous sodium sulfate, and concentrated in vacuo. The obtained residue was purified using silica-gel column chromatography (hexane/ethyl acetate) and the title compound (20.7 g, yield 94%) was obtained as an orange oil.

$^1$H-NMR (CDCl$_3$) δ: 1.14 (3H, t, J=7.1 Hz), 1.26 (3H, t, J=7.1 Hz), 4.10 (2H, q, J=7.1 Hz), 4.15 (2H, q, J=7.1 Hz), 7.43-7.46 (2H, m), 7.53-7.58 (1H, m), 7.71 (1H, s), 7.88-7.91 (2H, m).

b) Preparation of ethyl 2-benzoyl-3-[2-(trifluoromethyl)phenylamino]acrylate (cis:trans=1:1)

To a solution of ethyl 2-benzoyl-3-ethoxyacrylate (3.70 g, 14.9 mmol) in toluene (14.9 mL), 2-trifluoromethylaniline (2.06 mL, 16.4 mmol) was added. After irradiated at 150° C. for 1 hour using a microwave (Biotage® initiator), the reaction solution was concentrated in vacuo. The title compound (5.41 g, yield 99%) was obtained as a cis/trans mixture (1:1) as an orange oil.

$^1$H-NMR (cis/trans mixture (1:1) CDCl$_3$) δ: 0.94-0.99 (3H, m), 4.02-4.14 (2H, m), 7.17-7.70 (9H, m), 8.22 (0.5H, d, J=12.7 Hz), 8.47 (0.5H, d, J=12.7 Hz), 11.25 (0.5H, brd, J=12.7 Hz), 12.44 (0.5H, brd, J=12.7 Hz).

c) Preparation of [4-hydroxy-8-(trifluoromethyl)quinolin-3-yl](phenyl)methanone

A solution of ethyl 2-benzoyl-3-[2-(trifluoromethyl)phenylamino]acrylate (30.5 g, 84.0 mmol) in Dowtherm® (280 mL) was stirred at 260° C. for 11 hours. The reaction solution was returned to room temperature, then added with hexane and recrystallized. The title compound (17.0 g, yield 64%) was obtained as a brown oil.

$^1$H-NMR (CDCl$_3$) δ: 7.43-8.26 (7H, m), 8.64-8.67 (1H, m), 9.18 (1H, s), 14.23 (1H, s).

d) Preparation of 3-benzyl-8-(trifluoromethyl)quinolin-4-ol

To a solution of [4-hydroxy-8-(trifluoromethyl)quinolin-3-yl](phenyl)methanone (17.0 g, 53.7 mmol) in tetrahydrofuran (270 mL), aluminum chloride (35.1 g, 263 mmol) and sodium borohydride (5.49 g, 145 mmol) were added at 0° C., stirred at room temperature for 30 minutes, and then refluxed for 5 hours. The reaction solution was brought to 0° C., added with water, and extracted with ethyl acetate. Subsequently, the organic layer was washed with brine, dried using anhydrous sodium sulfate, and concentrated in vacuo. The obtained residue was recrystallized with ethyl acetate, and the title compound (11.7 g, yield 72%) was obtained as a colorless crystal.

$^1$H-NMR (CDCl$_3$) δ: 3.92 (2H, s), 7.21-7.42 (7H, m), 7.89 (1H, d, J=7.3 Hz), 8.41 (1H, brs), 8.66 (1H, d, J=8.0 Hz).

e) Preparation of 3-benzyl-4-(6-bromohexyloxy)-8-(trifluoromethyl)quinoline

A DMF (3 mL) solution of 3-benzyl-8-(trifluoromethyl)quinolin-4-ol (500 mg, 1.65 mmol), 1,6-dibromohexane (3.22 g, 13.20 mmol), and potassium carbonate (455.7 mg, 3.30 mmol) was stirred at room temperature overnight. The reaction solution was added with water and extracted with ethyl acetate. Subsequently, the organic layer was washed with brine, dried using anhydrous sodium sulfate, and concentrated in vacuo. The obtained residue was purified using silica-gel column chromatography (hexane:ethyl acetate), and the title compound (660 mg, yield 86%) was obtained as a colorless oil.

$^1$H-NMR (CDCl$_3$) δ: 1.51-1.58 (4H, m), 1.91 (4H, quintet, J=6.6 Hz), 3.43 (2H, t, J=6.6 Hz), 3.99 (2H, t, J=6.6 Hz), 4.21 (2H, s), 7.17-7.33 (5H, m), 7.59 (1H, dd, J=6.6, 7.6 Hz), 8.04 (1H, d, J=6.6 Hz), 8.28 (1H, d, J=7.6 Hz), 8.27 (1H, s).

f) Preparation of 5-(benzo[d][1,3]dioxol-5-yl)-3-{6-[3-benzyl-8-(trifluoromet hyl)quinolin-4-yloxy]hexyl}-5-methylimidazolidine-2,4-dione A DMF (0.1 mL) solution of 3-benzyl-4-(6-bromohexyloxy)-8-(trifluoromethyl)quinoline (12.5 mg, 0.03 mmol) was added with potassium carbonate (9 mg, 0.06 mmol) and 5-(benzo[d][1,3]dioxol-5-yl)-5-methylimidazolidine-2,4-dione (46.8 mg, 0.20 mmol), and stirred overnight. The reaction solution was added with water, extracted with ethyl acetate, subsequently dried using anhydrous sodium sulfate and concentrated in vacuo. The obtained residue was purified using silica-gel column chromatography (hexane:ethyl acetate), and the title compound (22.5 mg, yield 49%) was obtained as a colorless oil.

$^1$H-NMR (CDCl$_3$) δ: 1.37 (2H, tt, J=6.3, 7.9 Hz), 1.53 (2H, tt, J=6.3, 7.3 Hz), 1.63 (2H, tt, J 7.3, 7.9 Hz), 1.79 (3H, s), 1.86 (2H, tt, J=6.6, 7.3 Hz), 3.52 (2H, t, J=7.3 Hz), 3.95 (2H, t, J=6.6 Hz), 4.19 (2H, s), 5.79 (1H, s), 5.94 (2H, s), 6.78 (1H, d, J=8.2 Hz), 6.92 (1H, dd, J=2.0, 8.2 Hz), 6.96 (1H, d, J=2.0 Hz), 7.18-7.31 (5H, m), 7.58 (1H, dd, J=6.9, 7.6 Hz), 8.03 (1H, d, J=6.9 Hz), 8.26 (1H, d, J=7.6 Hz), 8.86 (1H, s).

Example 2

Preparation of 5-(benzo[d][1,3]dioxol-5-yl)-3-{6-[3-benzyl-8-(trifluoromethyl)quinolin-4-yloxy]hexyl}-5-ethylimidazolidine-2,4-dione

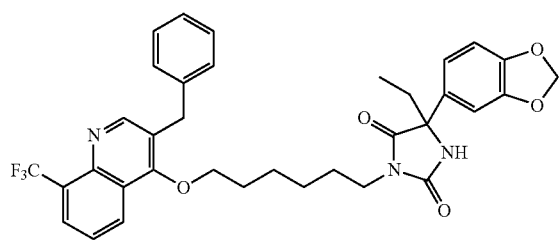

5-(benzo[d][1,3]dioxol-5-yl)-5-ethylimidazolidine-2,4-dione was used in place of 5-(benzo[d][1,3]dioxol-5-yl)-5-methylimidazolidine-2,4-dione of Example 1f) for a similar reaction and treatment, and the title compound was obtained as a colorless oil.

$^1$H-NMR (CDCl$_3$) δ: 0.89 (3H, t, J=7.3 Hz), 1.36 (2H, tt, J=6.9, 7.5 Hz), 1.52 (2H, tt, J=6.9, 7.3 Hz), 1.64 (2H, tt, J=7.3, 7.5 Hz), 1.84 (2H, tt, J=6.6, 7.3 Hz), 2.06 (1H, qd, J=7.3, 14.2 Hz), 2.19 (1H, qd, J=7.3, 14.2 Hz), 3.50 (2H, t, J=7.3 Hz), 3.94 (2H, t, J=6.6 Hz), 4.18 (2H, s), 5.93 (1H, d, J=1.3 Hz), 5.94 (1H, d, J=1.3 Hz), 6.14 (1H, s), 6.78 (1H, d, J=8.2 Hz), 6.94 (1H, dd, J=2.0, 8.2 Hz), 7.03 (1H, d, J=2.0 Hz), 7.17-7.31 (5H, m), 7.58 (1H, dd, J=6.9, 7.3 Hz), 8.03 (1H, d, J=6.9 Hz), 8.25 (1H, d, J=7.3 Hz), 8.85 (1H, s).

Example 3

Preparation of 3-{6-[3-benzyl-8-(trifluoromethyl)quinolin-4-yloxy]hexyl}-5-(2,3-dihydrobenzo[b][1,4]dioxin-6-yl)-5-methylimidazolidine-2,4-dione

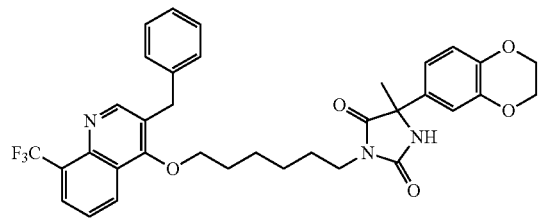

5-(2,3-dihydrobenzo[b][1,4]dioxin-6-yl)-5-methylimidazolidine-2,4-dione was used in place of 5-(benzo[d][1,3]dioxol-5-yl)-5-methylimidazolidine-2,4-dione of Example 1f) for a similar reaction and treatment, and the title compound was obtained as a colorless oil.

$^1$H-NMR (CDCl$_3$) δ: 1.28-1.41 (2H, m), 1.46-1.60 (2H, m), 1.67 (2H, quintet, J=7.6 Hz), 1.77 (3H, s), 1.82 (2H, quintet, J=6.6 Hz), 3.51 (2H, t, J=7.3 Hz), 3.95 (2H, t, J=6.3 Hz), 4.18 (2H, s), 4.21 (4H, s), 5.70 (1H, s), 6.85 (1H, d, J=8.2 Hz), 6.91 (1H, dd, J=2.3, 8.2 Hz), 6.97 (1H, d, J=2.3 Hz), 7.17-7.31 (5H, m), 7.58 (1H, dd, J=7.3, 8.2 Hz), 8.02 (1H, d, J=7.3 Hz), 8.26 (1H, d, J=8.2 Hz), 8.85 (1H, s).

Example 4

Preparation of 3-{6-[3-benzyl-8-(trifluoromethyl)quinolin-4-yloxy]hexyl}-5-(2,3-dihydrobenzo[b][1,4]dioxin-6-yl)-5-ethylimidazolidine-2,4-dione

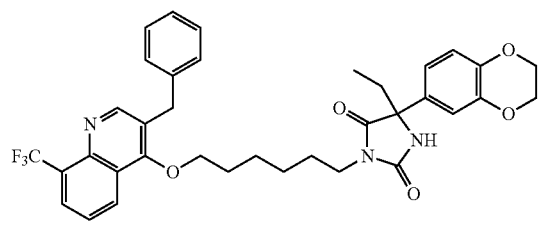

5-(2,3-dihydrobenzo[b][1,4]dioxin-6-yl)-5-ethylimidazolidine-2,4-dione was used in place of 5-(benzo[d][1,3]dioxol-5-yl)-5-methylimidazolidine-2,4-dione of Example 1f) for a similar reaction and treatment, and the title compound was obtained as a colorless oil.

$^1$H-NMR (CDCl$_3$) δ: 0.89 (3H, t, J=7.3 Hz), 1.31-1.42 (2H, m), 1.45-1.64 (4H, m), 1.84 (2H, tt, J=6.6, 7.3 Hz), 2.04 (1H, qd, J=7.3, 14.5 Hz), 2.20 (1H, qd, J=7.3, 14.5 Hz), 3.50 (2H, t, J=7.3 Hz), 3.94 (2H, t, J=6.6 Hz), 4.19 (2H, s), 4.22 (4H, s), 5.77 (1H, s), 6.85 (1H, d, J=8.6 Hz), 6.93 (1H, dd, J=2.3, 8.6 Hz), 7.02 (1H, d, J=2.3 Hz), 7.17-7.32 (5H, m), 7.59 (1H, dd, J=7.3, 7.9 Hz), 8.03 (1H, d, J=7.3 Hz), 8.26 (1H, d, J=8.9 Hz), 8.86 (1H, s).

Example 5

Preparation of 3-{6-[3-benzyl-8-(trifluoromethyl)quinolin-4-yloxy]hexyl}-5-(2,3-dihydrobenzofuran-5-yl)-5-methylimidazolidine-2,4-dione

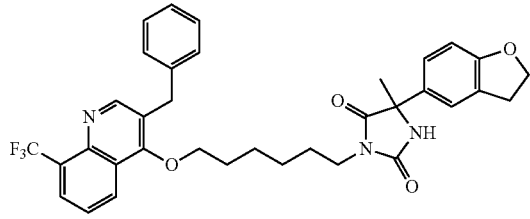

5-(2,3-dihydrobenzofuran-5-yl)-5-methylimidazolidine-2,4-dione was used in place of 5-(benzo[d][1,3]dioxol-5-yl)-5-methylimidazolidine-2,4-dione of Example 1f) for a similar reaction and treatment, and the title compound was obtained as a colorless oil.

¹H-NMR (CDCl₃) δ: 1.32-1.42 (2H, m), 1.47-1.70 (4H, m), 1.79 (3H, s), 1.85 (2H, quintet, J=7.3 Hz), 3.19 (2H, t, J=8.6 Hz), 3.52 (2H, t, J=7.3 Hz), 3.95 (2H, t, J=6.6 Hz), 4.18 (2H, s), 4.56 (2H, t, J=8.6 Hz), 5.70 (1H, s), 6.75 (1H, d, J=8.2 Hz), 7.17-7.30 (7H, m), 7.58 (1H, dd, J=6.6, 7.6 Hz), 8.02 (1H, d, J=6.6 Hz), 8.26 (1H, d, J=7.6 Hz), 8.85 (1H, s).

Example 6

Preparation of 3-{6-[3-benzyl-8-(trifluoromethyl)quinolin-4-yloxy]hexyl}-5-methyl-5-(quinoxalin-6-yl)imidazolidine-2,4-dione

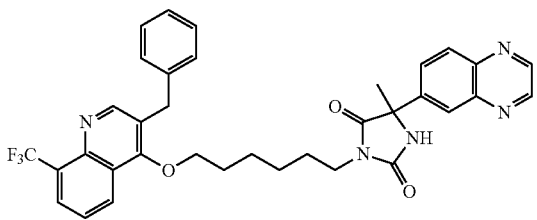

5-methyl-5-(quinoxalin-6-yl)imidazolidine-2,4-dione was used in place of 5-(benzo[d][1,3]dioxol-5-yl)-5-methylimidazolidine-2,4-dione of Example 1f) for a similar reaction and treatment, and the title compound was obtained as a colorless oil.

¹H-NMR (CDCl₃) δ: 1.31-1.43 (2H, m), 1.48-1.74 (4H, m), 1.79-1.87 (2H, m), 1.97 (3H, s), 3.56 (2H, t, J=7.3 Hz), 3.93 (2H, t, J=6.6 Hz), 4.17 (2H, s), 6.08 (1H, s), 7.19-7.31 (5H, m), 7.57 (1H, dd, J=7.3, 8.6 Hz), 7.97 (1H, dd, J=2.3, 8.9 Hz), 8.02 (1H, d, J=7.3 Hz), 8.15 (1H, d, J=8.6 Hz), 8.22-8.27 (2H, m), 8.84-8.86 (3H, m).

Example 7

Preparation of 3-{6-[3-benzyl-8-(trifluoromethyl)quinolin-4-yloxy]hexyl}-5-(4-isopropoxyphenyl)-5-methylimidazolidine-2,4-dione

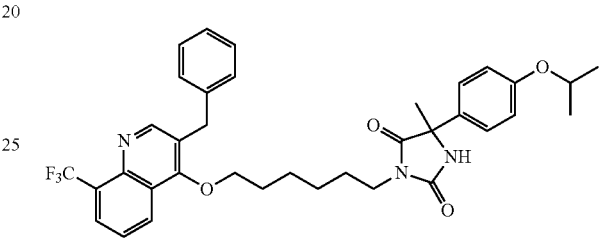

5-(4-isopropoxyphenyl)-5-methylimidazolidine-2,4-dione was used in place of 5-(benzo[d][1,3]dioxol-5-yl)-5-methylimidazolidine-2,4-dione of Example 1f) for a similar reaction and treatment, and the title compound was obtained as a colorless oil.

¹H-NMR (CDCl₃) δ: 1.31 (6H, d, J=6.3 Hz), 1.35 (2H, tt, J=5.9, 7.3 Hz), 1.53 (2H, tt, J=7.3, 7.6 Hz), 1.58-1.71 (2H, m), 1.80 (3H, s), 1.85 (2H, tt, J=6.6, 7.6 Hz), 3.52 (2H, t, J=7.3 Hz), 3.95 (2H, t, J=6.6 Hz), 4.19 (2H, s), 4.52 (1H, q, J=6.3 Hz), 5.91 (1H, s), 6.86 (2H, d, J=8.9 Hz), 7.16-7.32 (5H, m), 7.36 (2H, d, J=8.9 Hz), 7.58 (1H, dd, J=7.3, 7.9 Hz), 8.03 (1H, d, J=7.3 Hz), 8.26 (1H, d, J=7.9 Hz), 8.85 (1H, s).

Example 8

Preparation of 3-{6-[3-benzyl-8-(trifluoromethyl)quinolin-4-yloxy]hexyl}-5-(3-fluoro-4-isopropoxyphenyl)-5-methylimidazolidine-2,4-dione

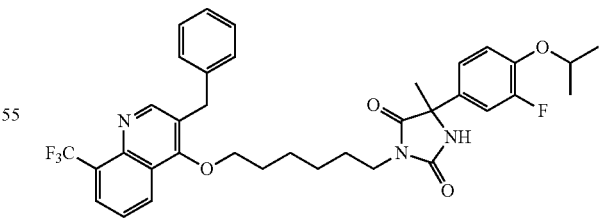

5-(3-fluoro-4-isopropoxyphenyl)-5-methylimidazolidine-2,4-dione was used in place of 5-(benzo[d][1,3]dioxol-5-yl)-5-methylimidazolidine-2,4-dione of Example 1f) for a similar reaction and treatment, and the title compound was obtained as a colorless oil.

¹H-NMR (CDCl₃) δ: 1.34 (6H, d, J=5.9 Hz), 1.36-1.44 (2H, m), 1.47-1.72 (4H, m), 1.79 (3H, s), 1.85 (2H, quintet, J=6.9 Hz), 3.52 (2H, t, J=7.3 Hz), 3.95 (2H, t, J=6.9 Hz), 4.19 (2H, s), 4.52 (1H, septet, J=5.9 Hz), 5.89 (1H, s), 6.95 (1H, t, J=8.6 Hz), 7.12-7.32 (7H, m), 7.58 (1H, dd, J=6.6, 7.6 Hz), 8.03 (1H, d, J=6.6 Hz), 8.26 (1H, d, J=7.6 Hz), 8.86 (1H, s).

Example 9

Preparation of 3-{6-[3-benzyl-8-(trifluoromethyl) quinolin-4-yloxy]hexyl}-5-(3-fluoro-4-isopropoxyphenyl)-5-ethylimidazolidine-2,4-dione

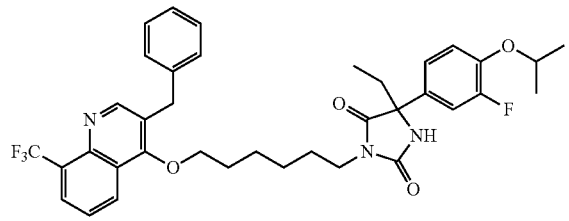

5-(3-fluoro-4-isopropoxyphenyl)-5-ethylimidazolidine-2,4-dione was used in place of 5-(benzo[d][1,3]dioxol-5-yl)-5-methylimidazolidine-2,4-dione of Example 1f) for a similar reaction and treatment, and the title compound was obtained as a colorless oil.

$^1$H-NMR (CDCl$_3$) δ: 0.90 (3H, t, J=7.6 Hz), 1.34 (6H, d, J=6.3 Hz), 1.45-1.68 (6H, m), 1.79-1.90 (2H, m), 2.05 (1H, qd, J=7.6, 14.5 Hz), 2.20 (1H, qd, J=7.6, 14.5 Hz), 3.51 (2H, t, J=6.9 Hz), 3.95 (2H, t, J=6.3 Hz), 4.19 (2H, s), 4.52 (1H, septet, J=6.3 Hz), 5.94 (1H, s), 6.94 (1H, t, J=8.2 Hz), 7.15-7.29 (7H, m), 7.58 (1H, dd, J=7.3, 8.2 Hz), 8.03 (1H, d, J=7.3 Hz), 8.26 (1H, d, J=8.2 Hz), 8.86 (1H, s).

Example 10

Preparation of 3-{6-[3-benzyl-8-(trifluoromethyl) quinolin-4-yloxy]hexyl}-5-(6-ethoxypyridin-3-yl)-5-methylimidazolidine-2,4-dione

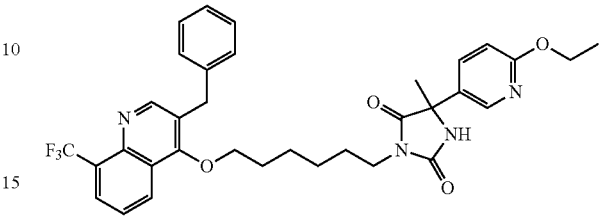

5-(6-ethoxypyridin-3-yl)-5-methylimidazolidine-2,4-dione was used in place of 5-(benzo[d][1,3]dioxol-5-yl)-5-methylimidazolidine-2,4-dione of Example 1f) for a similar reaction and treatment, and the title compound was obtained as a colorless oil.

$^1$H-NMR (CDCl$_3$) δ: 1.34-1.69 (9H, m), 1.80-1.87 (5H, m), 3.55 (2H, t, J=7.3 Hz), 3.95 (2H, t, J=6.9 Hz), 4.18 (2H, s), 4.32 (2H, q, J=7.3 Hz), 6.72 (1H, d, J=8.6 Hz), 7.16-7.30 (6H, m), 7.39 (1H, dd, J=2.6, 8.9 Hz), 7.57 (1H, dd, J=6.9, 7.9 Hz), 8.02 (1H, d, J=6.9 Hz), 8.08 (1H, d, J=2.6 Hz), 8.24 (1H, dd, J=4.0, 7.9 Hz), 8.85 (1H, s).

Example 11

Preparation of 3-{6-[3-benzyl-8-(trifluoromethyl) quinolin-4-yloxy]hexyl}-5-methyl-5-(6-propoxypyridin-3-yl)imidazolidine-2,4-dione

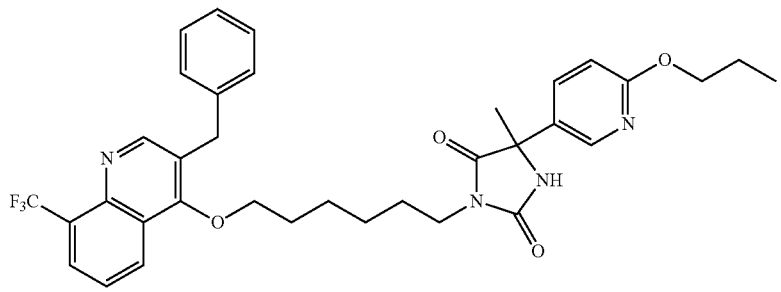

5-methyl-5-(6-propoxypyridin-3-yl)imidazolidine-2,4-dione was used in place of 5-(benzo[d][1,3]dioxol-5-yl)-5-methylimidazolidine-2,4-dione of Example 1f) for a similar reaction and treatment, and the title compound was obtained as a colorless oil.

¹H-NMR (CDCl₃) δ: 1.31-1.58 (9H, m), 1.62-1.91 (7H, m), 3.55 (2H, t, J=7.3 Hz), 3.95 (2H, t, J=6.9 Hz), 4.17-4.25 (4H, m), 6.73 (1H, d, J=8.6 Hz), 7.16-7.31 (6H, m), 7.39 (1H, dd, J=2.6, 8.9 Hz), 7.57 (1H, dd, J=6.9, 7.9 Hz), 8.02 (1H, d, J=6.9 Hz), 8.08 (1H, d, J=2.6 Hz), 8.25 (1H, dd, J=4.0, 7.9 Hz), 8.84 (1H, s).

Example 12

Preparation of 3-{6-[3-benzyl-8-(trifluoromethyl)quinolin-4-yloxy]hexyl}-5-(6-isopropoxypyridin-3-yl)-5-methylimidazolidine-2,4-dione

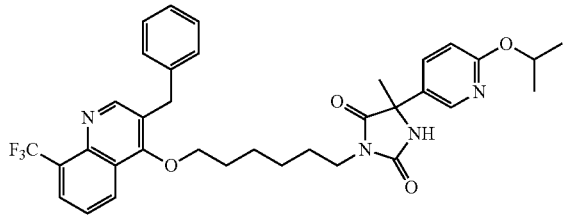

5-(6-isopropoxypyridin-3-yl)-5-methylimidazolidine-2,4-dione was used in place of 5-(benzo[d][1,3]dioxol-5-yl)-5-methylimidazolidine-2,4-dione of Example 1f) for a similar reaction and treatment, and the title compound was obtained as a colorless oil.

¹H-NMR (CDCl₃) δ: 1.30-1.43 (8H, m), 1.47-1.72 (4H, m), 1.80 (3H, s), 1.88 (2H, quintet, J=6.6 Hz), 3.52 (2H, t, J=7.3 Hz), 3.95 (2H, t, J=6.6 Hz), 4.18 (2H, s), 5.26 (1H, septet, J=5.9 Hz), 6.18 (1H, s), 6.68 (1H, d, J=8.2 Hz), 7.19-7.32 (5H, m), 7.58 (1H, dd, J=6.9, 7.3 Hz), 7.66 (1H, dd, J=2.6, 8.6 Hz), 8.02 (1H, d, J=7.3 Hz), 8.23-8.28 (2H, m), 8.85 (1H, s).

Example 13

Preparation of 5-(benzo[d][1,3]dioxol-5-yl)-3-{4-[3-benzyl-8-(trifluoromethyl)quinolin-4-yloxy]butyl}-5-methylimidazolidine-2,4-dione

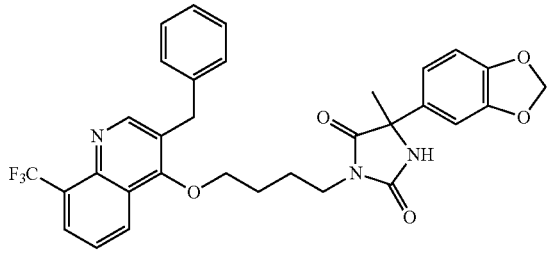

1,4-dibromobutane was used in place of 1,6-dibromohexane for a reaction and treatment in Example 1e) and then for a similar reaction and treatment as Example 1f), and the title compound was obtained as a colorless oil.

¹H-NMR (CDCl₃) δ: 1.80 (3H, s), 1.82-1.94 (4H, m), 3.62 (2H, t, J=6.9 Hz), 3.95 (2H, t, J=5.9 Hz), 4.16 (2H, s), 5.80 (1H, s), 5.94 (2H, s), 6.77 (1H, d, J=8.2 Hz), 6.93 (1H, dd, J=2.0, 8.2 Hz), 6.97 (1H, d, J=2.0 Hz), 7.16-7.31 (5H, m), 7.58 (1H, dd, J=6.6, 8.2 Hz), 8.02 (1H, d, J=6.6 Hz), 8.23 (1H, d, J=8.2 Hz), 8.85 (1H, s).

Example 14

Preparation of 5-(benzo[d][1,3]dioxol-5-yl)-3-{4-[3-benzyl-8-(trifluoromethyl)quinolin-4-yloxy]butyl}-5-ethylimidazolidine-2,4-dione

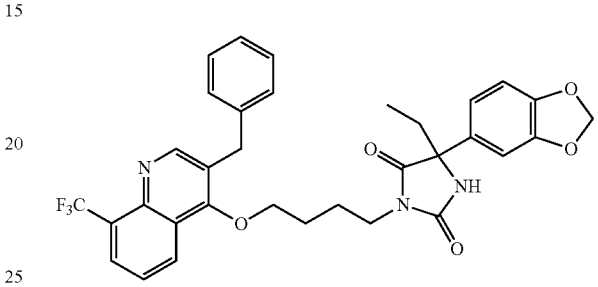

5-(benzo[d][1,3]dioxol-5-yl)-5-ethylimidazolidine-2,4-dione was used in place of 5-(benzo[d][1,3]dioxol-5-yl)-5-methylimidazolidine-2,4-dione in Example 13 for a similar reaction and treatment, and the title compound was obtained as a colorless oil.

¹H-NMR (CDCl₃) δ: 0.90 (3H, t, J=7.3 Hz), 1.81-1.91 (4H, m), 2.06 (1H, qd, J=7.3, 14.2 Hz), 2.20 (1H, qd, J=7.3, 14.2 Hz), 3.60 (2H, t, J=6.3 Hz), 3.95 (2H, t, J=5.3 Hz), 4.16 (2H, s), 5.91 (1H, s), 5.94 (1H, d, J=1.3 Hz), 5.95 (1H, d, J=1.3 Hz), 6.77 (1H, d, J=8.2 Hz), 6.94 (1H, dd, J=2.0, 8.2 Hz), 7.03 (1H, d, J=2.0 Hz), 7.16-7.31 (5H, m), 7.58 (1H, t, J=7.3 Hz), 8.02 (1H, d, J=7.3 Hz), 8.23 (1H, d, J=7.3 Hz), 8.85 (1H, s).

Example 15

Preparation of 3-{4-[3-benzyl-8-(trifluoromethyl)quinolin-4-yloxy]butyl}-5-(2,3-dihydrobenzo[b][1,4]dioxin-6-yl)-5-ethylimidazolidine-2,4-dione

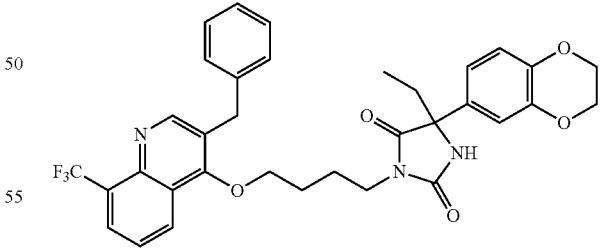

5-(2,3-dihydrobenzo[b][1,4]dioxin-6-yl)-5-ethylimidazolidine-2,4-dione was used in place of 5-(benzo[d][1,3]dioxol-5-yl)-5-methylimidazolidine-2,4-dione in Example 13 for a similar reaction and treatment, and the title compound was obtained as a colorless oil.

¹H-NMR (CDCl₃) δ: 0.89 (3H, t, J=7.3 Hz), 1.83-1.91 (4H, m), 2.06 (1H, qd, J=7.3, 14.2 Hz), 2.21 (1H, qd, J=7.3, 14.2 Hz), 3.60 (2H, t, J=6.3 Hz), 3.95 (2H, t, J=5.3 Hz), 4.16 (2H, s), 4.22 (4H, s), 5.88 (1H, s), 6.85 (1H, d, J=8.6 Hz), 6.96 (1H, dd, J=2.3, 8.6 Hz), 7.02 (1H, d, J=2.3 Hz), 7.15-7.30 (5H, m), 7.58 (1H, dd, J=6.6, 7.3 Hz), 8.02 (1H, d, J=6.6 Hz), 8.23 (1H, d, J=7.3 Hz), 8.85 (1H, s).

Example 16

Preparation of 3-{4-[3-benzyl-8-(trifluoromethyl)quinolin-4-yloxy]butyl}-5-(4-isopropoxyphenyl)-5-methylimidazolidine-2,4-dione

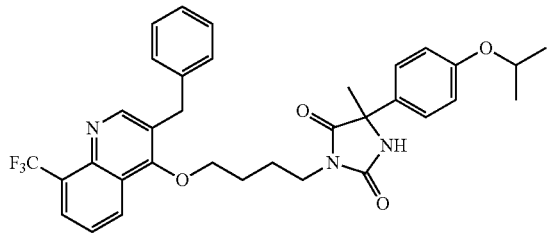

5-(4-isopropoxyphenyl)-5-methylimidazolidine-2,4-dione was used in place of 5-(benzo[d][1,3]dioxol-5-yl)-5-methylimidazolidine-2,4-dione in Example 13 for a similar reaction and treatment, and the title compound was obtained as a colorless oil.

$^1$H-NMR (CDCl$_3$) δ: 1.30 (6H, d, J=5.9 Hz), 1.81 (3H, s), 1.83-1.92 (4H, m), 3.61 (2H, t, J=6.3 Hz), 3.96 (2H, t, J=5.3 Hz), 4.16 (2H, s), 4.49 (1H, q, J=5.9 Hz), 6.03 (1H, s), 6.85 (2H, d, J=8.9 Hz), 7.15-7.31 (5H, m), 7.36 (2H, d, J=8.9 Hz), 7.57 (1H, dd, J=7.8, 8.2 Hz), 8.02 (1H, d, J=8.2 Hz), 8.23 (1H, d, J=7.3 Hz), 8.85 (1H, s).

Example 17

Preparation of 5-(benzo[d][1,3]dioxol-5-yl)-3-{5-[3-benzyl-8-(trifluoromethyl)quinolin-4-yloxy]pentyl}-5-methylimidazolidine-2,4-dione

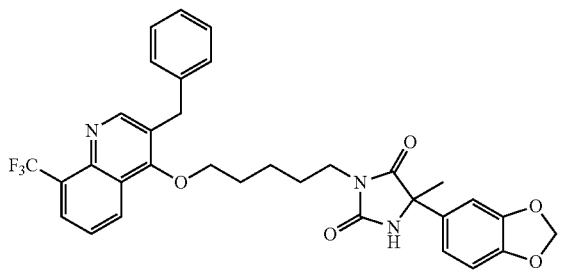

1,5-dibromopentane was used in place of 1,6-dibromohexane for a reaction and treatment in Example 1e) and then for a similar reaction and treatment as Example 1f), and the title compound was obtained as a colorless oil.

$^1$H-NMR (CDCl$_3$) δ: 1.56 (2H, tt, J=7.3, 7.6 Hz), 1.69 (2H, tt, J=6.9, 7.6 Hz), 1.78 (3H, s), 1.89 (2H, tt, J=6.3, 7.3 Hz), 3.58 (2H, t, J=6.9 Hz), 3.92 (2H, t, J=6.3 Hz), 4.17 (2H, s), 5.84 (1H, s), 5.86 (1H, d, J=1.0 Hz), 5.87 (1H, d, J=1.0 Hz), 6.73 (1H, d, J=7.9 Hz), 6.91 (1H, dd, J=2.0, 7.9 Hz), 6.95 (1H, d, J=2.0 Hz), 7.16-7.29 (5H, m), 7.57 (1H, dd, J=7.3, 7.9 Hz), 8.02 (1H, d, J=7.3 Hz), 8.20 (1H, J=7.9 Hz), 8.86 (1H, s).

Example 18

Preparation of 5-(benzo[d][1,3]dioxol-5-yl)-3-{5-[3-benzyl-8-(trifluoromet hyl)quinolin-4-yloxy]pentyl}-5-ethylimidazolidine-2,4-dione

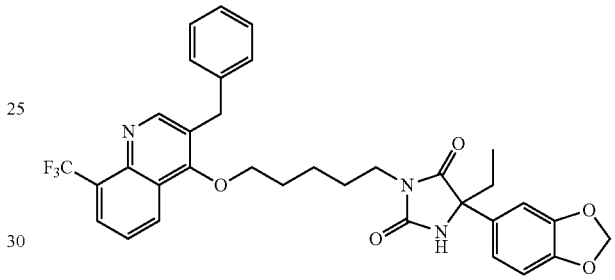

5-(benzo[d][1,3]dioxol-5-yl)-5-ethylimidazolidine-2,4-dione was used in place of 5-(benzo[d][1,3]dioxol-5-yl)-5-methylimidazolidine-2,4-dione in Example 17 for a similar reaction and treatment, and the title compound was obtained as a colorless oil.

$^1$H-NMR (CDCl$_3$) δ: 0.89 (3H, t, J=7.3 Hz), 1.55 (2H, tt, J=7.3, 7.6 Hz), 1.69 (2H, tt, J=6.9, 7.6 Hz), 1.88 (2H, tt, J=6.3, 7.3 Hz), 2.05 (1H, qd, J=7.3, 14.2 Hz), 2.19 (1H, qd, J=7.3, 14.2 Hz), 3.54 (2H, t, J=6.9 Hz), 3.91 (2H, t, J=6.3 Hz), 4.17 (2H, s), 5.88 (1H, d, J=1.3 Hz), 5.89 (1H, d, J=1.3 Hz), 5.97 (1H, s), 6.74 (1H, d, J=8.2 Hz), 6.92 (1H, dd, J=2.0, 8.2 Hz), 7.01 (1H, d, J=2.0 Hz), 7.16-7.31 (5H, m), 7.58 (1H, t, J=7.3 Hz), 8.03 (1H, d, J=7.3 Hz), 8.21 (1H, J=7.3 Hz), 8.85 (1H, s).

Example 19

Preparation of 3-{5-[3-benzyl-8-(trifluoromethyl)quinolin-4-yloxy]pentyl}-5-(2,3-dihydrobenzo[b][1,4]dioxin-6-yl)-5-methylimidazolidine-2,4-dione

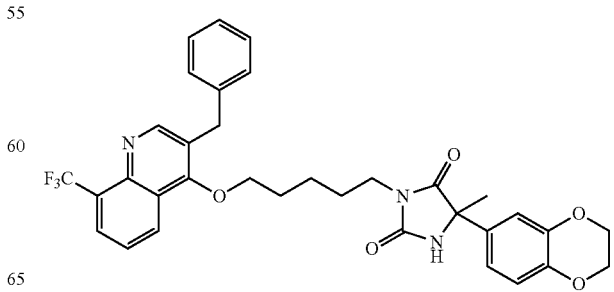

5-(2,3-dihydrobenzo[b][1,4]dioxin-6-yl)-5-methylimidazolidine-2,4-dione was used in place of 5-(benzo[d][1,3]dioxol-5-yl)-5-methylimidazolidine-2,4-dione in Example 17 for a similar reaction and treatment, and the title compound was obtained as a colorless oil.

$^1$H-NMR (CDCl$_3$) δ: 1.48-1.60 (2H, m), 1.65-1.77 (5H, m), 1.88 (2H, quintet, J=7.3 Hz), 3.55 (2H, t, J=6.9 Hz), 3.92 (2H, t, J=6.6 Hz), 4.15 (4H, s), 4.17 (4H, s), 5.72 (1H, s), 6.81 (1H, d, J=8.2 Hz), 6.91 (1H, dd, J=2.3, 8.2 Hz), 6.96 (1H, dd, 2.3 Hz), 7.18-7.28 (5H, m), 7.57 (1H, dd, J=7.6, 8.2 Hz), 8.02 (1H, d, J=7.6 Hz), 8.21 (1H, d, J=8.2 Hz), 8.85 (1H, s).

Example 20

Preparation of 3-{5-[3-benzyl-8-(trifluoromethyl)quinolin-4-yloxy]pentyl}-5-(2,3-dihydrobenzo[b][1,4]dioxin-6-yl)-5-ethylimidazolidine-2,4-dione

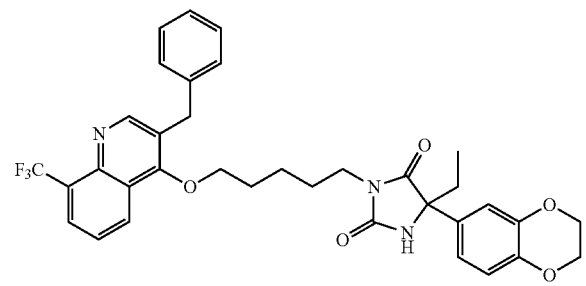

5-(2,3-dihydrobenzo[b][1,4]dioxin-6-yl)-5-ethylimidazolidine-2,4-dione was used in place of 5-(benzo[d][1,3]dioxol-5-yl)-5-methylimidazolidine-2,4-dione in Example 17 for a similar reaction and treatment, and the title compound was obtained as a colorless oil.

$^1$H-NMR (CDCl$_3$) δ: 0.88 (3H, t, J=7.3 Hz), 1.52 (2H, tt, J=7.3, 7.6 Hz), 1.66 (2H, tt, J=6.9, 7.6 Hz), 1.88 (2H, tt, J=6.3, 7.3 Hz), 2.04 (1H, qd, J=7.3, 14.2 Hz), 2.19 (1H, qd, J=7.3, 14.2 Hz), 3.54 (2H, t, J=6.9 Hz), 3.91 (2H, t, J=6.3 Hz), 4.16 (6H, s), 5.96 (1H, s), 6.82 (1H, d, J=8.6 Hz), 6.93 (1H, dd, J=2.3, 8.6 Hz), 7.01 (1H, d, J=2.3 Hz), 7.17-7.31 (5H, m), 7.58 (1H, dd, J=7.3, 7.6 Hz), 8.03 (1H, d, J=7.3 Hz), 8.22 (1H, J=7.6 Hz), 8.85 (1H, s).

Example 21

Preparation of 3-{5-[3-benzyl-8-(trifluoromethyl)quinolin-4-yloxy]pentyl}-5-(2,3-dihydrobenzofuran-5-yl)-5-methylimidazolidine-2,4-dione

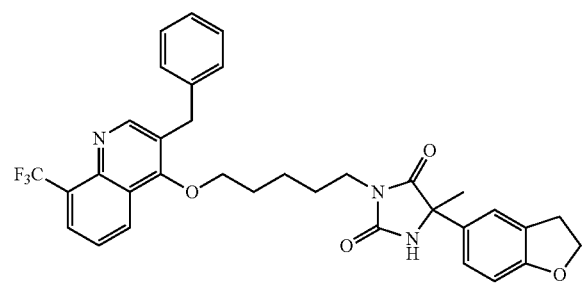

5-(2,3-dihydrobenzofuran-5-yl)-5-methylimidazolidine-2,4-dione was used in place of 5-(benzo[d][1,3]dioxol-5-yl)-5-methylimidazolidine-2,4-dione in Example 17 for a similar reaction and treatment, and the title compound was obtained as a colorless oil.

$^1$H-NMR (CDCl$_3$) δ: 1.50-1.60 (2H, m), 1.66-1.79 (5H, m), 1.89 (2H, quintet, J=7.3 Hz), 3.13 (2H, t, J=8.6 Hz), 3.56 (2H, t, J=6.9 Hz), 3.92 (2H, t, J=6.3 Hz), 4.17 (2H, s), 4.51 (2H, t, J=8.9 Hz), 5.67 (1H, s), 6.72 (1H, d, J=8.6 Hz), 7.16-7.31 (7H, m), 7.57 (1H, dd, J=7.3, 8.9 Hz), 8.02 (1H, d, J=7.3 Hz), 8.21 (1H, d, J=8.9 Hz), 8.85 (1H, s).

Example 22

Preparation of 3-{5-[3-benzyl-8-(trifluoromethyl)quinolin-4-yloxy]pentyl}-5-(4-isopropoxyphenyl)-5-methylimidazolidine-2,4-dione

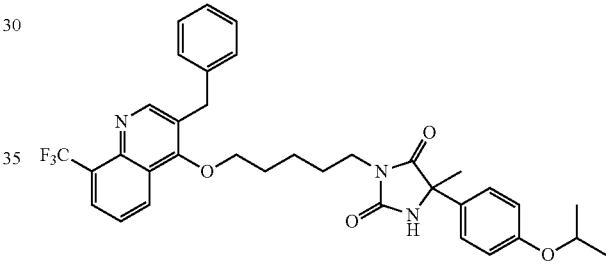

5-(4-isopropoxyphenyl)-5-methylimidazolidine-2,4-dione was used in place of 5-(benzo[d][1,3]dioxol-5-yl)-5-methylimidazolidine-2,4-dione in Example 17 for a similar reaction and treatment, and the title compound was obtained as a colorless oil.

$^1$H-NMR (CDCl$_3$) δ: 1.27 (6H, t, J=6.3 Hz), 1.56 (2H, tt, J=7.3, 7.6 Hz), 1.68 (2H, tt, J=6.9, 7.6 Hz), 1.79 (3H, s), 1.89 (2H, tt, J=6.3, 7.3 Hz), 3.56 (2H, t, J=6.9 Hz), 3.92 (2H, t, J=6.3 Hz), 4.17 (2H, s), 4.43 (1H, q, J=6.3 Hz), 5.91 (1H, s), 6.82 (2H, d, J=8.9 Hz), 7.18-7.28 (5H, m), 7.35 (2H, d, J=8.9 Hz), 7.57 (1H, dd, J=6.9, 7.3 Hz), 8.02 (1H, d, J=6.9 Hz), 8.22 (1H, d, J=7.3 Hz), 8.85 (1H, s).

Example 23

Preparation of 3-{7-[3-benzyl-8-(trifluoromethyl)quinolin-4-yloxy]heptyl}-5-(2,3-dihydrobenzo[b][1,4]dioxin-6-yl)-5-methylimidazolidine-2,4-dione

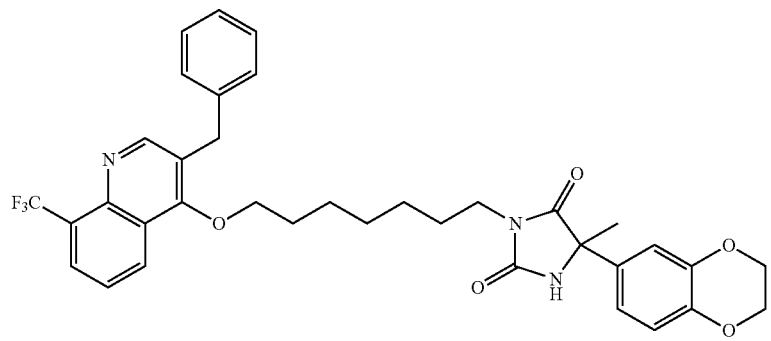

After 1,7-dibromoheptane was used in place of 1,6-dibromohexane for a reaction and treatment in Example 1e), 5-(2,3-dihydrobenzo[b][1,4]dioxin-6-yl)-5-methylimidazolidine-2,4-dione was used in place of 5-(benzo[d][1,3]dioxol-5-yl)-5-methylimidazolidine-2,4-dione in Example 1f) for a similar reaction and treatment, and the title compound was obtained as a colorless oil.

$^1$H-NMR (CDCl$_3$) δ: 1.25-1.37 (4H, m), 1.42-1.52 (2H, m), 1.59-1.66 (2H, m), 1.77 (3H, s), 1.84 (2H, quintet, J=6.9 Hz), 3.50 (2H, t, J=7.3 Hz), 3.96 (2H, t, J=6.6 Hz), 4.19 (2H, s), 4.21 (4H, s), 5.68 (1H, s), 6.85 (1H, d, J=8.2 Hz), 6.90 (1H, dd, J=2.3, 8.2 Hz), 6.98 (1H, d, J=2.3 Hz), 7.17-7.31 (5H, m), 7.58 (1H, dd, J=7.3, 8.2 Hz), 8.02 (1H, d, J=7.3 Hz), 8.27 (1H, d, J=8.2 Hz), 8.85 (1H, s).

Example 24

Preparation of 3-{7-[3-benzyl-8-(trifluoromethyl)quinolin-4-yloxy]heptyl}-5-(2,3-dihydrobenzofuran-5-yl)-5-methylimidazolidine-2,4-dione

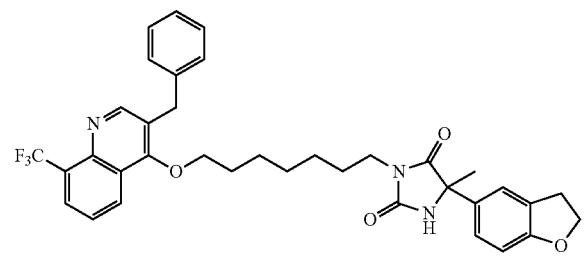

5-(2,3-dihydrobenzofuran-5-yl)-5-methylimidazolidine-2,4-dione was used in place of 5-(2,3-dihydrobenzo[b][1,4]dioxin-6-yl)-5-methylimidazolidine-2,4-dione in Example 23 for a similar reaction and treatment, and the title compound was obtained as a colorless oil.

$^1$H-NMR (CDCl$_3$) δ: 1.28-1.38 (4H, m), 1.42-1.52 (2H, m), 1.56-1.67 (2H, m), 1.79 (3H, s), 1.85 (2H, quintet, J=6.9 Hz), 3.19 (2H, t, J=8.6 Hz), 3.51 (2H, t, J=6.9 Hz), 3.96 (2H, t, J=6.5 Hz), 4.19 (2H, s), 4.55 (2H, t, J=8.6 Hz), 5.66 (1H, s), 6.76 (1H, d, J=8.3 Hz), 7.17-7.30 (7H, m), 7.58 (1H, dd, J=7.3, 8.6 Hz), 8.03 (1H, d, J=7.3 Hz), 8.27 (1H, d, J=8.6 Hz), 8.85 (1H, s).

Example 25

Preparation of 5-(benzo[d][1,3]dioxol-5-yl)-3-(3-(3-[3-benzyl-8-(trifluoromethyl)quinolin-4-yl]phenoxy)propyl)-5-methylimidazolidine-2,4-dione

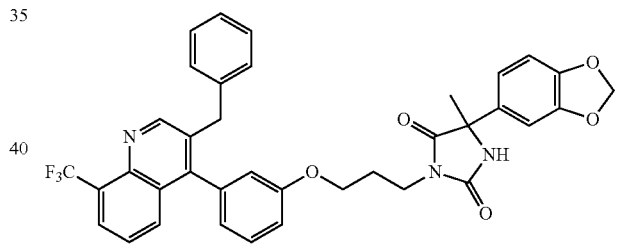

a) Preparation of 3-(3-benzyl-8-(trifluoromethyl)quinolin-4-yl)phenol

To a solution of 3-benzyl-8-(trifluoromethyl)quinolin-4-ol (8.0 g, 26.4 mmol) in N,N-dimethylformamide (132 mL), potassium carbonate (13.1 g, 95.0 mmol) and N-phenylbis(trifluoromethanesulfonimide (11.3 g, 31.7 mmol) were added. The resultant mixture was heated to 50° C. and stirred for 1 hour. The reaction solution was added with water at room temperature, extracted with diethylether. Subsequently, the organic layer was washed with brine, dried using anhydrous sodium sulfate, and concentrated in vacuo. 11.0 g of triflate crude product was obtained as a pale yellow crystal. To a solution of the obtained crude product in 1,4-dioxane (126 mL), tripotassium phosphate (20.3 g, 95.8 mmol), 3-hydroxyphenylboronic acid (4.17 g, 30.2 mmol), and tetrakis triphenylphosphine palladium (2.91 g, 2.52 mmol) were added, and the resultant mixture was stirred at 100° C. overnight. The reaction solution was added with water at room temperature and extracted with ethyl acetate. Subsequently, the organic layer was washed with brine, dried using anhydrous sodium sulfate, and concentrated in vacuo. The obtained residue was purified using silica-gel column chromatography (hexane/ethyl acetate), and the title compound (8.42 g, yield 84%) was obtained as an yellow amorphous.

¹H-NMR (CDCl₃) δ: 3.94-4.02 (2H, m), 5.54 (1H, s), 6.64-6.65 (1H, m), 6.76 (1H, d, J=7.6 Hz), 6.97-6.99 (3H, m), 7.12-7.21 (3H, m), 7.37 (1H, dd, J=7.8, 8.1 Hz), 7.45 (1H, dd, J=7.8, 8.1 Hz), 7.70 (1H, d, J=8.3 Hz), 8.02 (1H, d, J=7.1 Hz), 8.99 (1H, s).

b) Preparation of 3-benzyl-4-[3-(3-bromopropyloxyphenyl)]-8-(trifluoromethyl) quinoline 1,3-dibromopropane was used in place of 1,6-dibromohexane of Example 1e) for a similar reaction and treatment of 3-[3-benzyl-8-(trifluoromethyl)quinolin-4-yl]phenol, and the title compound was obtained as a colorless oil.

¹H-NMR (CDCl₃) δ: 2.29 (2H, quintet, J=6.3 Hz), 3.59 (2H, t, J=6.3 Hz), 3.91-4.08 (4H, m), 6.65 (1H, dd, J=1.3, 2.3 Hz), 6.81 (1H, td, J=1.3, 7.6 Hz), 6.96-7.05 (3H, m), 7.12-7.25 (3H, m), 7.41 (1H, dd, J=6.6, 8.6 Hz), 7.47 (1H, d, J=7.6 Hz), 7.69 (1H, d, J=8.6 Hz), 8.02 (1H, d, J=6.6 Hz), 9.02 (1H, s).

c) Preparation of 5-(benzo[d][1,3]dioxol-5-yl)-3-(3-{3-[3-benzyl-8-(trifluoromethyl)quinolin-4-yl]phenoxy}propyl)-5-methylimidazolidine-2,4-dione 3-benzyl-4-[3-(3-bromopropyloxyphenyl)]-8-(trifluoromethyl) quinoline was used for a similar reaction and treatment as Example 1f), and the title compound was obtained as a colorless oil.

¹H-NMR (CDCl₃) δ: 1.75 (3H, s), 2.09 (2H, t, J=6.6 Hz), 3.71 (2H, t, J=6.9 Hz), 3.83-3.92 (2H, m), 3.97 (2H, d, J=2.3 Hz), 5.67 (1H, s), 5.91 (2H, d, J=1.6 Hz), 6.61 (1H, s), 6.73 (1H, d, J=7.9 Hz), 6.77 (1H, d, J=7.6 Hz), 6.89 (1H, dd, J=2.0, 7.6 Hz), 6.94 (1H, d, J=2.0 Hz), 6.95-7.00 (3H, m), 7.13-7.23 (3H, m), 7.37 (1H, dd, J=7.6, 8.9 Hz), 7.43 (1H, dt, J=3.3, 8.2 Hz), 7.67 (1H, d, J=8.9 Hz), 8.01 (1H, d, J=7.6 Hz), 9.00 (1H, s).

Example 26

Preparation of 5-(benzo[d][1,3]dioxol-5-yl)-3-(3-{3-[3-benzyl-8-(trifluoromethyl) quinolin-4-yl]phenoxy}propyl)-5-ethylimidazolidine-2,4-dione

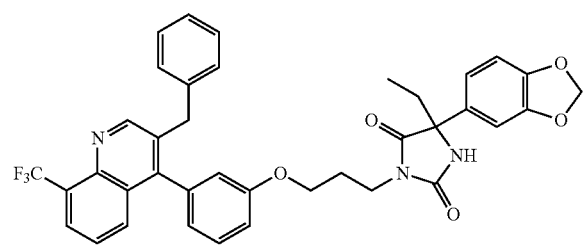

5-(benzo[d][1,3]dioxol-5-yl)-5-ethylimidazolidine-2,4-dione was used in place of 5-(benzo[d][1,3]dioxol-5-yl)-5-methylimidazolidine-2,4-dione of Example 25c) for a similar reaction and treatment, and the title compound was obtained as a colorless oil.

¹H-NMR (CDCl₃) δ: 0.87 (3H, t, J=7.6 Hz), 2.03 (1H, qt, J=7.6, 14.2 Hz), 2.05-2.11 (2H, m), 2.16 (1H, qd, J=7.6, 14.2 Hz), 3.69 (2H, t, J=6.9 Hz), 3.80-3.92 (2H, m), 3.97 (2H, d, J=2.3 Hz), 5.83 (1H, s), 5.91 (1H, d, J=1.3 Hz), 5.92 (1H, d, J=1.3 Hz), 6.61 (1H, s), 6.73 (1H, d, J=8.2 Hz), 6.77 (1H, d, J=7.3 Hz), 6.91 (1H, dd, J=2.0, 8.2 Hz), 6.95-7.01 (4H, m), 7.13-7.23 (3H, m), 7.37 (1H, dd, J=7.3, 8.6 Hz), 7.45 (1H, dt, J=2.0, 6.9 Hz), 7.67 (1H, d, J=8.6 Hz), 8.01 (1H, d, J=7.3 Hz), 9.00 (1H, s).

Example 27

Preparation of 3-(3-{3-[3-benzyl-8-(trifluoromethyl)quinolin-4-yl]phenoxy}propyl)-5-(2,3-dihydrobenzo[b][1,4]dioxin-6-yl)-5-methylimidazolidine-2,4-dione

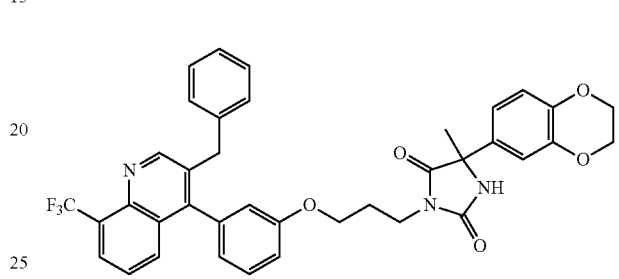

5-(2,3-dihydrobenzo[b][1,4]dioxin-6-yl)-5-methylimidazolidine-2,4-dione was used in place of 5-(benzo[d][1,3]dioxol-5-yl)-5-methylimidazolidine-2,4-dione of Example 25c) for a similar reaction and treatment, and the title compound was obtained as a colorless oil.

¹H-NMR (CDCl₃) δ: 1.74 (3H, s), 2.08 (2H, t, J=6.3 Hz), 3.70 (2H, t, J=7.3 Hz), 3.82-3.95 (2H, m), 3.97 (2H, d, J=2.0 Hz), 4.18 (4H, s), 5.76 (1H, s), 6.62 (1H, s), 6.77 (1H, d, J=8.2 Hz), 6.80 (1H, d, J=7.6 Hz), 6.90 (1H, dd, J=2.3, 8.6 Hz), 6.93 (4H, m), 7.15-7.23 (3H, m), 7.37 (1H, dd, J=6.9, 8.6 Hz), 7.45 (1H, dt, J=2.0, 7.5 Hz), 7.68 (1H, d, J=8.6 Hz), 8.01 (1H, d, J=6.9 Hz), 9.00 (1H, s).

Example 28

Preparation of 3-(3-{3-[3-benzyl-8-(trifluoromethyl)quinolin-4-yl]phenoxy}propyl)-5-(2,3-dihydrobenzo[b][1,4]dioxin-6-yl)-5-ethylimidazolidine-2,4-dione

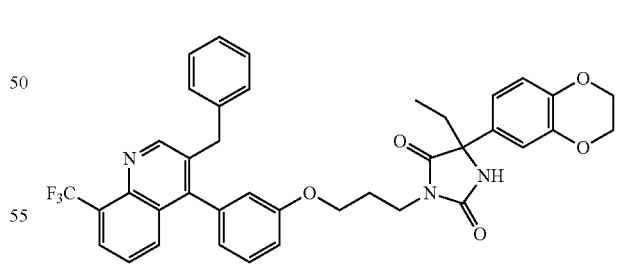

5-(2,3-dihydrobenzo[b][1,4] dioxin-6-yl)-5-ethylimidazolidine-2,4-dione was used in place of 5-(benzo[d][1,3]dioxol-5-yl)-5-methylimidazolidine-2,4-dione of Example 25c) for a similar reaction and treatment, and the title compound was obtained as a colorless oil.

¹H-NMR (CDCl₃) δ: 0.87 (3H, t, J=7.3 Hz), 1.97-2.10 (3H, m), 2.17 (1H, td, J=7.3, 14.2 Hz), 3.69 (2H, t, J=6.9 Hz), 3.78-3.93 (2H, m), 3.98 (2H, d, J=2.0 Hz), 4.20 (4H, d, J=2.0 Hz), 5.74 (1H, s), 6.61 (1H, d, J=1.3 Hz), 6.77 (1H, d, J=7.6

Hz), 6.81 (1H, dd, J=1.6, 8.6 Hz), 6.89-7.01 (5H, m), 7.13-7.23 (3H, m), 7.37 (1H, dd, J=7.6, 8.6 Hz), 7.45 (1H, dt, J=2.0, 8.2 Hz), 7.68 (1H, d, J=8.6 Hz), 8.02 (1H, d, J=7.6 Hz), 9.00 (1H, s).

Example 29

Preparation of 3-(3-{3-[3-benzyl-8-(trifluoromethyl)quinolin-4-yl]phenoxy}propyl)-5-(2,3-dihydrobenzofuran-5-yl)-5-methylimidazolidine-2,4-dione

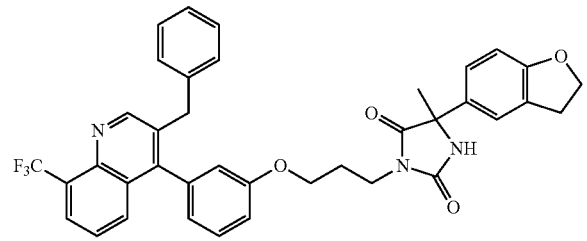

5-(2,3-dihydrobenzofuran-5-yl)-5-methylimidazolidine-2,4-dione was used in place of 5-(benzo[d][1,3]dioxol-5-yl)-5-methylimidazolidine-2,4-dione of Example 25c) for a similar reaction and treatment, and the title compound was obtained as a colorless oil.

$^1$H-NMR (CDCl$_3$) δ: 1.76 (3H, s), 2.10 (2H, t, J=6.6 Hz), 3.15 (2H, t, J=8.9 Hz), 3.71 (2H, t, J=7.3 Hz), 3.84-3.94 (2H, m), 3.97 (2H, d, J=2.6 Hz), 4.54 (2H, t, J=8.9 Hz), 5.69 (1H, s), 6.63 (1H, d, J=2.3 Hz), 6.72 (1H, d, J=8.2 Hz), 6.77 (1H, d, J=6.9 Hz), 6.92-7.00 (3H, m), 7.14-7.23 (5H, m), 7.34 (1H, dd, J=7.3, 8.6 Hz), 7.45 (1H, dt, J=1.0, 7.3 Hz), 7.67 (1H, d, J=8.6 Hz), 8.01 (1H, J=7.3 Hz), 9.00 (1H, s).

Example 30

Preparation of 3-(3-{3-[3-benzyl-8-(trifluoromethyl)quinolin-4-yl]phenoxy}propyl-5-methyl-5-(quinoxalin-6-yl)imidazolidine-2,4-dione

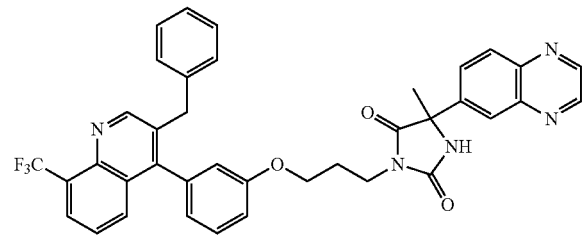

5-methyl-5-(quinoxalin-6-yl)imidazolidine-2,4-dione was used in place of 5-(benzo[d][1,3]dioxol-5-yl)-5-methylimidazolidine-2,4-dione of Example 25c) for a similar reaction and treatment, and the title compound was obtained as a colorless oil.

$^1$H-NMR (CDCl$_3$) δ: 1.94 (3H, d, J=2.0 Hz), 2.11 (2H, quintet, J=6.9 Hz), 3.76 (2H, t, J=6.9 Hz), 3.80-3.92 (2H, m), 3.96 (2H, d, J=2.6 Hz), 6.07 (1H, s), 6.60 (1H, s), 6.74 (1H, d, J=8.6 Hz), 6.91 (1H, dd, J=2.0, 8.6 Hz), 6.94-6.98 (2H, m), 7.13-7.20 (4H, m), 7.32 (1H, dd, J=6.9, 8.2 Hz), 7.65 (1H, d, J=8.2 Hz), 7.92-8.04 (2H, m), 8.11 (1H, dd, J=3.0, 8.9 Hz), 8.23 (1H, d, J=2.0 Hz), 8.84 (2H, dd, J=1.7, 3.6 Hz), 8.99 (1H, s).

Example 31

Preparation of 3-(3-{3-[3-benzyl-8-(trifluoromethyl)quinolin-4-yl]phenoxy}propyl)-5-(4-isopropoxyphenyl)-5-methylimidazolidine-2,4-dione

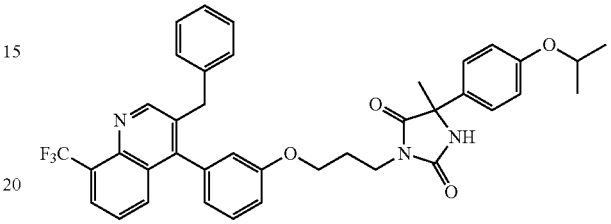

5-(4-isopropoxyphenyl)-5-methylimidazolidine-2,4-dione was used in place of 5-(benzo[d][1,3]dioxol-5-yl)-5-methylimidazolidine-2,4-dione of Example 25c) for a similar reaction and treatment, and the title compound was obtained as a colorless oil.

$^1$H-NMR (CDCl$_3$) δ: 1.31 (6H, t, J=6.3 Hz), 1.77 (3H, s), 2.09 (2H, tt, J=6.3, 7.3 Hz), 3.71 (2H, t, J=7.3 Hz), 3.82-3.92 (2H, m), 3.98 (2H, d, J=2.6 Hz), 4.49 (1H, septet, J=6.3 Hz), 5.63 (1H, d, J=4.3 Hz), 6.63 (1H, d, J=1.3 Hz), 6.77 (1H, d, J=7.6 Hz), 6.83 (2H, dd, J=2.3, 8.2 Hz), 6.93 (1H, d, J=2.6 Hz), 6.98 (2H, d, J=2.0, 8.2 Hz), 7.12-7.22 (3H, m), 7.31 (2H, dd, J=1.3, 8.6 Hz), 7.37 (1H, dd, J=6.9, 7.3 Hz), 7.45 (1H, dt, J=3.3, 8.2 Hz), 7.68 (1H, d, J=7.3 Hz), 8.01 (1H, d, J=6.9 Hz), 9.00 (1H, s).

Example 32

Preparation of 3-(3-{3-[3-benzyl-8-(trifluoromethyl)quinolin-4-yl]phenoxy}propyl)-5-(3-fluoro-4-isopropoxyphenyl)-5-methylimidazolidine-2,4-dione

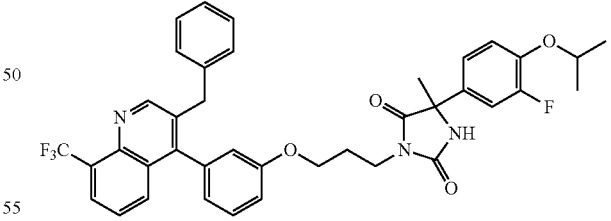

5-(3-fluoro-4-isopropoxyphenyl)-5-methylimidazolidine-2,4-dione was used in place of 5-(benzo[d][1,3]dioxol-5-yl)-5-methylimidazolidine-2,4-dione of Example 25c) for a similar reaction and treatment, and the title compound was obtained as a colorless oil.

$^1$H-NMR (CDCl$_3$) δ: 1.33 (6H, d, J=5.9 Hz), 1.76 (3H, s), 2.09 (2H, quintet, J=6.9 Hz), 3.71 (2H, t, J=6.9 Hz), 3.84-3.94 (2H, m), 3.98 (2H, d, J=2.6 Hz), 4.49 (1H, septet, J=5.9 Hz), 5.77 (1H, d, J=5.6 Hz), 6.64 (1H, s), 6.78 (1H, d, J=7.6 Hz), 6.89 (1H, dd, J=3.6, 8.6 Hz), 6.92-6.99 (3H, m), 7.09-7.27

(5H, m), 7.38 (1H, dd, J=6.9, 7.6 Hz), 7.46 (1H, d, J=6.3 Hz), 7.68 (1H, d, J=7.6 Hz), 8.02 (1H, d, J=6.9 Hz), 9.00 (1H, s).

Example 33

Preparation of 3-(3-{3-[3-benzyl-8-(trifluoromethyl)quinolin-4-yl]phenoxy}propyl)-5-ethyl-5-(3-fluoro-4-isopropoxyphenyl)imidazolidine-2,4-dione

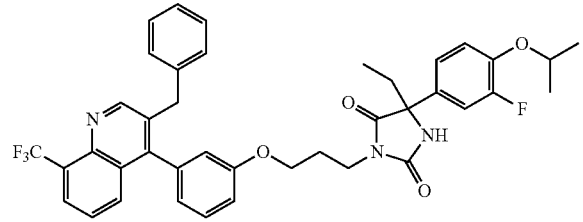

5-ethyl-5-(3-fluoro-4-isopropoxyphenyl)imidazolidine-2,4-dione was used in place of 5-(benzo[d][1,3]dioxol-5-yl)-5-methylimidazolidine-2,4-dione of Example 25c) for a similar reaction and treatment, and the title compound was obtained as a colorless oil.

¹H-NMR (CDCl₃) δ: 0.87 (3H, t, J=7.3 Hz), 1.33 (6H, d, J=5.9 Hz), 1.97-2.10 (3H, m), 2.17 (1H, qd, J=7.3, 14.8 Hz), 3.69 (2H, t, J=7.3 Hz), 3.81-3.87 (2H, m), 3.98 (2H, d, J=2.6 Hz), 4.49 (1H, septet, J=5.9 Hz), 6.14 (1H, s), 6.63 (1H, s), 6.77 (1H, d, J=7.6 Hz), 6.86-6.99 (4H, m), 7.14-7.23 (5H, m), 7.37 (1H, t, J=7.6 Hz), 7.45 (1H, dd, J=7.3, 8.2 Hz), 7.68 (1H, d, J=8.2 Hz), 8.02 (1H, d, J=7.3 Hz), 9.00 (1H, s).

Example 34

Preparation of 3-(3-{3-[3-benzyl-8-(trifluoromethyl)quinolin-4-yl]phenoxy}propyl)-5-(6-isopropoxypyridin-3-yl)-5-methylimidazolidine-2,4-dione

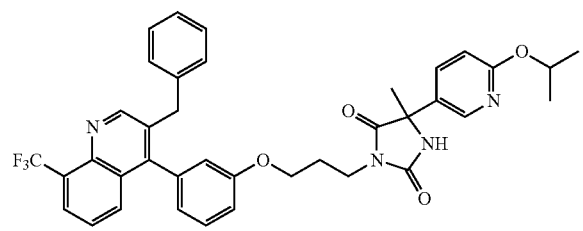

5-(6-isopropoxypyridin-3-yl)-5-methylimidazolidine-2,4-dione was used in place of 5-(benzo[d][1,3]dioxol-5-yl)-5-methylimidazolidine-2,4-dione of Example 25c) for a similar reaction and treatment, and the title compound was obtained as a colorless oil.

¹H-NMR (CDCl₃) δ: 1.31 (6H, d, J=5.9 Hz), 1.76 (3H, s), 2.09 (2H, quintet, J=6.9 Hz), 3.71 (2H, t, J=6.9 Hz), 3.82-3.93 (2H, m), 3.98 (2H, d, J=2.4 Hz), 5.24 (1H, septet, J=5.9 Hz), 6.62-6.66 (2H, m), 6.78 (1H, d, J=7.6 Hz), 6.91-6.99 (3H, m), 7.13-7.23 (3H, m), 7.37 (1H, dd, J=6.9, 7.6 Hz), 7.46 (1H, d, J=7.6 Hz), 7.61-7.70 (2H, m), 8.01 (1H, d, J=6.9 Hz), 8.21 (1H, s), 9.00 (1H, s).

Example 35

Preparation of 5-(benzo[d][1,3]dioxol-5-yl)-3-(4-{3-[3-benzyl-8-(trifluoromethyl)quinolin-4-yl]phenoxy}butyl)-5-methylimidazolidine-2,4-dione

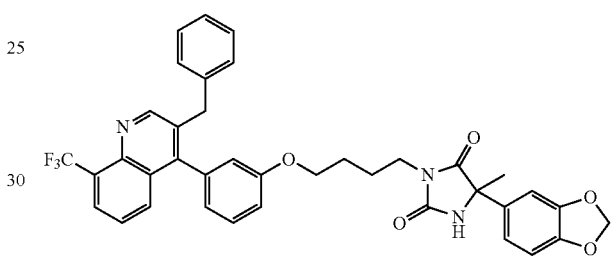

1,4-dibromobutane was used in place of 1,3-dibromopropane for a reaction and treatment in Example 25b) and then for a similar reaction and treatment as Example 25c). The title compound was obtained as a colorless oil.

¹H-NMR (CDCl₃) δ: 1.69-1.86 (7H, m), 3.57 (2H, t, J=6.6 Hz), 3.77-3.92 (2H, m), 3.98 (2H, d, J=3.6 Hz), 5.79 (1H, s), 5.94 (2H, s), 6.63 (1H, s), 6.78 (2H, d, J=7.9 Hz), 6.92 (1H, dd, J=2.0, 8.2 Hz), 6.95-6.99 (4H, m), 7.10-7.20 (3H, m), 7.36 (1H, dd, J=6.9, 7.6 Hz), 7.46 (1H, d, J=7.9 Hz), 7.68 (1H, d, J=7.6 Hz), 8.01 (1H, d, J=6.9 Hz), 9.00 (1H, s).

Example 36

Preparation of 5-(benzo[d][1,3]dioxol-5-yl)-3-(4-{3-[3-benzyl-8-(trifluoromethyl)quinolin-4-yl]phenoxy}butyl)-5-ethylimidazolidine-2,4-dione

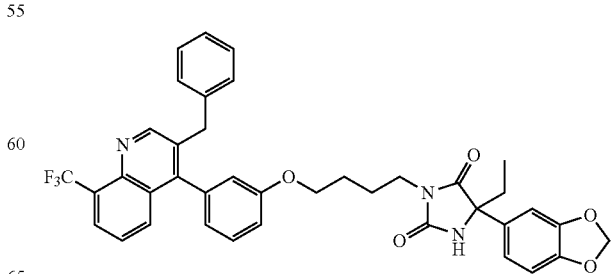

5-(benzo[d][1,3]dioxol-5-yl)-5-ethylimidazolidine-2,4-dione was used in place of 5-(benzo[d][1,3]dioxol-5-yl)-5-methylimidazolidine-2,4-dione in Example 35 for a similar reaction and treatment, and the title compound was obtained as a colorless oil.

$^1$H-NMR (CDCl$_3$) δ: 0.87 (3H, t, J=7.3 Hz), 1.66-1.82 (4H, m), 2.04 (1H, qd, J=7.3, 14.5 Hz), 2.18 (1H, qd, J=7.3, 14.5 Hz), 3.56 (2H, t, J=6.6 Hz), 3.76-3.92 (2H, m), 3.97 (2H, d, J=3.6 Hz), 5.94 (2H, d, J=2.0), 6.08 (1H, s), 6.62 (1H, s), 6.78 (2H, d, J=8.2 Hz), 6.95 (1H, dd, J=1.3, 8.2 Hz), 6.97-6.99 (3H, m), 7.02 (1H, d, J=1.3 Hz), 7.12-7.21 (3H, m), 7.38 (1H, dd, J=7.3, 8.6 Hz), 7.46 (1H, d, J=7.6 Hz), 7.68 (1H, d, J=8.6 Hz), 8.01 (1H, d, J=7.3 Hz), 9.00 (1H, s).

Example 37

Preparation of 3-(4 {3-[3-benzyl-8-(trifluoromethyl) quinolin-4-yl]phenoxy}butyl)-5-(2,3-dihydrobenzo [b][1,4]dioxin-6-yl)-5-methylimidazolidine-2,4-dione

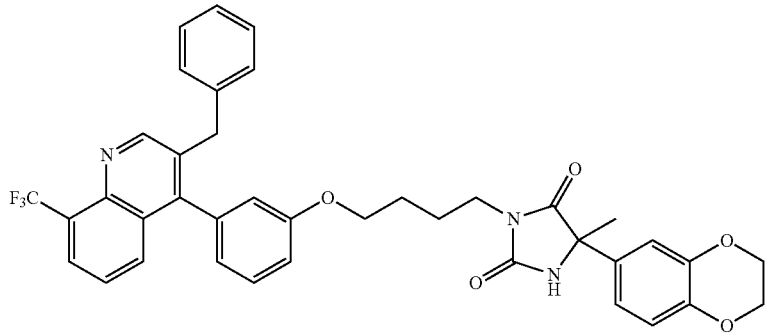

5-(2,3-dihydrobenzo[b][1,4]dioxin-6-yl)-5-methylimidazolidine-2,4-dione was used in place of 5-(benzo[d][1,3]dioxol-5-yl)-5-methylimidazolidine-2,4-dione in Example 35 for a similar reaction and treatment, and the title compound was obtained as a colorless oil.

$^1$H-NMR (CDCl$_3$) δ: 1.70-1.82 (7H, m), 3.56 (2H, t, J=6.6 Hz), 3.76-3.92 (2H, m), 3.98 (2H, d, J=3.6 Hz), 4.21 (4H, s), 5.79 (1H, s), 6.62 (1H, t, J=1.3 Hz), 6.77 (1H, d, J=7.6 Hz), 6.85 (1H, d, J=8.6 Hz), 6.91 (1H, dd, J=2.3, 8.6 Hz), 6.95-7.00 (4H, m), 7.12-7.23 (3H, m), 7.38 (1H, dd, J=7.6, 8.9 Hz), 7.46 (1H, d, J=7.6 Hz), 7.68 (1H, d, J=8.9 Hz), 8.01 (1H, d, J=6.6 Hz), 9.00 (1H, s).

Example 38

Preparation of 3-(4-{3-[3-benzyl-8-(trifluoromethyl) quinolin-4-yl]phenoxy}butyl)-5-(2,3-dihydrobenzo [b][1,4]dioxin-6-yl)-5-ethylimidazolidine-2,4-dione

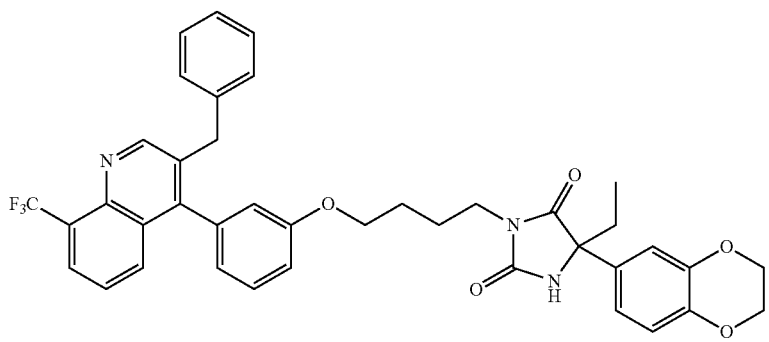

5-(2,3-dihydrobenzo[b][1,4]dioxin-6-yl)-5-ethylimidazolidine-2,4-dione was used in place of 5-(benzo[d][1,3]dioxol-5-yl)-5-methylimidazolidine-2,4-dione in Example 35 for a similar reaction and treatment, and the title compound was obtained as a colorless oil.

$^1$H-NMR (CDCl$_3$) δ: 0.89 (3H, t, J=7.3 Hz), 1.69-1.81 (4H, m), 2.04 (1H, qd, J=7.3, 14.2 Hz), 2.19 (1H, qd, J=7.3, 14.2 Hz), 3.55 (2H, t, J=6.3 Hz), 3.76-3.92 (2H, m), 3.98 (2H, d, J=4.0 Hz), 4.22 (4H, s), 5.91 (1H, s), 6.62 (1H, s), 6.77 (1H, d, J=7.6 Hz), 6.89 (1H, d, J=8.6 Hz), 6.92-6.99 (4H, m), 7.01 (1H, d, J=2.3 Hz), 7.09-7.20 (3H, m), 7.38 (1H, dd, J=7.3, 8.2 Hz), 7.46 (1H, d, J=7.6 Hz), 7.68 (1H, d, J=8.2 Hz), 8.01 (1H, d, J=7.3 Hz), 9.00 (1H, s).

Example 39

Preparation of 3-(4-{3-[3-benzyl-8-(trifluoromethyl)quinolin-4-yl]phenoxy}butyl)-5-(2,3-dihydrobenzofuran-5-yl)-5-methylimidazolidine-2,4-dione

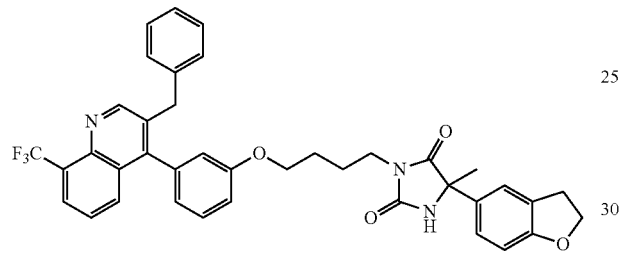

5-(2,3-dihydrobenzofuran-5-yl)-5-methylimidazolidine-2,4-dione was used in place of 5-(benzo[d][1,3]dioxol-5-yl)-5-methylimidazolidine-2,4-dione in Example 35 for a similar reaction and treatment, and the title compound was obtained as a colorless oil.

$^1$H-NMR (CDCl$_3$) δ: 1.69-1.82 (7H, m), 3.19 (2H, t, J=8.2 Hz), 3.57 (2H, t, J=6.6 Hz), 3.78-3.92 (2H, m), 3.98 (2H, d, J=3.3 Hz), 4.56 (2H, t, J=8.6 Hz), 5.71 (1H, s), 6.63 (1H, s), 6.75 (1H, d, J=8.6 Hz), 6.77 (1H, d, J=7.6 Hz), 6.95-6.99 (3H, m), 7.12-7.20 (4H, m), 7.29 (1H, s), 7.39 (1H, dd, J=7.3, 8.2 Hz), 7.46 (1H, d, J=7.6 Hz), 7.68 (1H, d, J=8.2 Hz), 8.01 (1H, d, J=7.3 Hz), 9.00 (1H, s).

Example 40

Preparation of 3-(4-{3-[3-benzyl-8-(trifluoromethyl)quinolin-4-yl]phenoxy}butyl)-5-(4-isopropoxyphenyl)-5-methylimidazolidine-2,4-dione

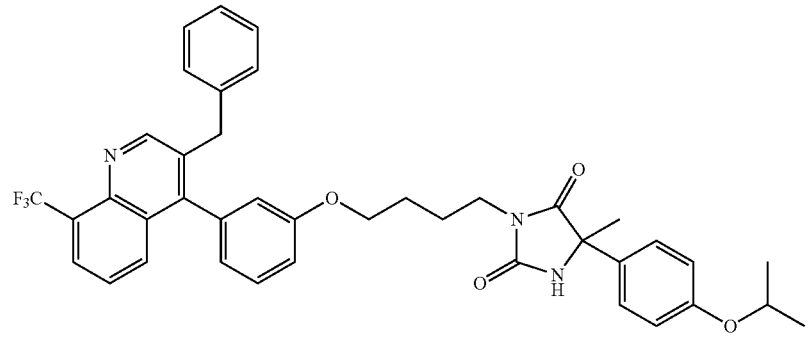

5-(4-isopropoxyphenyl)-5-methylimidazolidine-2,4-dione was used in place of 5-(benzo[d][1,3]dioxol-5-yl)-5-methylimidazolidine-2,4-dione in Example 35 for a similar reaction and treatment, and the title compound was obtained as a colorless oil.

$^1$H-NMR (CDCl$_3$) δ: 1.31 (6H, d, J=6.3 Hz), 1.71-1.89 (7H, m), 3.57 (2H, t, J=5.9 Hz), 3.77-3.92 (2H, m), 3.98 (2H, d, J=3.6 Hz), 4.52 (1H, septet, J=6.3 Hz), 5.74 (1H, s), 6.63 (1H, s), 6.77 (1H, d, J=7.3 Hz), 6.87 (2H, d, J=8.9 Hz), 6.94-6.99 (3H, m), 7.09-7.22 (3H, m), 7.35 (2H, d, J=8.9 Hz), 7.38 (1H, dd, J=6.6, 8.2 Hz), 7.46 (1H, d, J=7.6 Hz), 7.68 (1H, d, J=8.2 Hz), 8.01 (1H, d, J=6.6 Hz), 9.00 (1H, s).

Example 41

Preparation of 5-(benzo[d][1,3]dioxol-5-yl)-3-(5-{3-[3-benzyl-8-(trifluoromethyl)quinolin-4-yl]phenoxy}pentyl)-5-methylimidazolidine-2,4-dione

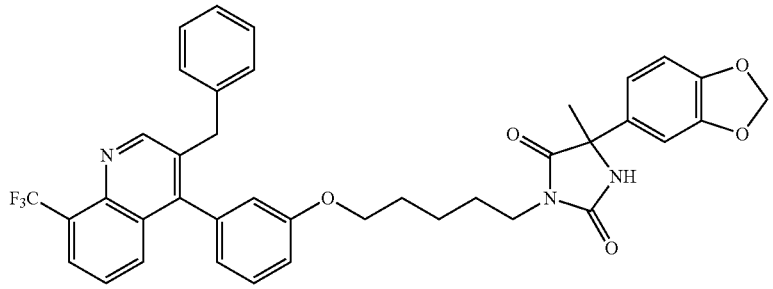

1,5-dibromopentane was used in place of 1,3-dibromopropane for a reaction and treatment in Example 25 b) and then for a similar reaction and treatment as Example 25 c). The title compound was obtained as a colorless oil.

$^1$H-NMR (CDCl$_3$) δ: 1.43 (2H, quintet, J=8.2 Hz), 1.58-1.74 (4H, m), 1.77 (3H, s), 3.53 (2H, t, J=7.3 Hz), 3.76 (1H, td, J=6.6, 9.2 Hz), 3.83 (1H, td, J=6.6, 9.2 Hz), 3.97 (1H, dd, J=4.6, 14.2 Hz), 3.99 (1H, dd, J=4.6, 14.2 Hz), 5.85 (1H, s), 5.93 (2H, s), 6.63 (1H, s), 6.75-6.79 (2H, m), 6.89-6.99 (5H, m), 7.07-7.20 (3H, m), 7.39 (1H, dd, J=6.9, 8.2 Hz), 7.46 (1H, d, J=7.6 Hz), 7.69 (1H, d, J=8.2 Hz), 8.01 (1H, d, J=6.9 Hz), 9.00 (1H, s).

Example 42

Preparation of 5-(benzo[d][1,3]dioxol-5-yl)-3-(5-{3-[3-benzyl-8-(trifluoromethyl)quinolin-4-yl]phenoxy}pentyl)-5-methylimidazolidine-2,4-dione

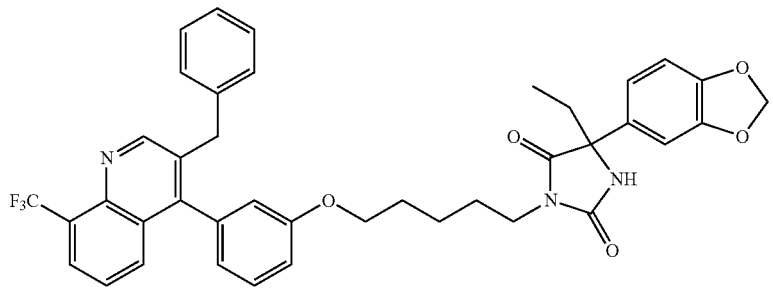

5-(benzo[d][1,3]dioxol-5-yl)-5-ethylimidazolidine-2,4-dione was used in place of 5-(benzo[d][1,3]dioxol-5-yl)-5-methylimidazolidine-2,4-dione in Example 41 for a similar reaction and treatment, and the title compound was obtained as a colorless oil.

$^1$H-NMR (CDCl$_3$) δ: 0.88 (3H, t, J=7.3 Hz), 1.35-1.49 (2H, m), 1.58-1.79 (4H, m), 2.03 (1H, qd, J=6.9, 14.2 Hz), 2.14 (1H, qd, J=6.9, 14.2 Hz), 3.51 (2H, t, J=6.9 Hz), 3.76 (1H, td, J=6.6, 9.2 Hz), 3.82 (1H, td, J=6.6, 9.2 Hz), 3.97 (1H, dd, J=4.0, 15.5 Hz), 3.99 (1H, dd, J=4.0, 15.5 Hz), 5.92-5.94 (3H, m), 6.62 (1H, s), 6.75-6.79 (2H, m), 6.92-7.02 (5H, m), 7.13-7.20 (3H, m), 7.39 (1H, dd, J=7.3, 7.9 Hz), 7.46 (1H, d, J=7.9 Hz), 7.69 (1H, d, J=7.9 Hz), 8.01 (1H, d, J=7.3 Hz), 9.00 (1H, s).

Example 43

Preparation of 3-(5-{3-[3-benzyl-8-(trifluoromethyl)quinolin-4-yl]phenoxy}pentyl)-5-(2,3-dihydrobenzo[b][1,4]dioxin-6-yl)-5-ethylimidazolidine-2,4-dione

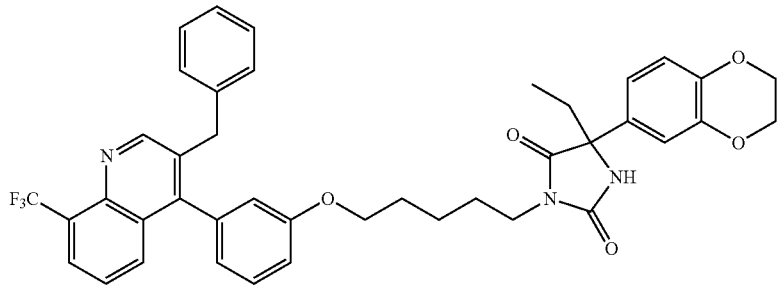

5-(2,3-dihydrobenzo[b][1,4]dioxin-6-yl)-5-ethylimidazolidine-2,4-dione was used in place of 5-(benzo[d][1,3]dioxol-5-yl)-5-methylimidazolidine-2,4-dione in Example 41 for a similar reaction and treatment, and the title compound was obtained as a colorless oil.

$^1$H-NMR (CDCl$_3$) δ: 0.88 (3H, t, J=7.3 Hz), 1.35-1.49 (2H, m), 1.58-1.79 (4H, m), 2.02 (1H, qd, J=7.3, 14.2 Hz), 2.15 (1H, qd, J=7.3, 14.2 Hz), 3.50 (2H, t, J=6.9 Hz), 3.76 (1H, td, J=6.3, 9.2 Hz), 3.81 (1H, td, J=6.3, 9.2 Hz), 3.97 (1H, dd, J=3.6, 14.8 Hz), 3.99 (1H, dd, J=3.6, 14.8 Hz), 4.21 (4H, s), 5.87 (1H, s), 6.62 (1H, s), 6.77 (1H, d, J=7.6 Hz), 6.84 (1H, d, J=8.6 Hz), 6.91-7.02 (5H, m), 7.13-7.22 (3H, m), 7.39 (1H, dd, J=7.3, 8.2 Hz), 7.46 (1H, d, J=7.9 Hz), 7.69 (1H, d, J=8.2 Hz), 8.01 (1H, d, J=7.3 Hz), 9.00 (1H, s).

Example 44

Preparation of 3-(5-{3-[3-benzyl-8-(trifluoromethyl)quinolin-4-yl]phenoxy}pentyl)-5-(4-isopropoxyphenyl)-5-methylimidazolidine-2,4-dione

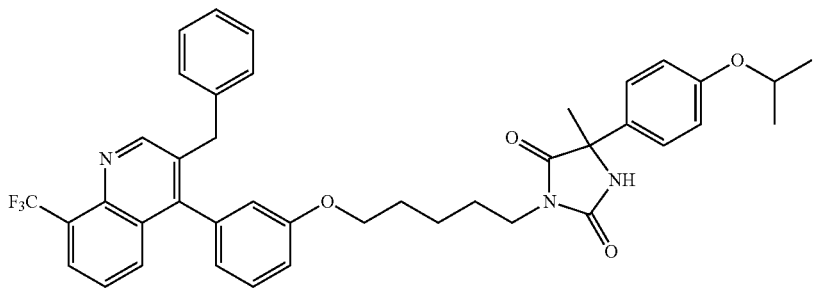

5-(4-isopropoxyphenyl)-5-methylimidazolidine-2,4-dione was used in place of 5-(benzo[d][1,3]dioxol-5-yl)-5-methylimidazolidine-2,4-dione in Example 41 for a similar reaction and treatment, and the title compound was obtained as a colorless oil.

$^1$H-NMR (CDCl$_3$) δ1.31 (6H, d, J=5.2 Hz), 1.38-1.50 (2H, m), 1.58-1.74 (4H, m), 1.79 (3H, s), 3.53 (2H, t, J=7.3 Hz), 3.76 (1H, td, J=6.3, 9.2 Hz), 3.83 (1H, td, J=6.3, 9.2 Hz), 3.96 (1H, dd, J=3.6, 13.5 Hz), 3.99 (1H, dd, J=3.6, 13.5 Hz), 4.51 (1H, septet, J=5.9 Hz), 5.75 (1H, s), 6.63 (1H, s), 6.77 (1H, d, J=7.3 Hz), 6.86 (2H, d, J=8.2 Hz), 6.96-7.00 (3H, m), 7.10-7.20 (3H, m), 7.35 (2H, d, J=8.2 Hz), 7.39 (1H, dd, J=7.3, 7.6 Hz), 7.46 (1H, d, J=7.9 Hz), 7.69 (1H, d, J=7.6 Hz), 8.01 (1H, d, J=7.3 Hz), 9.00 (1H, s).

Example 45

Preparation of 5-(benzo[d][1,3]dioxol-5-yl)-3-(3-{4-[3-benzyl-8-(trifluoromethyl)quinolin-4-yl]phenoxy}propyl)-5-methylimidazolidine-2,4-dione

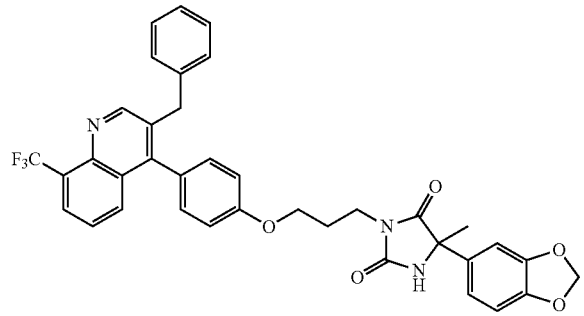

4-hydroxyphenylboronic acid was used in place of 3-hydroxyphenylboronic acid for a reaction and treatment in Example 25 a) and then for a similar reaction and treatment as Example 25b) and c). The title compound was obtained as a colorless oil.

$^1$H-NMR (CDCl$_3$) δ: 1.81 (3H, s), 2.18 (2H, tt, J=5.9, 6.9 Hz), 3.78 (2H, t, J=6.9 Hz), 3.98 (2H, s), 4.06 (2H, t, J=5.9 Hz), 5.81 (1H, s), 5.93 (2H, s), 6.79 (1H, d, J=7.9 Hz), 6.91-6.99 (6H, m), 7.07 (2H, d, J=8.6 Hz), 7.13-7.23 (3H, m), 7.45 (1H, dd, J=7.3, 8.2 Hz), 7.69 (1H, d, J=8.2 Hz), 8.01 (1H, d, J=7.3 Hz), 8.99 (1H, s).

Example 46

Preparation of 5-(benzo[d][1,3]dioxol-5-yl)-3-(3-{4-[3-benzyl-8-(trifluoro methyl)quinolin-4-yl]phenoxy}propyl)-5-ethylimidazolidine-2,4-dione

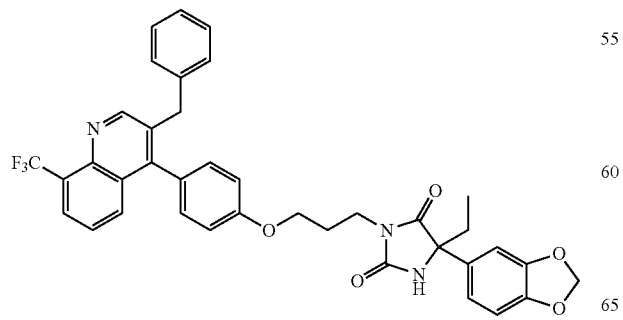

5-(benzo[d][1,3]dioxol-5-yl)-5-ethylimidazolidine-2,4-dione was used in place of 5-(benzo[d][1,3]dioxol-5-yl)-5-methylimidazolidine-2,4-dione in Example 45 for a similar reaction and treatment, and the title compound was obtained as a colorless oil.

$^1$H-NMR (CDCl$_3$) δ: 0.91 (3H, t, J=7.3 Hz), 2.07 (1H, qd, J=7.3, 14.2 Hz), 2.12-2.26 (3H, m), 3.77 (2H, t, J=6.9 Hz), 3.98 (2H, s), 4.04 (2H, t, J=5.9 Hz), 5.92 (1H, d, J=1.3 Hz), 5.93 (1H, d, J=1.3 Hz), 6.09 (1H, s), 6.79 (1H, d, J=7.9 Hz), 6.89-6.99 (5H, m), 7.03-7.09 (3H, m), 7.13-7.24 (3H, m), 7.44 (1H, dd, J=7.3, 7.9 Hz), 7.69 (1H, d, J=7.9 Hz), 8.01 (1H, d, J=7.3 Hz), 8.99 (1H, s).

Example 47

Preparation of 3-(3-{4-[(3-benzyl-8-(trifluoromethyl)quinolin-4-yl]phenoxy}propyl)-5-(2,3-dihydrobenzo[b][1,4]dioxin-6-yl)-5-ethylimidazolidine

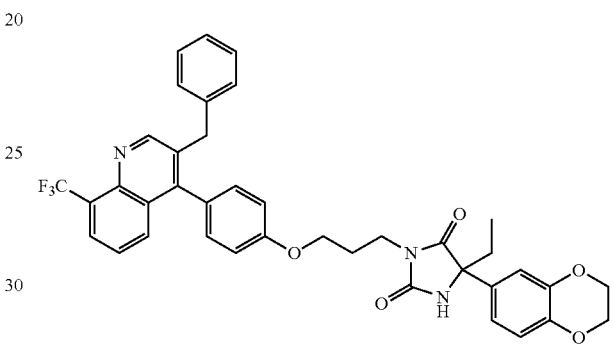

5-(2,3-dihydrobenzo[b][1,4]dioxin-6-yl)-5-ethylimidazolidine-2,4-dione was used in place of 5-(benzo[d][1,3]dioxol-5-yl)-5-methylimidazolidine-2,4-dione in Example 45 for a similar reaction and treatment, and the title compound was obtained as a colorless oil.

$^1$H-NMR (CDCl$_3$) δ: 0.91 (3H, t, J=7.1 Hz), 2.06 (1H, qd, J=7.1, 13.8 Hz), 2.13-2.24 (3H, m), 3.76 (2H, t, J=6.6 Hz), 3.98 (2H, s), 4.04 (2H, t, J=5.9 Hz), 4.21 (4H, s), 5.83 (1H, s), 6.87 (1H, dd, J=1.0, 8.6 Hz), 6.91-6.99 (5H, m), 7.04 (1H, dd, J=1.0, 2.3 Hz), 7.06 (2H, d, J=7.6 Hz), 7.13-7.24 (3H, m), 7.44 (1H, dd, J=6.6, 8.6 Hz), 7.70 (1H, d, J=8.6 Hz), 7.84 (1H, d, J=6.6 Hz), 8.99 (1H, s).

Example 48

Preparation of 3-(3-{4-[3-benzyl-8-(trifluoromethyl)quinolin-4-yl]phenoxy}propyl)-5-(4-isopropoxyphenyl)-5-methylimidazolidine-2,4-dione

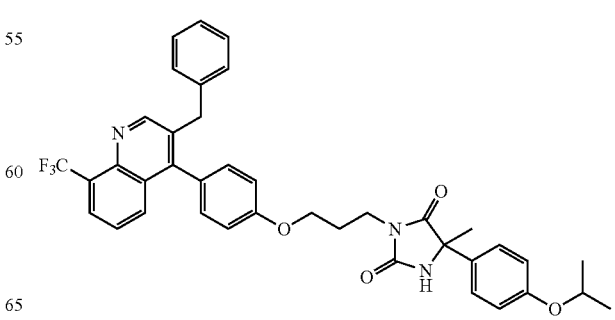

5-(4-isopropoxyphenyl)-5-methylimidazolidine-2,4-dione was used in place of 5-(benzo[d][1,3]dioxol-5-yl)-5-methylimidazolidine-2,4-dione in Example 45 for a similar reaction and treatment, and the title compound was obtained as a colorless oil.

¹H-NMR (CDCl₃) δ: 1.29 (6H, d, J=6.3 Hz), 1.82 (3H, s), 2.18 (2H, tt, J=5.9, 6.9 Hz), 3.78 (2H, t, J=6.9 Hz), 3.98 (2H, s), 4.06 (2H, t, J=5.9 Hz), 4.51 (1H, q, J=6.3 Hz), 5.76 (1H, s), 6.87 (2H, d, J=8.6 Hz), 6.91-6.98 (4H, m), 7.07 (2H, d, J=8.2 Hz), 7.13-7.23 (3H, m), 7.37 (2H, d, J=8.6 Hz), 7.44 (1H, dd, J=7.3, 8.2 Hz), 7.69 (1H, d, J=8.2 Hz), 8.00 (1H, d, J=7.3 Hz), 8.99 (1H, s).

Example 49

Preparation of 5-(benzo[d][1,3]dioxol-5-yl)-3-(4-{4-[3-benzyl-8-(trifluoromethyl)quinolin-4-yl]phenoxy}pentyl)-5-methylimidazolidine-2,4-dione

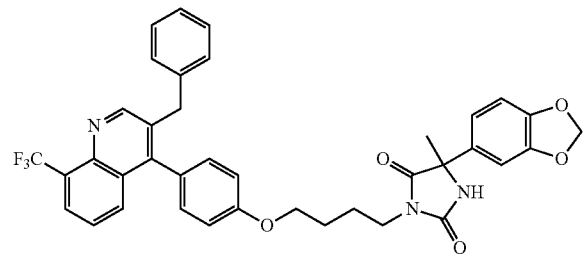

1,4-dibromobutane was used in place of 1,3-dibromopropane for a reaction and treatment in Example 45 and then for a similar reaction and treatment as Example 25c). The title compound was obtained as a colorless oil.

¹H-NMR (CDCl₃) δ: 1.81 (3H, s), 1.82-1.89 (4H, m), 3.63 (2H, t, J=6.6 Hz), 3.99 (2H, s), 4.05 (2H, t, J=5.6 Hz), 5.81 (1H, s), 5.96 (2H, s), 6.80 (1H, d, J=7.9 Hz), 6.93 (1H, d, J=2.0 Hz), 6.95-7.02 (5H, m), 7.09 (2H, d, J=8.9 Hz), 7.14-7.24 (3H, m), 7.44 (1H, dd, J=6.9, 8.6 Hz), 7.70 (1H, d, J=8.6 Hz), 8.00 (1H, d, J=6.9 Hz), 8.99 (1H, s).

Example 50

Preparation of 5-(benzo[d][1,3]dioxol-5-yl)-3-(4-{4-[3-benzyl-8-(trifluoro methyl)quinolin-4-yl]phenoxy}butyl)-5-ethylimidazolidine-2,4-dione

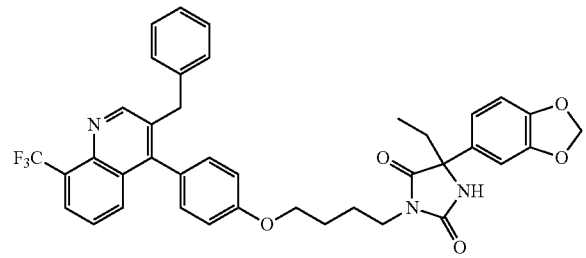

5-(benzo[d][1,3]dioxol-5-yl)-5-ethylimidazolidine-2,4-dione was used in place of 5-(benzo[d][1,3]dioxol-5-yl)-5-methylimidazolidine-2,4-dione in Example 49 for a similar reaction and treatment, and the title compound was obtained as a colorless oil.

¹H-NMR (CDCl₃) δ: 0.92 (3H, t, J=7.3 Hz), 179-1.88 (4H, m), 2.06 (1H, qd, J=7.3, 14.2 Hz), 2.21 (1H, qd, J=7.3, 14.2 Hz), 3.61 (2H, t, J=6.3 Hz), 3.98 (2H, s), 4.04 (2H, t, J=5.3 Hz), 5.95 (2H, s), 6.10 (1H, s), 6.80 (1H, d, J=7.9 Hz), 6.94-7.01 (5H, m), 7.05 (1H, d, J=1.0 Hz), 7.08 (2H, d, J=7.9 Hz), 7.14-7.24 (3H, m), 7.45 (1H, dd, J=7.3, 8.2 Hz), 7.69 (1H, d, J=8.2 Hz), 8.00 (1H, d, J=7.3 Hz), 8.98 (1H, s).

Example 51

Preparation of 3-(4-{4-[3-benzyl-8-(trifluoromethyl)quinolin-4-yl]phenoxy}butyl)-5-(2,3-dihydrobenzo[b][1,4]dioxin-6-yl)-5-ethylimidazolidine-2,4-dione

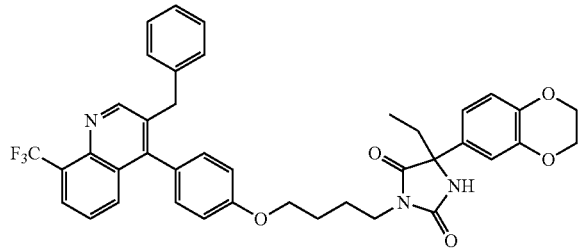

5-(2,3-dihydrobenzo[b][1,4]dioxin-6-yl)-5-ethylimidazolidine-2,4-dione was used in place of 5-(benzo[d][1,3]dioxol-5-yl)-5-methylimidazolidine-2,4-dione in Example 49 for a similar reaction and treatment, and the title compound was obtained as a colorless oil.

¹H-NMR (CDCl₃) δ: 0.92 (3H, t, J=7.3 Hz), 1.81-1.98 (4H, m), 2.06 (1H, qd, J=7.3, 14.5 Hz), 2.22 (1H, qd, J=7.3, 14.5 Hz), 3.61 (2H, t, J=6.3 Hz), 3.99 (2H, s), 4.04 (2H, t, J=5.3 Hz), 4.24 (4H, s), 5.93 (1H, s), 6.87 (1H, d, J=8.6 Hz), 6.94-7.01 (5H, m), 7.04 (1H, d, J=2.3 Hz), 7.08 (2H, d, J=8.6 Hz), 7.13-7.24 (3H, m), 7.44 (1H, dd, J=6.9, 8.2 Hz), 7.70 (1H, d, J=8.2 Hz), 8.00 (1H, d, J=6.9 Hz), 8.99 (1H, s).

Example 52

Preparation of 3-(4-{4-[3-benzyl-8-(trifluoromethyl)quinolin-4-yl]phenoxy}butyl)-5-(4-isopropoxyphenyl)-5-methylimidazolidine-2,4-dione

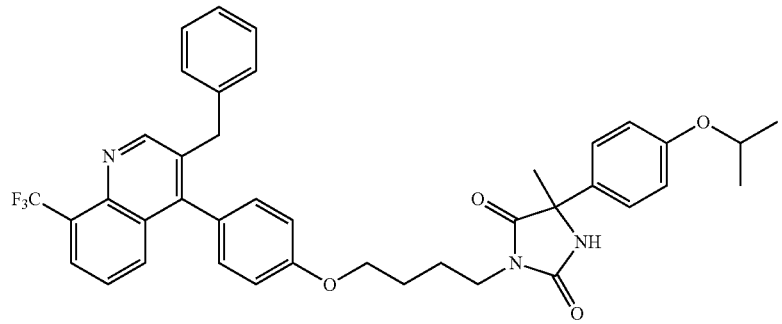

5-(4-isopropoxyphenyl)-5-methylimidazolidine-2,4-dione was used in place of 5-(benzo[d][1,3]dioxol-5-yl)-5-methylimidazolidine-2,4-dione in Example 49 for a similar reaction and treatment, and the title compound was obtained as a colorless oil.

$^1$H-NMR (CDCl$_3$) δ: 1.31 (6H, d, J=6.3 Hz), 1.82 (3H, s), 1.83-1.90 (4H, m), 3.63 (2H, t, J=6.6 Hz), 3.99 (2H, s), 4.04 (2H, t, J=5.6 Hz), 4.53 (1H, q, J=6.3 Hz), 5.77 (1H, s), 6.89 (2H, d, J=8.9 Hz), 6.95-7.00 (4H, m), 7.09 (2H, d, J=8.6 Hz), 7.12-7.24 (3H, m), 7.37 (2H, d, J=8.9 Hz), 7.44 (1H, dd, J=7.3, 8.2 Hz), 7.70 (1H, d, J=8.2 Hz), 8.00 (1H, d, J=7.3 Hz), 8.99 (1H, s).

Example 53

Preparation of 5-(benzo[d][1,3]dioxol-5-yl)-5-methyl-3-{6-[3-methyl-8-(trifluoromethyl)quinolin-4-yloxy]hexyl}imidazolidine-2,4-dione

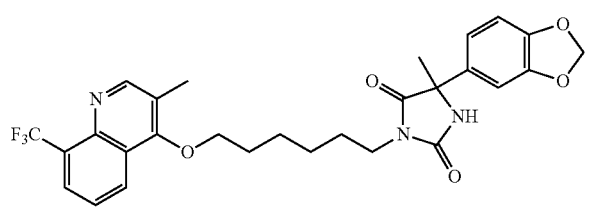

Ethyl propionate was used in place of ethyl benzoylacetate for a reaction and treatment in Example 1 a) and then for similar reactions and treatments as Example 1b), c), e), and f). The title compound was obtained as a colorless oil.

$^1$H-NMR (CDCl$_3$) δ: 1.35-1.46 (2H, m), 1.53-1.74 (4H, m), 1.78 (3H, m), 1.89 (2H, quintet, J=6.9 Hz), 2.45 (3H, m), 3.54 (2H, t, J=7.3 Hz), 4.03 (2H, t, J=6.6 Hz), 5.84 (1H, s), 5.94 (2H, s), 6.78 (1H, d, J=8.2 Hz), 6.93 (1H, dd, J=2.0, 8.2 Hz), 6.97 (1H, d, J=2.0 Hz), 7.56 (1H, dd, J=7.3, 8.2 Hz), 8.00 (1H, d, J=7.3 Hz), 8.26 (1H, d, J=8.2 Hz), 8.86 (1H, s).

Example 54

Preparation of 5-(4-isopropoxyphenyl)-5-methyl-3-{6-[3-methyl-8-(trifluoromethyl)quinolin-4-yloxy]hexyl}imidazolidine-2,4-dione

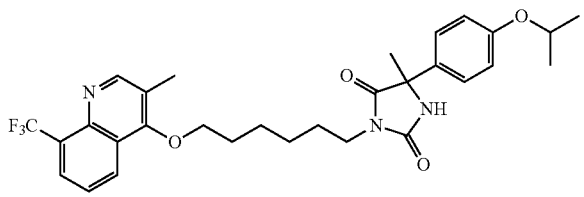

5-(4-isopropoxyphenyl)-5-methylimidazolidine-2,4-dione was used in place of 5-(benzo[d][1,3]dioxol-5-yl)-5-methylimidazolidine-2,4-dione in Example 53 for a similar reaction and treatment, and the title compound was obtained as a colorless oil.

$^1$H-NMR (CDCl$_3$) δ: 1.31 (6H, d, J=5.9 Hz), 1.36-1.46 (2H, m), 1.53-1.75 (4H, m), 1.80 (3H, s), 1.88 (2H, quintet, J=6.6 Hz), 2.45 (3H, s), 3.54 (2H, t, J=6.9 Hz), 4.03 (2H, t, J=6.6 Hz), 4.51 (1H, septet, J=5.9 Hz), 5.77 (1H, s), 6.86 (2H, d, J=8.9 Hz), 7.35 (2H, d, J=8.9 Hz), 7.56 (1H, dd, J=6.6, 8.2 Hz), 8.00 (1H, d, J=6.6 Hz), 8.27 (1H, d, J=8.2 Hz), 8.86 (1H, s).

Example 55

Preparation of 5-(benzo[d][1,3]dioxol-5-yl)-5-methyl-3-{6-[3-propyl-8-(trifluoromethyl)quinolin-4-yloxy]hexyl}imidazolidine-2,4-dione

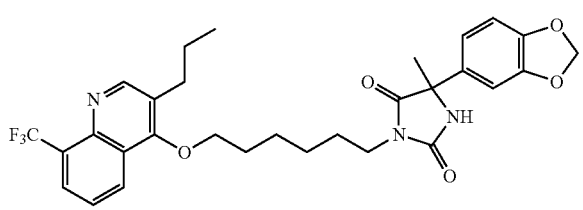

Ethyl valerate was used in place of ethyl benzoylacetate for a reaction and treatment in Example 1 a) and then for similar reactions and treatments as Example 1b), c), e), and f). The title compound was obtained as a colorless oil.

¹H-NMR (CDCl₃) δ: 1.01 (3H, t, J=7.3 Hz), 1.35-1.47 (2H, m), 1.54-1.74 (2H, m), 1.79 (3H, s), 1.90 (2H, quintet, J=6.6 Hz), 2.77 (2H, t, J=7.6 Hz), 3.54 (2H, t, J=7.3 Hz), 4.01 (2H, t, J=6.6 Hz), 5.91 (1H, s), 5.94 (2H, s), 6.79 (1H, d, J=8.2 Hz), 6.93 (1H, dd, J=2.0, 8.2 Hz), 6.97 (1H, d, J=2.0 Hz), 7.56 (1H, dd, J=6.9, 8.6 Hz), 8.00 (1H, d, J=6.9 Hz), 8.24 (1H, d, J=8.6 Hz), 8.89 (1H, s).

Example 56

Preparation of 5-(2,3-dihydrobenzo[b][1,4]dioxin-6-yl)-5-ethyl-3-{6-[3-propyl-8-(trifluoromethyl)quinolin-4-yloxy]hexyl}imidazolidine-2,4-dione

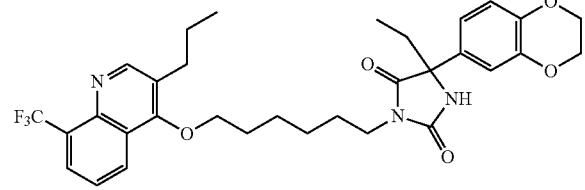

5-(2,3-dihydrobenzo[b][1,4]dioxin-6-yl)-5-ethylimidazolidine-2,4-dione was used in place of 5-(benzo[d][1,3]dioxol-5-yl)-5-methylimidazolidine-2,4-dione in Example 55 for a similar reaction and treatment, and the title compound was obtained as a colorless oil.

¹H-NMR (CDCl₃) δ: 0.89 (3H, t, J=7.3 Hz), 1.01 (3H, t, J=7.3 Hz), 1.35-1.46 (2H, m), 1.53-1.80 (6H, m), 1.89 (2H, quintet, J=6.6 Hz), 2.05 (1H, qd, J=7.3, 14.2 Hz), 2.20 (1H, qd, J=7.3, 14.2 Hz), 2.77 (2H, t, J=7.6 Hz), 3.52 (2H, t, J=7.3 Hz), 4.00 (2H, t, J=6.6 Hz), 4.22 (4H, s), 5.92 (1H, s), 6.85 (1H, d, J=8.6 Hz), 6.95 (1H, dd, J=2.0, 8.6 Hz), 7.02 (1H, d, J=2.0 Hz), 7.56 (1H, dd, J=6.9, 7.6 Hz), 8.00 (1H, d, J=6.6 Hz), 8.24 (1H, d, J=7.6 Hz), 8.89 (1H, s).

Example 57

Preparation of 5-(2,3-dihydrobenzofuran-5-yl)-5-methyl-3-{6-[3-propyl-8-(trifluoromethyl)quinolin-4-yloxy]hexyl}imidazolidine-2,4-dione

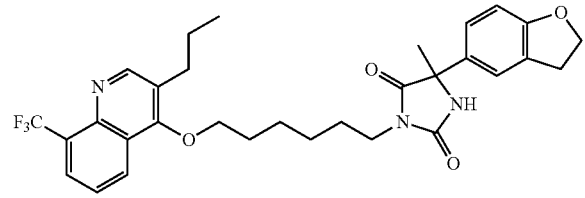

5-(2,3-dihydrobenzofuran-5-yl)-5-methylimidazolidine-2,4-dione was used in place of 5-(benzo[d][1,3]dioxol-5-yl)-5-methylimidazolidine-2,4-dione in Example 55 for a similar reaction and treatment, and the title compound was obtained as a colorless oil.

¹H-NMR (CDCl₃) δ: 1.04 (3H, t, J=7.3 Hz), 1.32-1.49 (2H, m), 1.52-1.95 (11H, m), 2.78 (2H, t, J=7.6 Hz), 3.20 (2H, t, J=8.6 Hz), 4.01 (2H, t, J=6.6 Hz), 4.57 (2H, t, J=8.6 Hz), 5.72 (1H, s), 6.76 (1H, d, J=8.6 Hz), 7.19 (1H, d, J=8.6 Hz), 7.31 (1H, s), 7.56 (1H, dd, J=6.9, 8.2 Hz), 8.01 (1H, d, J=6.9 Hz), 8.24 (1H, d, J=8.2 Hz), 8.89 (1H, s).

Example 58

Preparation of 5-(4-isopropoxyphenyl)-5-methyl-3-{6-[(3-propyl-8-(trifluoromethyl)quinolin-4-yloxy]hexyl}imidazolidine-2,4-dione

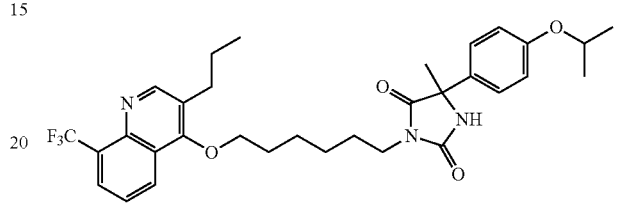

5-(4-isopropoxyphenyl)-5-methylimidazolidine-2,4-dione was used in place of 5-(benzo[d][1,3]dioxol-5-yl)-5-methylimidazolidine-2,4-dione in Example 55 for a similar reaction and treatment, and the title compound was obtained as a colorless oil.

¹H-NMR (CDCl₃) δ: 1.01 (3H, t, J=7.3 Hz), 1.31 (6H, d, J=5.9 Hz), 1.36-1.47 (2H, m), 1.54-1.77 (6H, m), 1.80 (3H, s), 1.90 (2H, quintet, J=6.6 Hz), 2.78 (2H, t, J=7.6 Hz), 3.54 (2H, t, J=7.3 Hz), 4.01 (2H, t, J=6.6 Hz), 4.51 (1H, septet, J=5.9 Hz), 5.80 (1H, s), 6.86 (2H, d, J=8.9 Hz), 7.35 (2H, d, J=8.9 Hz), 7.56 (1H, dd, J=6.9, 8.2 Hz), 8.00 (1H, d, J=6.9 Hz), 8.25 (1H, d, J=8.2 Hz), 8.89 (1H, s).

Example 59

Preparation of 5-(6-methoxy pyridin-3-yl)-5-methyl-3-{6-[3-propyl-8-(trifluoromethyl)quinolin-4-yloxy]hexyl}imidazolidine-2,4-dione

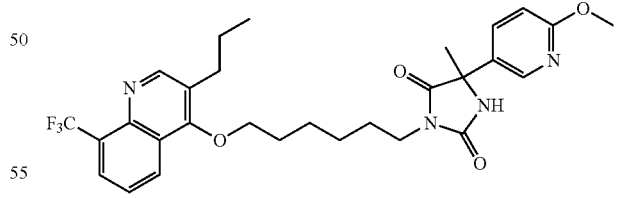

5-(6-methoxypyridin-3-yl)-5-methylimidazolidine-2,4-dione was used in place of 5-(benzo[d][1,3]dioxol-5-yl)-5-methylimidazolidine-2,4-dione in Example 55 for a similar reaction and treatment, and the title compound was obtained as a colorless oil.

¹H-NMR (CDCl₃) δ: 1.01 (3H, t, J=7.3 Hz), 1.32-1.47 (2H, m), 1.54-1.95 (11H, m), 2.78 (2H, t, J=7.6 Hz), 3.55 (2H, t, J=7.3 Hz), 3.91 (3H, s), 4.01 (2H, t, J=6.3 Hz), 6.03 (1H, s), 6.75 (1H, d, J=8.9 Hz), 7.56 (1H, t, J=7.9 Hz), 7.70 (1H, dd, J=2.6, 8.6 Hz), 8.01 (1H, d, J=7.3 Hz), 8.22-8.28 (2H, m), 8.89 (1H, s).

Example 60

Preparation of 5-(2,3-dihydrobenzofuran-5-yl)-5-methyl-3-(2-{2-[3-propyl-8-(trifluoromethyl)quinolin-4-yloxy]ethoxy}ethyl)imidazolidine-2,4-dione

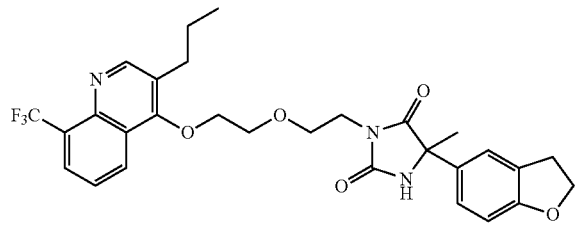

2-chloroethyl ether was used in place of 1,6-dibromohexane in Example 57 for a similar reaction and treatment, and the title compound was obtained as a colorless oil.

$^1$H-NMR (CDCl$_3$) δ: 1.01 (3H, t, J=7.3 Hz), 1.66-1.79 (5H, m), 2.78 (2H, d, J=7.3 Hz), 3.02 (2H, t, J=8.2 Hz), 3.83 (6H, s), 4.09 (2H, s), 4.44 (2H, t, J=8.2 Hz), 5.66 (1H, s), 6.64 (1H, d, J=8.2 Hz), 7.16 (1H, t, J=8.2 Hz), 7.26 (1H, s), 7.58 (1H, dd, J=6.6, 8.2 Hz), 8.00 (1H, d, J=6.6 Hz), 8.34 (1H, d, J=8.2 Hz), 8.89 (1H, s).

Example 61

Preparation of 5-(6-methoxypyridin-3-yl)-5-methyl-3-(2-{2-[3-propyl-8-(trifluoromethyl)quinolin-4-yloxy]ethoxy}ethyl)imidazolidine-2,4-dione

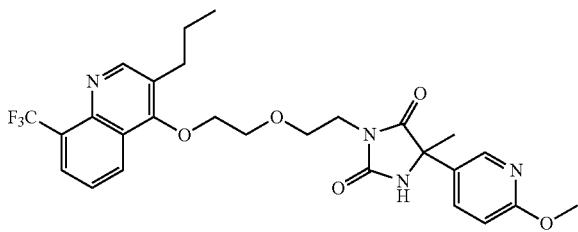

2-chloroethyl ether was used in place of 1,6-dibromohexane in Example 59 for a similar reaction and treatment, and the title compound was obtained as a colorless oil.

$^1$H-NMR (CDCl$_3$) δ: 1.01 (3H, t, J=7.3 Hz), 1.64-1.79 (5H, m), 2.78 (2H, d, J=7.3 Hz), 3.77 (3H, s), 3.84 (6H, s), 4.10 (2H, s), 5.96 (1H, s), 6.57 (1H, d, J=8.6 Hz), 7.56-7.65 (2H, m), 7.98 (1H, d, J=6.9 Hz), 8.21 (1H, s), 8.30 (1H, d, J=8.2 Hz), 8.89 (1H, s).

Example 62

Preparation of 5-(4-isopropoxyphenyl)-5-methyl-3-(2-{2-[3-propyl-8-(trifluoromethyl)quinolin-4-yloxy]ethoxy}ethyl)imidazolidine-2,4-dione

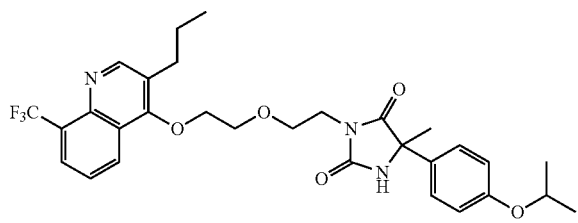

2-chloroethyl ether was used in place of 1,6-dibromohexane in Example 58 for a similar reaction and treatment, and the title compound was obtained as a colorless oil.

$^1$H-NMR (CDCl$_3$) δ: 1.01 (3H, t, J=7.3 Hz), 1.22 (6H, d, J=5.9 Hz), 1.68-1.78 (5H, m), 2.78 (2H, d, J=7.3 Hz), 3.83 (6H, s), 4.09 (2H, s), 4.34 (1H, septet, J=5.9 Hz), 5.94 (1H, s), 6.72 (2H, d, J=8.6 Hz), 7.31 (2H, t, J=8.6 Hz), 7.59 (1H, dd, J=6.9, 8.2 Hz), 7.99 (1H, d, J=6.9 Hz), 8.35 (1H, d, J=8.2 Hz), 8.89 (1H, s).

Test Example 1

Transactivation Assay

<Construction of Plasmid>

The ligand-binding domain (LBD) of a human LXRα and LXRβ cDNA was inserted adjacent to an yeast GAL4-transcription factor DNA-binding domain (DBD) of a mammal expression vector pBIND (Promega) to prepare an expression construct, thereby to produce pBIND-LXRα/GAL4 and pBIND-LXRβ/GAL4, respectively. PG5luc, a GAL4-responsive reporter construct, is a known vector that is available from Promega, and contains 5 copies of GAL4-response element located adjacent to the promoter as well as a luciferase reporter gene.

<Assay>

Figure 4:
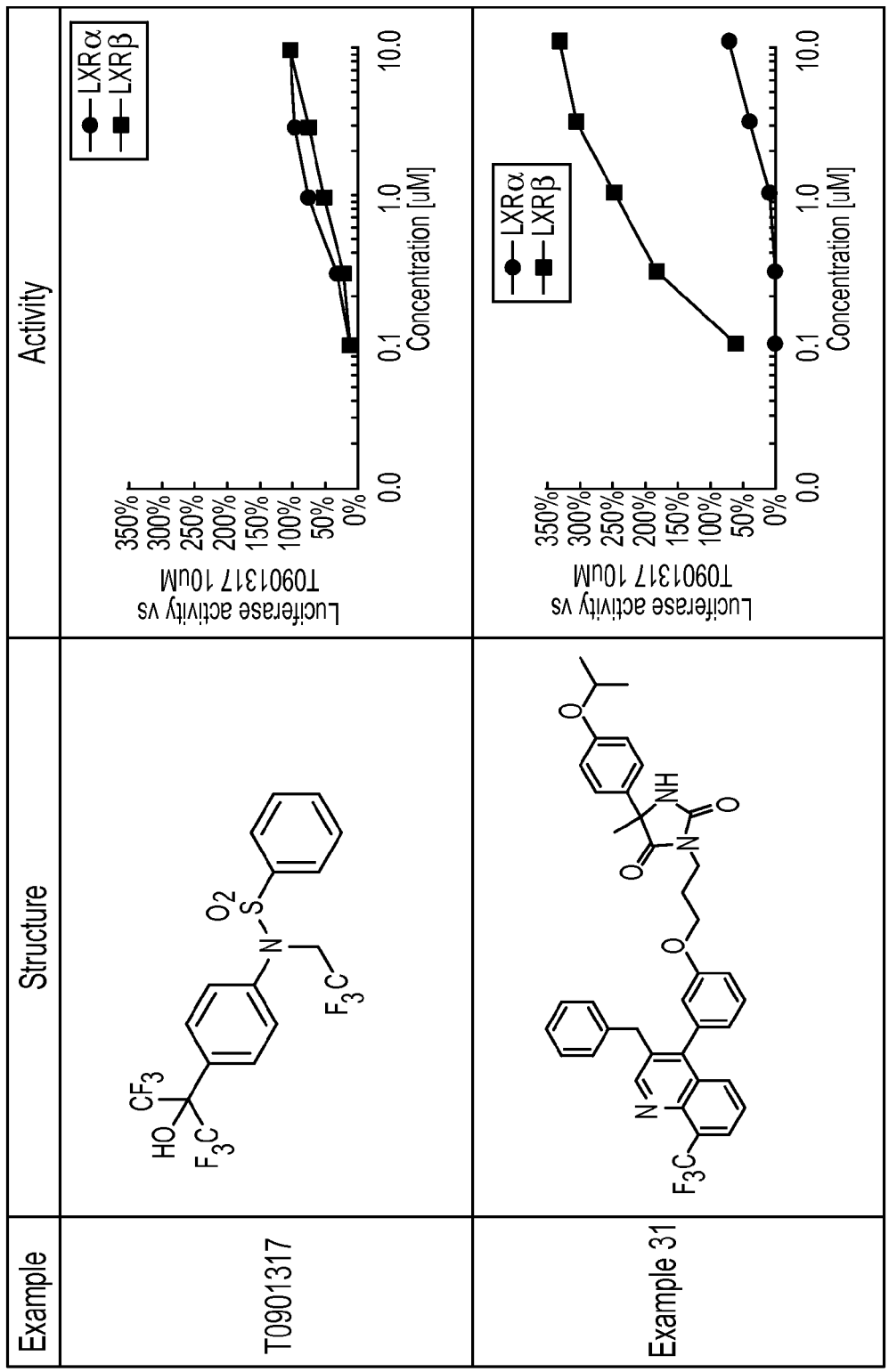
Figure 5:
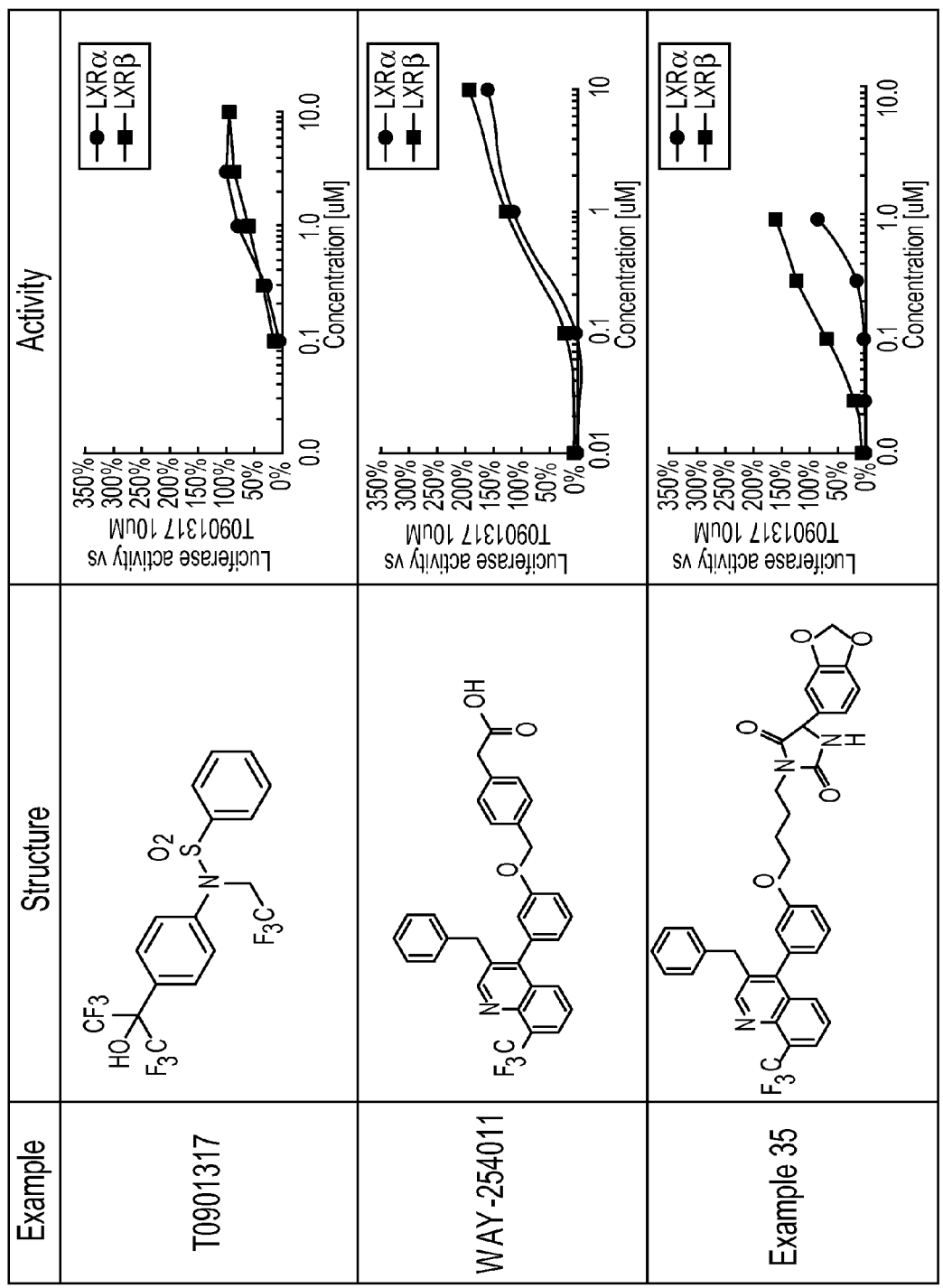
FIGS. 5 to 7 show the comparison in luciferase activity results between the embodiments of the present invention and the related arts (T0901317 and WAY-254011).
Figure 6:
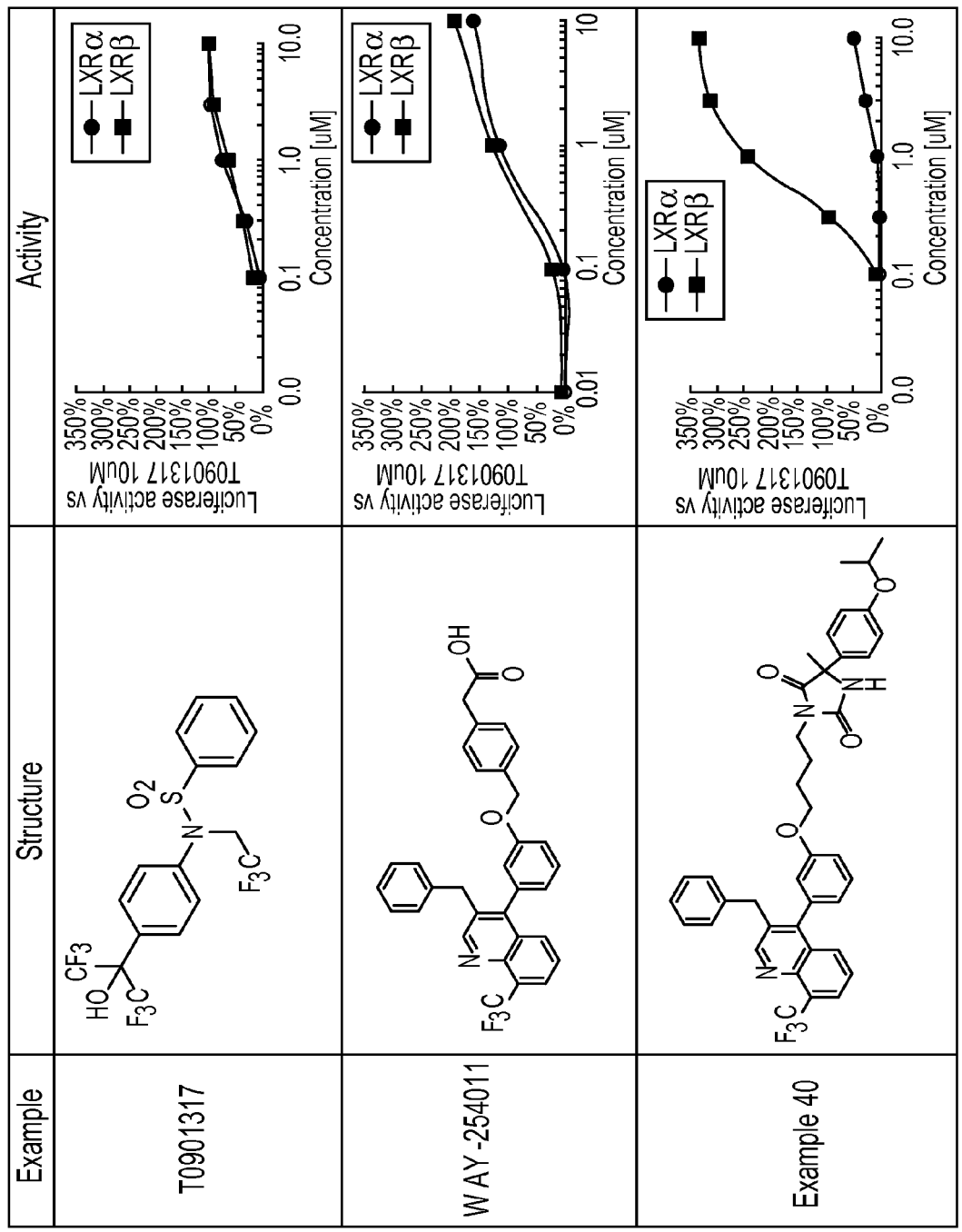
Figure 7:
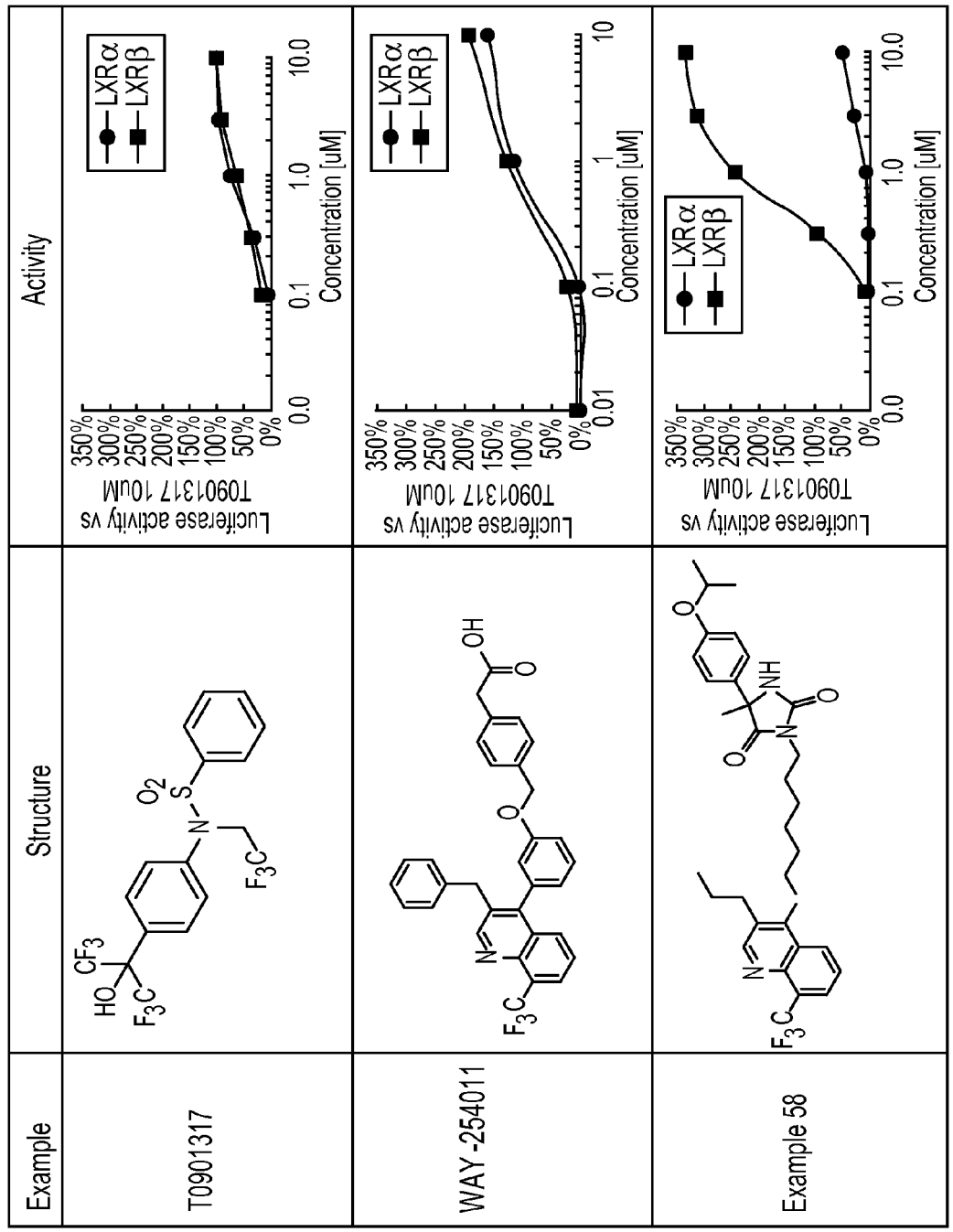

An LXRα/GAL4 or LXRβ/GAL4 hybrid and GAL4-responsive reporter vector pG5luc-stable-expression CHOK-1 cells were seeded under 5% CO$_2$ wet atmosphere at 37° C., at 20,000 cells/well on a 96-well plate containing HAM-F12 medium containing 10% immobilized bovine fetal serum, 100 units/ml of penicillin G, and 100 μg/ml of streptomycin sulfate. 24 hours later, the medium with a test compound dissolved therein over the test concentration range (0.01 μM, 0.1 μM, 1 μM, 10 μM) was added and incubated with the cells for 24 hours. By using Bright-Glo (Promega) as a luciferase assay substrate, and measuring the luminescence intensity with luminometer LB960 (Berthold Technologies), the effect of the test compound on the activation of luciferase transcription via the LXRα- or LXRβ-LBD was measured. At the same time, T0901317 (the compound of Example 12 of WO2000/54759) and WAY-254011 (compound 4 of Hu et al., Bioorg. Med. Chem. Lett., 18, pp. 54-59, 2008) were assessed as comparative compounds. The luciferase activity results are shown in FIGS. 1 to 5 as activity values (% eff) at the respective concentration of the test compound, relative to the T0901317 luminescence intensity of 100 at 10 μM.

<Results>

As shown in FIGS. 1 to 5, it was confirmed experimentally that the quinoline compound of the present invention is an LXR agonist having a higher selectivity to LXRβ than T0901317 which is a control agent. Further, WAY-254011 which also has a quinoline skeleton was not found to have an LXRβ-selective agonist effect. This proves that the idea of the present invention that an introduction of a hydantoin moiety leads to an LXRβ-selective agonist effect is correct.

The invention claimed is:

1. A quinoline compound represented by the following general formula (1) or salt thereof:

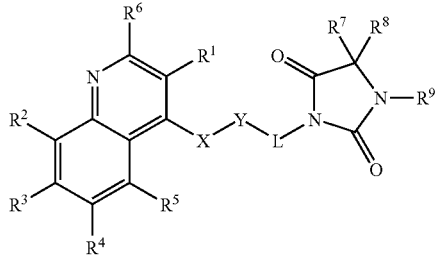

(wherein $R^1$ represents a hydrogen atom, halogen atom, $C_{1-8}$ alkyl group, $C_{3-8}$ cycloalkyl group, $C_{2-8}$ alkenyl group, $C_{3-8}$ cycloalkenyl group, $C_{3-8}$ cycloalkenyl-$C_{1-8}$ alkyl group, $C_{1-8}$ alkoxy group, $C_{6-10}$ aryl group, $C_{6-10}$ aryl $C_{1-8}$ alkyl group, $C_{6-10}$ aryl $C_{2-6}$ alkenyl group, $C_{1-8}$ acyl group, $C_{6-10}$ arylcarbonyl group, $C_{1-8}$ alkylthio group, $C_{1-8}$ alkylsulfinyl group, $C_{1-8}$ alkylsulfonyl group, $C_{6-10}$ arylsulfonyl group, nitro group, amino group, mono $C_{1-8}$ alkylamino group, di $C_{1-8}$ alkylamino group, $C_{3-8}$ cycloalkyl $C_{1-8}$ alkyl group, $C_{3-8}$ cycloalkyl $C_{2-8}$ alkenyl group, $C_{3-8}$ cycloalkyl $C_{2-8}$ alkynyl group, halo $C_{1-8}$ alkyl group, or cyano group, wherein the $C_{6-10}$ aryl may be substituted with 1 to 3 same or different substituents selected from the following group A; $R^2$ represents a hydrogen atom, $C_{1-8}$ alkyl group, halo $C_{1-8}$ alkyl group, or halogen atom; $R^3$, $R^4$, $R^5$, and $R^6$ each independently represents a hydrogen atom, halogen atom, or $C_{1-8}$ alkyl group; $R^7$ and $R^8$ each independently represents a hydrogen atom, $C_{1-8}$ alkyl group, $C_{3-8}$ cycloalkyl group, $C_{3-8}$ cycloalkyl $C_{1-8}$ alkyl group, $C_{6-10}$ aryl group, or 5- to 11-membered heterocyclic group, wherein the $C_{6-10}$ aryl and 5- to 11-membered heterocycle may be substituted with 1 to 3 same or different substituents selected from the following group A, or $R^7$ and $R^8$ may together form a 5- to 7-membered carbocycle; $R^9$ represents a hydrogen atom, $C_{1-8}$ alkyl group, halo $C_{1-6}$ alkyl group, $C_{3-8}$ cycloalkyl group, or $C_{3-8}$ cycloalkyl $C_{1-8}$ alkyl group; X represents a bond or a $C_{1-8}$ alkyl chain, $C_{6-10}$ aryl chain, or 5- to 11-membered heteroaryl chain; Y represents a —O—, —S—, or —N($R^{10}$)—; $R^{10}$ represents a hydrogen atom or $C_{1-8}$ alkyl group; and L represents a $C_{1-8}$ alkyl chain or $C_{2-8}$ alkenyl chain),

[Group A: halogen atom, $C_{1-8}$ alkyl group, halo $C_{1-8}$ alkyl group, $C_{2-8}$ alkenyl group, $C_{2-8}$ alkynyl group, $C_{3-8}$ cycloalkyl group, cyano group, nitro group, hydroxy group, amino group, mono $C_{1-8}$ alkylamino group, di $C_{1-8}$ alkylamino group, $C_{1-8}$ alkoxy group, halo $C_{1-8}$ alkoxy group, $C_{1-8}$ acyl group, carboxyl group, $C_{1-8}$ acyloxy group, $C_{1-8}$ alkoxycarbonyl group, carbamoyl group, $C_{6-10}$ aryl group, 5- to 11-membered heteroaryl group, $C_{6-10}$ aryl $C_{1-8}$ alkoxy group, $C_{1-8}$ alkylthio group, $C_{1-8}$ alkylsulfinyl group, $C_{1-8}$ alkylsulfonyl group, $C_{6-10}$ arylthio group, $C_{6-10}$ arylsulfinyl group, and $C_{6-10}$ arylsulfonyl group].

2. The quinoline compound or salt thereof according to claim 1, wherein $R^1$ is a $C_{1-8}$ alkyl group or $C_{6-10}$ aryl $C_{1-8}$ alkyl group.

3. The quinoline compound or salt thereof according to claim 1, wherein $R^2$ is a halo $C_{1-8}$ alkyl group.

4. The quinoline compound or salt thereof according to claim 1, wherein $R^7$ and $R^8$ are each independently a $C_{1-8}$ alkyl group, $C_{6-10}$ aryl group, or 5- to 11-membered heterocyclic group, wherein the $C_{6-10}$ aryl and 5- to 11-membered heterocycle may be substituted with 1 to 3 same or different substituents selected from the following group A, [Group A: halogen atom, $C_{1-8}$ alkyl group, halo $C_{1-8}$ alkyl group, $C_{2-8}$ alkenyl group, $C_{2-8}$ alkynyl group, $C_{3-8}$ cycloalkyl group, cyano group, nitro group, hydroxy group, amino group, mono $C_{1-8}$ alkylamino group, di $C_{1-8}$ alkylamino group, $C_{1-8}$ alkoxy group, halo $C_{1-8}$ alkoxy group, $C_{1-8}$ acyl group, carboxyl group, $C_{1-8}$ acyloxy group, $C_{1-8}$ alkoxycarbonyl group, carbamoyl group, $C_{6-10}$ aryl group, 5- to 11-membered heteroaryl group, $C_{6-10}$ aryl $C_{1-8}$ alkoxy group, $C_{1-8}$ alkylthio group, $C_{1-8}$ alkylsulfinyl group, $C_{1-8}$ alkylsulfonyl group, $C_{6-10}$ arylthio group, $C_{6-10}$ arylsulfinyl group, and $C_{6-10}$ arylsulfonyl group].

5. A medicine composition comprising a therapeutically effective amount of the quinoline compound or salt thereof according to claim 1 as an active ingredient.

6. The medicine composition according to claim 5, which is a therapeutic agent for atherosclerosis, arteriosclerosis resulting from diabetes, dyslipidemia, hypercholesterolemia, diabetes, or Alzheimer's disease.

7. An LXR regulator containing the quinoline compound or salt thereof according to claim 1 as an active ingredient.

8. A pharmaceutical composition comprising the quinoline compound or salt thereof according to claim 1 and a pharmaceutically acceptable carrier.

9. A method for treating atherosclerosis, arteriosclerosis resulting from diabetes, dyslipidemia, hypercholesterolemia, diabetes, or Alzheimer's disease, in a subject in need thereof, comprising administering to said subject a therapeutically effective amount of the quinoline compound or salt thereof according to claim 1.

10. A medicine composition according to claim 5, wherein the medicine composition is administered in the form of an oral preparation, injection, suppository, ointment, inhalation, eye-drops, nasal preparation, or adhesive patch.

11. The LXR regulator according to claim 7, wherein said LXR regulator has a higher selectivity for activating LXRβ expression than a LXRα expression.

* * * * *